United States Patent
Takahashi et al.

(10) Patent No.: US 9,844,549 B2
(45) Date of Patent: Dec. 19, 2017

(54) 2-AMINOTHIAZOLE DERIVATIVE OR SALT THEREOF

(71) Applicant: ASTELLAS PHARMA INC., Chuo-ku (JP)

(72) Inventors: Taisuke Takahashi, Tokyo (JP); Hiroaki Tanaka, Tokyo (JP); Michinori Akaiwa, Tokyo (JP); Kenji Negoro, Tokyo (JP); Hisashi Mihara, Tokyo (JP); Hideyoshi Fuji, Tokyo (JP); Hajime Takamatsu, Tokyo (JP)

(73) Assignee: Astellas Pharma Inc., Chuo-ku (JP)

( * ) Notice: Subject to any disclaimer, the term of this patent is extended or adjusted under 35 U.S.C. 154(b) by 0 days.

(21) Appl. No.: 15/506,561

(22) PCT Filed: Aug. 25, 2015

(86) PCT No.: PCT/JP2015/073914
§ 371 (c)(1),
(2) Date: Feb. 24, 2017

(87) PCT Pub. No.: WO2016/031833
PCT Pub. Date: Mar. 3, 2016

(65) Prior Publication Data
US 2017/0290824 A1    Oct. 12, 2017

(30) Foreign Application Priority Data
Aug. 26, 2014    (JP) .................................. 2014-171092

(51) Int. Cl.
*C07D 417/14* (2006.01)
*A61K 31/506* (2006.01)
*A61K 31/496* (2006.01)
*A61K 31/4439* (2006.01)
*C07D 417/12* (2006.01)

(52) U.S. Cl.
CPC ........ *A61K 31/496* (2013.01); *A61K 31/4439* (2013.01); *A61K 31/506* (2013.01); *C07D 417/12* (2013.01); *C07D 417/14* (2013.01)

(58) Field of Classification Search
CPC  C07D 417/14; C07D 417/12; A61K 31/4439; A61K 31/496; A61K 31/506
USPC ............. 544/295, 328, 360, 364; 546/270.7; 514/252.14, 252.19, 256, 342
See application file for complete search history.

(56) References Cited

U.S. PATENT DOCUMENTS

| | | |
|---|---|---|
| 2005/0153977 A1 | 7/2005 | Sugasawa et al. |
| 2006/0074068 A1 | 4/2006 | Provins et al. |
| 2006/0194844 A1 | 8/2006 | Sugasawa et al. |
| 2010/0222329 A1 | 9/2010 | Sugasawa et al. |
| 2010/0222361 A1 | 9/2010 | Sugasawa et al. |
| 2013/0079351 A1 | 3/2013 | Sugasawa et al. |
| 2015/0018343 A1 | 1/2015 | Swinnen et al. |
| 2015/0126487 A1 | 5/2015 | Sakamoto et al. |
| 2015/0307497 A1 | 10/2015 | Sugimoto et al. |
| 2016/0002218 A1 | 1/2016 | Takahashi et al. |

FOREIGN PATENT DOCUMENTS

| | | |
|---|---|---|
| WO | 00/62778 A1 | 10/2000 |
| WO | 03/062233 A1 | 7/2003 |
| WO | 03/087064 A1 | 10/2003 |
| WO | 2005/007651 A1 | 1/2005 |
| WO | 2012/016217 A1 | 2/2012 |
| WO | 2013/091773 A1 | 6/2013 |
| WO | 2013/129622 A1 | 9/2013 |
| WO | 2014/077401 A1 | 5/2014 |
| WO | 2014/133056 A1 | 9/2014 |
| WO | 2015/186821 A1 | 12/2015 |

OTHER PUBLICATIONS

Uchiyama et al., Muscarinic receptor subtypes of the bladder and gastrointestinal tract, J. Smooth Muscle Res., 40(6), pp. 237-247, 2004.*
McCrery et al., The emergence of new drugs for overactive bladder, Expert Opin Emerginc Drugs, 11(1), pp. 125-136, 2006.*
International Preliminary Report on Patentability and Written Opinion dated Feb. 28, 2017 in PCT/JP2015/073914 (with English translation).
N. J. M. Birdsall, et al., "Subtype-Selective Positive Cooperative Interactions Between Brucine Analogs and Acetylcholine at Muscarinic Receptors: Functional Studies," Molecular Pharmacology, 1999, vol. 55, pp. 778-786.

(Continued)

*Primary Examiner* — Deepak Rao
(74) *Attorney, Agent, or Firm* — Oblon, McClelland, Maier & Neustadt, L.L.P.

(57) ABSTRACT

A compound which is useful as an active ingredient for a pharmaceutical composition for treating urine storage dysfunction, voiding dysfunction, lower urinary tract dysfunction, and the like. The present inventors have found that a 2-aminothiazole derivative has an excellent muscarinic $M_3$ receptor-positive allosteric modulator activity and is expected as an agent for preventing or treating bladder/urinary tract diseases associated with bladder contractions via a muscarinic $M_3$ receptor, thereby completing the present invention. 2-aminothiazole derivative or a salt thereof of the present invention is expected as an agent for preventing or treating bladder/urinary tract diseases associated with bladder contractions via a muscarinic $M_3$ receptor, for example voiding dysfunction such as underactive bladder.

13 Claims, No Drawings

(56) References Cited

OTHER PUBLICATIONS

S. Lazareno, et al., "Analogs of WIN 62,577 Define a Second Allosteric Site on Muscarinic Receptors," Molecular Pharmacology, 2002, vol. 62, No. 6, pp. 1492-1505.
International Search Report dated Nov. 2, 2015 in PCT/JP2015/073914 filed Aug. 25, 2015.

\* cited by examiner

2-AMINOTHIAZOLE DERIVATIVE OR SALT THEREOF

TECHNICAL FIELD

The present invention relates to a 2-aminothiazole derivative or a salt thereof which is expected as an active ingredient for a pharmaceutical composition, in particular, a pharmaceutical composition for treating bladder/urinary tract diseases related to bladder contractions via a muscarinic $M_3$ receptor.

BACKGROUND ART

The important roles of the lower urinary tract are urine storage and voiding, which are regulated by a coordinated action of the bladder and the urethra. That is, during urine storage, the bladder smooth muscle is relaxed and the urethral sphincter is contracted, whereby a state in which urethral resistance is high is maintained and urinary continence is maintained. On the other hand, during voiding, the bladder smooth muscle is contracted, the urethra smooth muscle is relaxed, and contraction of the external urethral sphincter is also inhibited. Examples of the lower urinary tract disorder include urine storage dysfunction such as overactive bladder, in which urine cannot be retained during urine storage, and voiding dysfunction, in which urine cannot be drained sufficiently during voiding due to an increase in the urethral resistance or a decrease in the bladder contractile force. These two disorders may develop simultaneously in some cases.

Voiding dysfunction is caused by a decrease in the bladder contractile force, an increase in urethral resistance or the like during voiding, and causes difficulty in voiding, straining during voiding, a weak urine stream, extension of voiding time, an increase in residual urine, a decrease in voiding efficiency, or the like. The decrease in the bladder contractile force during voiding is referred to as underactive bladder, acontractile bladder, or the like. As a factor causing such a decrease in the bladder contractile force during voiding, for example, aging, diabetes mellitus, benign prostatic hyperplasia, neurological diseases such as Parkinson's disease and multiple sclerosis, spinal cord injury, neurological disorders by pelvic surgery, and the like have been known (Reviews in Urology, 15: pp. 11-22 (2013)).

As a mechanism to cause bladder contraction during voiding, involvement of muscarinic receptor stimulation has been known. That is, during urination, the pelvic nerve which is a parasympathetic nerve governing the bladder is excited to release acetylcholine from nerve terminals. The released acetylcholine binds to a muscarinic receptor present in the bladder smooth muscle to cause contraction of the bladder smooth muscle (Journal of Pharmacological Sciences, 112: pp. 121-127 (2010)). The muscarinic receptors are currently classified into five subtypes, $M_1$, $M_2$, $M_3$, $M_4$, and $M_5$, and it has been known that the subtypes involving the contraction in the bladder smooth muscle is mainly $M_3$ (Pharmacological Reviews, 50: pp. 279-290 (1998); The Journal of Neuroscience, 22: pp. 10627-10632 (2002)).

As a therapeutic drug for a decrease in bladder contractile force during voiding, bethanechol chloride which is a non-selective muscarinic receptor agonist and distigmine bromide which is a cholinesterase inhibitor have been known. However, it has been known that these drugs have cholinergic side effects such as diarrhea, abdominal pain, and perspiration. In addition, there may be cases where cholinergic crisis is occurred as a serious side effect, which require attention during use (Ubretid (registered trademark), tablet 5 mg, package insert, Torii Pharmaceutical Co., Ltd., and Besacholine (registered trademark) powder 5%, package insert, Eisai Co., Ltd.).

On the other hand, as a cause of an increase in urethral resistance, voiding dysfunction associated with benign prostatic hyperplasia has been well-known, which is characterized in that the urethra is partially occluded by nodular enlargement of the prostatic tissue. Currently, an adrenergic $\alpha_1$ receptor antagonist has been used as a therapeutic drug for voiding dysfunction associated with benign prostatic hyperplasia (Pharmacology, 65: pp. 119-128 (2002)). On the other hand, the effectiveness of the adrenaline a1 receptor antagonist for voiding dysfunction that is not associated with benign prostatic hyperplasia is unclear (Journal of Pharmacological Sciences, 112: pp. 121-127 (2010)).

Furthermore, for voiding dysfunction caused by a decrease in bladder contractile force or an increase in urethral resistance, residual urine after voiding may be observed in some cases. The increased residual urine may cause a decrease in effective bladder capacity, and thus cause overactive bladder symptoms such as urinary frequency or severe symptoms such as hydronephrosis in some cases.

There has been a demand for a more effective therapeutic drug for such bladder/urethral diseases due to a decrease in the bladder contractile force or an increase in urethral resistance during voiding, or symptoms thereof (Reviews in Urology, 15: pp. 11-22 (2013)).

It is described that a compound represented by the following formula (A) disclosed in Patent Document 1 and a compound represented by the following formula (A1) disclosed in Patent Document 2 each have a Ba/F3 cell proliferative activity through a human c-myeloproliferative leukemia virus type P (c-Mpl), and have thrombocyte increasing activity.

[Chem. 1]

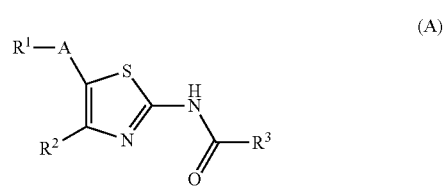

(A)

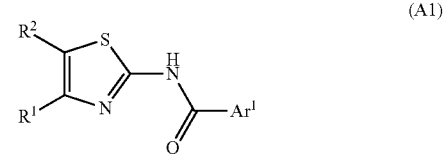

(A1)

(in which $R^3$ and $Ar^1$ represent an aromatic hetero ring which may be substituted, or the like. For the other symbols, refer to the patent publications).

Patent Document 3 discloses that a compound represented by the following formula (B) has an AMP-activated protein kinase (AMPK) pathway activating action.

[Chem. 2]

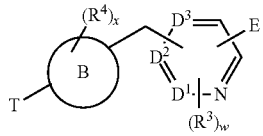

(in which ring B represents a heteroarylene or the like, J represents —NR$^{13}$— or the like, D$^1$, D$^2$ and D$^3$ each represent N, CH, or the like, E represents —NR$^1$R$^2$ or the like, R$^1$ and R$^2$ may be combined with the adjacent nitrogen atom to form a heterocycloalkyl group, R$^4$ represents aryl or the like which may be substituted, and T represents —NR$^8$R$^9$, heterocycloalkyl or the like. For the other symbols, refer to this publication).

Non-Patent Document 1 discloses that a compound represented by the following formula (C1) is an allosteric enhancer of a muscarinic M$_3$ receptor.

[Chem. 3]

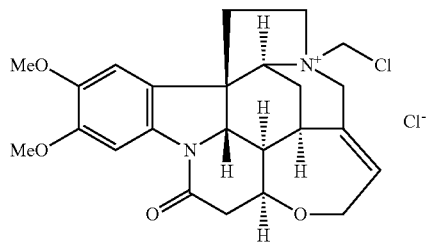

Non-Patent Document 2 discloses that WIN 62,577 represented by the following formula is a rat NK1 receptor antagonist and, at the same time, an allosteric enhancer of a muscarinic receptor.

[Chem. 4]

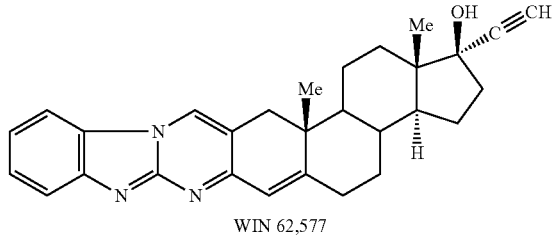

WIN 62,577

RELATED ART

Patent Document

[Patent Document 1] International Publication 2005/007651
[Patent Document 2] International Publication 2003/062233
[Patent Document 3] International Publication 2012/016217

Non-Patent Document

[Non-Patent Document 1] Molecular Pharmacology, 55: pp 778-786 (1999)
[Non-Patent Document 2] Molecular Pharmacology, 62: pp 1492-1505 (2002)

DISCLOSURE OF INVENTION

Problems to be Solved by the Invention

The present invention provides a novel compound which is expected as an active ingredient for a pharmaceutical composition, in particular, for a pharmaceutical composition for preventing or treating bladder/urinary tract diseases associated with bladder contractions via a muscarinic M$_3$ receptor, which has a muscarinic M$_3$ receptor-positive allosteric modulator activity.

Means for Solving the Problems

The present inventors have found that a 2-aminothiazole derivative has an excellent muscarinic M$_3$ receptor-positive allosteric modulator activity and is expected as an agent for preventing or treating bladder/urinary tract diseases associated with bladder contractions via a muscarinic M$_3$ receptor, thereby completing the present invention.

That is, the present invention relates to a compound of the formula (I) or a salt thereof, and a pharmaceutical composition comprising a compound of the formula (I) or a salt thereof and an excipient.

[Chem. 5]

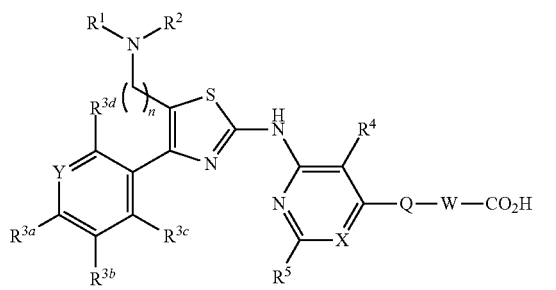

(in which,
X is C—H or N,
Y is C—R$^{3e}$ or N,
R$^1$ and R$^2$ are the same as each other or are different from each other, and are C$_{1-6}$ alkyl which may be substituted, or R$^1$ and R$^2$ may be combined with the adjacent nitrogen atom to form cyclic amino which may be substituted,
R$^{3a}$, R$^{3b}$, R$^{3c}$, and R$^{3d}$ are the same as each other or are different from each other, and are H, halogen, C$_{1-6}$ alkyl, halogeno C$_{1-6}$ alkyl, —O—C$_{1-6}$ alkyl, C$_{2-6}$ alkenyl, C$_{3-8}$ cycloalkyl, or —O-halogeno C$_{1-6}$ alkyl,
in a case where Y is C—R$^{3e}$, R$^{3e}$ is H, halogen, C$_{1-6}$ alkyl, halogeno C$_{1-6}$ alkyl, —O—C$_{1-6}$ alkyl, C$_{2-6}$ alkenyl, C$_{3-8}$ cycloalkyl, or —O-halogeno C$_{1-6}$ alkyl,
R$^4$ is H, halogen, or —O—C$_{1-6}$ alkyl,
R$^5$ is H, C$_{1-6}$ alkyl, or —NR$^{51}$R$^{52}$
Q is heterocyclylene which may be substituted,
W is a bond, C$_{1-6}$ alkylene, —O—C$_{1-6}$ alkylene, or —N(R$^N$)—C$_{1-6}$ alkylene,
R$^{51}$ and R$^{52}$ are the same as each other or are different from each other, and are H or C$_{1-6}$ alkyl,
R$^N$ is H or C$_{1-6}$ alkyl, and
n is 0 or 1).

In addition, the invention relates to a compound of the formula (I) or a salt thereof, and a pharmaceutical composition comprising a compound of the formula (I) or a salt thereof and an excipient.

In which,

X is C—H or N,

Y is C—$R^{3e}$ or N, $R^1$ and $R^2$ are the same as each other or are different from each other, and are $C_{1-6}$ alkyl which may be substituted, or $R^1$ and $R^2$ may be combined with the adjacent nitrogen atom to form cyclic amino which may be substituted, $R^{3a}$, $R^{3b}$, $R^{3c}$, $R^{3d}$, and $R^{3e}$ are the same as each other or are different from each other, and are H, halogen, $C_{1-6}$ alkyl, halogeno $C_{1-6}$ alkyl, —O—$C_{1-6}$ alkyl, $C_{2-6}$ alkenyl, $C_{3-8}$ cycloalkyl, or —O-halogeno $C_{1-6}$ alkyl, $R^4$ is H, halogen, or —O—$C_{1-6}$ alkyl, $R^5$ is H, $C_{1-6}$ alkyl, or —$NR^{51}R^{52}$, Q is heterocyclylene which may be substituted, W is a bond, $C_{1-6}$ alkylene, —O—$C_{1-6}$ alkylene, or —N($R^N$)—$C_{1-6}$ alkylene, $R^{51}$ and $R^{52}$ are the same as each other or are different from each other, and are H or $C_{1-6}$ alkyl, $R^N$ is H or $C_{1-6}$ alkyl, and n is 0 or 1.

Further, unless specifically described otherwise, when symbols in one formula in the present specification are also used in other formulae, same symbols denote same meanings.

Further, the configuration of the compound disclosed in Patent Document 1 is different from that of the compound of the present application in that an acyl group is substituted to an amino group at 2-position of thiazole. In addition, Patent Document 1 neither discloses nor suggests an action on a muscarinic receptor or an action on bladder/urinary tract diseases.

Furthermore, Patent Document 2 does not disclose a specific compound which is a compound of the formula (B) wherein ring B is thiazole, and neither discloses nor suggests an action on a muscarinic receptor or an action on bladder/urinary tract diseases.

Further, the present invention relates to a pharmaceutical composition comprising the compound of the formula (I) or a salt thereof, and a pharmaceutically acceptable excipient. Furthermore, the present invention relates to a pharmaceutical composition for preventing or treating bladder/urinary tract diseases associated with bladder contractions via a muscarinic $M_3$ receptor, comprising the compound of the formula (I) or a salt thereof. Furthermore, the present invention relates to an agent for preventing or treating bladder/urinary tract diseases associated with bladder contractions via a muscarinic $M_3$ receptor, comprising the compound of the formula (I) or a salt thereof.

Moreover, the present invention relates to use of the compound of the formula (I) or a salt thereof for the manufacture of a pharmaceutical composition for preventing or treating bladder/urinary tract diseases associated with bladder contractions via a muscarinic $M_3$ receptor; use of the compound of the formula (I) or a salt thereof for preventing or treating bladder/urinary tract diseases associated with bladder contractions via a muscarinic $M_3$ receptor; the compound of the formula (I) or a salt thereof for preventing or treating bladder/urinary tract diseases associated with bladder contractions via a muscarinic $M_3$ receptor; and a method for preventing or treating bladder/urinary tract diseases associated with bladder contractions via a muscarinic $M_3$ receptor, comprising administering to a subject an effective amount of the compound of the formula (I) or a salt thereof. Further, the "subject" is a human or a non-human animal in need of the prevention or treatment, and in one embodiment, a human in need of the prevention or treatment.

Effects of the Invention

The compound represented by the formula (I) or a salt thereof is expected as a preventing or treating agent for bladder/urinary tract diseases associated with bladder contractions via a muscarinic $M_3$ receptor, which has a muscarinic $M_3$ receptor-positive allosteric modulator activity.

EMBODIMENTS FOR CARRYING OUT THE INVENTION

Hereinafter, the present invention will be described in detail.

In general, "the positive allosteric modulator" is a compound which binds to an allosteric site different from a ligand binding site, and has an effect of increasing the affinity of an agonist to a receptor by mainly causing a structural change in a receptor, and thus changing the signal level of an agonist. In the living body, the positive allosteric modulator does not exhibit an agonistic effect by itself, and increases the effect of an endogenous agonist. As the advantages of positive allosteric modulator over the agonists, (1) being capable of avoiding the side effects since the positive allosteric modulator exhibits an enhancement in the endogenous agonist stimulation dependently, (2) having a possibility of obtaining high subtype selectivity since the positive allosteric modulator binds to a site other than a ligand binding site, (3) less probability of causing desensitization, which can be seen with the agonists and the like are pointed out (Pharmacological Reviews, 63: pp. 59-126 (2011)).

In the present specification, "the muscarinic $M_3$ receptor-positive allosteric modulator" means a compound which enhances an effect via the muscarinic $M_3$ receptor by an agonist stimulation-dependent or nerve stimulation-dependent manner. Accordingly, only during voiding, the effect on enhancing bladder contraction is expected and the muscarinic $M_3$ receptor-positive allosteric modulator is possibly useful as an agent for improving various symptoms associated with voiding dysfunction. Further, by such a specific action during voiding, it is expected that it is possible to decrease cholinergic side effects, known to be induced with bethanechol chloride and distigmine bromide. In addition, since the muscarinic $M_3$ receptor-positive allosteric modulator increases bladder contractile force during voiding, an effect in voiding dysfunction which is caused by an increase in urethral resistance can also be expected. A decrease in residual urine by such improvement of voiding dysfunction leads to an increase in the effective bladder capacity, and thus, it can be expected to improve urine storage functions as well as to decrease renal disorder. Thus, the muscarinic $M_3$ receptor-positive allosteric modulator is expected to be useful as an agent for preventing or treating bladder/urinary tract diseases related to bladder contractions via a muscarinic $M_3$ receptor. The present inventors have newly discovered a compound that acts as the modulator, thereby completing the present invention.

In the present specification, examples of the "bladder/urinary tract diseases associated with bladder contractions via a muscarinic $M_3$ receptor" include voiding dysfunction or urine storage dysfunction in underactive bladder, hypotonic bladder, acontractile bladder, detrusor underactivity, neurogenic bladder, urethra relaxation failure, detrusor-external urethral sphincter dyssynergia, overactive bladder, urinary frequency, nocturia, urinary incontinence, benign prostatic hyperplasia, interstitial cystitis, chronic prostatitis, urethral calculus, or the like, preferably, voiding dysfunction or urine storage dysfunction in underactive bladder, hypotonic bladder, acontractile bladder, detrusor underactivity, and neurogenic bladder.

The "alkyl" is linear alkyl and branched alkyl. Accordingly, the "$C_{1-6}$ alkyl" is linear or branched alkyl having 1 to 6 carbon atoms, and specific examples thereof include methyl, ethyl, n-propyl, isopropyl, n-butyl, isobutyl, sec-butyl, tert-butyl, n-pentyl, or n-hexyl. $C_{1-4}$ alkyl is preferably used. In one embodiment, examples thereof include methyl, ethyl, n-propyl, isopropyl, n-butyl, isobutyl, sec-butyl, or tert-butyl; in one embodiment, a group selected from the group consisting of methyl, ethyl, isopropyl, and isobutyl; in one embodiment, methyl or ethyl; in one embodiment, methyl; and in another embodiment, ethyl.

The "alkenyl" is linear alkenyl and branched alkenyl. Accordingly, the "$C_{2-6}$ alkenyl" is linear or branched alkenyl having 2 to 6 carbon atoms, and specific examples thereof include vinyl, propenyl, butenyl, pentenyl, 1-methylvinyl, 1-methyl-2-propenyl, 1,3-butadienyl, and 1,3-pentadienyl, and the like. In one embodiment, examples thereof include $C_{2-4}$ alkenyl, and in one embodiment, vinyl or propenyl.

The "alkylene" is linear alkylene and branched alkylene. Accordingly, the "$C_{1-6}$ alkylene" is linear or branched alkylene having 1 to 6 carbon atoms, and examples thereof include methylene, ethylene, propylene, tetramethylene, pentamethylene, hexamethylene, methyl methylene, ethylethylene, 1,2-dimethyl ethylene, or 1,1,2,2-tetramethyl ethylene, and the like. In one embodiment, examples thereof include $C_{1-3}$ alkylene; in one embodiment, methylene or ethylene; in one embodiment, methylene; and in another embodiment, ethylene.

The "halogeno-$C_{1-6}$ alkyl" is $C_{1-6}$ alkyl substituted with at least one halogen atom; in one embodiment, $C_{1-6}$ alkyl substituted with 1 to 5 halogen atoms; in one embodiment, difluoromethyl or trifluoromethyl; and in one embodiment, trifluoromethyl.

The "cycloalkyl" is a saturated hydrocarbon cyclic group. Accordingly, the "$C_{3-8}$ cycloalkyl" is a saturated hydrocarbon cyclic group having 3 to 8 ring members, and specific examples thereof include cyclopropyl, cyclobutyl, cyclopentyl, cyclohexyl, cycloheptyl, or cyclooctyl; in one embodiment, cyclopropyl, cyclobutyl, cyclopentyl, or cyclohexyl, each of which is $C_{3-6}$ cycloalkyl; and in one embodiment, cyclopropyl.

The "saturated hetero ring" is a 3- to 8-membered saturated ring, which has 1 to 4 hetero atoms selected from the group consisting of a nitrogen atom, an oxygen atom, and a sulfur atom as a ring-constituting atom, and may be bridged with $C_{1-6}$ alkylene, in which a sulfur atom as the ring-constituting atom may be oxidized. Specific examples thereof include azepane, diazepane, aziridine, azetidine, pyrrolidine, imidazolidine, piperidine, pyrazolidine, piperazine, azocane, thiomorpholine, thiazolidine, isothiazolidine, oxazolidine, morpholine, tetrahydrothiopyran, oxathiolane, oxirane, oxetane, dioxolane, tetrahydrofuran, tetrahydropyran, and 1,4-dioxane.

The "cyclic amino" has at least one nitrogen atom, and is a 4- to 7-membered monovalent group having a bond at the ring-constituting nitrogen atom in the "saturated hetero ring". Specific examples thereof include azetidinyl, pyrrolidinyl, piperidinyl, azepanyl, morpholinyl, thiomorpholinyl, piperazinyl, 1,4-diazepanyl, 1,4-oxazepanyl, or 1,4-thiazepanyl. In one embodiment, examples thereof include pyrrolidinyl, piperidinyl, azetidinyl, morpholinyl, or piperazinyl, in one embodiment, pyrrolidinyl, piperidinyl, or piperazinyl, in one embodiment, pyrrolidinyl, in another embodiment, piperidinyl, and in another embodiment, piperazinyl.

The "heterocyclylene" has at least one nitrogen atom, and is a divalent group having a bond at the ring-constituting nitrogen atom and other ring-constituting atom in the "saturated hetero ring". Specific examples thereof include pyrrolidine-diyl, piperidine-diyl, or piperazine-diyl.

The "halogen" means fluoro, chloro, bromo, or iodo; in one embodiment, fluoro, chloro, or bromo; in one embodiment, fluoro or chloro; in one embodiment, fluoro; and in another embodiment, chloro.

In one embodiment of the "cyclic amino" in "$R^1$ and $R^2$ may be combined with the adjacent nitrogen atom to form cyclic amino which may be substituted" of the formula (I), the examples thereof include azetidinyl, pyrrolidinyl, piperidinyl, or piperazinyl, and in one embodiment, pyrrolidinyl.

In one embodiment of "heterocyclylene" in Q of the formula (I), the examples thereof include pyrrolidine-diyl, piperidine-diyl, or piperazine-diyl, in one embodiment, pyrrolidine-1,3-diyl, piperidine-1,4-diyl, or piperazine-1,4-diyl, in one embodiment, piperidine-diyl or piperazine-diyl, and in one embodiment, piperidine-1,4-diyl or piperazine-1,4-diyl.

In addition, in a case where the "heterocyclylene" in Q of the formula (I) is pyrrolidine-1,3-diyl or piperidine-1,4-diyl, and the 3-position of pyrrolidine or the 4-position of piperidine is each bonded to W.

In one embodiment of W of the formula (1), the examples thereof include a bond, $C_{1-6}$ alkylene, —O—$C_{1-6}$ alkylene, or —N($R^N$)—$C_{1-6}$ alkylene, and the O of "—O—$C_{1-6}$ alkylene" and N($R^N$) of "—N($R^N$)—$C_{1-6}$ alkylene" are each bonded to Q.

In one embodiment of W of the formula (I), examples thereof include —$CH_2$—$CH_2$—, or —O—$CH_2$—.

In the present specification, the expression "which may be substituted" means "which is not substituted" or "which is substituted with 1 to 5 substituents". Further, if it has a plurality of substituents, the substituents may be the same as or different from each other.

Examples of the preferred substituent in "cyclic amino which may be substituted" and "heterocyclylene which may be substituted" include the following Group G.

Group G (a) $C_{1-6}$ alkyl which may be substituted with at least one group selected from the group consisting of —OH, —O—($C_{1-6}$ alkyl), —CN, —$SO_2$—($C_{1-6}$ alkyl), and halogen, (b) —OH, (c) —O—($C_{1-6}$ alkyl which may be substituted with at least one group selected from the group consisting of —OH, —O—($C_{1-6}$ alkyl), —CN, —$SO_2$—($C_{1-6}$ alkyl), and halogen), (d) $C_{3-8}$ cycloalkyl, (e) —O—($C_{3-8}$ cycloalkyl), (f) halogen, (g) —CN, (h) —$SO_2$—($C_{1-6}$ alkyl), (i) —$CO_2$—($C_{1-6}$ alkyl) and —COOH, (j) —CO—N($C_{1-6}$ alkyl)$_2$, —CO—NH($C_{1-6}$ alkyl), and —$CONH_2$, (k) —CO—($C_{1-6}$ alkyl), (l) —$SO_2$—N($C_{1-6}$ alkyl)$_2$, —$SO_2$—NH($C_{1-6}$ alkyl), and —$SO_2NH_2$, (m) —N($C_{1-6}$ alkyl)$_2$, —NH($C_{1-6}$ alkyl), and —$NH_2$, (n) a saturated heterocyclic group, (o) an —O-saturated heterocyclic group, and
(p) Oxo.

In addition, examples of the preferred substituent in "$C_{1-6}$ alkyl which may be substituted" include the groups described in (b) to (o) of the above-described Group G. In one embodiment, examples thereof include the substituent selected from the group consisting of —OH, —O—$C_{1-6}$ alkyl, and $C_{3-8}$ cycloalkyl.

In one embodiment, examples of the preferred substituent in "$C_{1-6}$ alkyl which may be substituted" of $R^1$ and $R^2$ include —O—$C_{1-6}$ alkyl or $C_{3-8}$ cycloalkyl. In one embodiment, examples thereof include methoxy or cyclopropyl, in one embodiment, methoxy, and in another embodiment, cyclopropyl.

In one embodiment of the preferred substituent in "$R^1$ and $R^2$ are combined with the adjacent nitrogen atom to form cyclic amino which may be substituted", the examples thereof include the groups described in (a) to (d) of the above-described Group G. In one embodiment, the examples thereof include $C_{1-6}$ alkyl, —O—$C_{1-6}$ alkyl, or $C_{3-8}$ cycloalkyl, in one embodiment, $C_{1-6}$ alkyl, in one embodiment, methyl or ethyl, in one embodiment, methyl, and in another embodiment, ethyl.

In one embodiment of the acceptable substituent in "heterocyclylene which may be substituted" of Q, the examples thereof include the groups described in (a) to (c), and (f) of the above-described Group G. In one embodiment, the examples thereof include $C_{1-6}$ alkyl which may be substituted with a group selected from the group consisting of —O—$C_{1-6}$ alkyl, —OH and halogen, —O—$C_{1-6}$ alkyl or halogen. In one embodiment, the examples thereof include $C_{1-6}$ alkyl which is substituted with —O—$C_{1-6}$ alkyl, and in one embodiment, methoxymethyl.

One embodiment of the compound of the formula (I) or a salt thereof will be described as follows.

(1) The compound of the formula (I) or a salt thereof in which X is C—H or N.

(1-1) The compound of the formula (I) or a salt thereof in which X is C—H.

(1-2) The compound of the formula (I) or a salt thereof in which X is N.

(2) The compound of the formula (I) or a salt thereof in which Y is C—$R^{3e}$ or N.

(2-1) The compound of the formula (I) or a salt thereof in which Y is C—$R^{3e}$.

(2-2) The compound of the formula (I) or a salt thereof in which Y is N.

(3) The compound of the formula (I) or a salt thereof in which $R^1$ and $R^2$ are the same as each other or are different from each other, and are $C_{1-6}$ alkyl which may be substituted, or $R^1$ and $R^2$ may be combined with the adjacent nitrogen atom to form cyclic amino which may be substituted.

(3-1) The compound of the formula (I) or a salt thereof in which
(i) $R^1$ and $R^2$ are the same as each other or are different from each other, and are $C_{1-6}$ alkyl which may be substituted with —O—$C_{1-6}$ alkyl or $C_{3-8}$ cycloalkyl, or
(ii) $R^1$ and $R^2$ are combined with the adjacent nitrogen atom to form cyclic amino which may be substituted, and the cyclic amino is azetidinyl, pyrrolidinyl, piperidinyl, or piperazinyl.

(3-2) The compound of the formula (I) or a salt thereof in which $R^1$ and $R^2$ are the same as each other or are different from each other, and are $C_{1-6}$ alkyl which may be substituted with —O—$C_{1-6}$ alkyl or $C_{3-8}$ cycloalkyl.

(3-3) The compound of the formula (I) or a salt thereof in which $R^1$ and $R^2$ are combined with the adjacent nitrogen atom to form cyclic amino which may be substituted, and the cyclic amino is azetidinyl, pyrrolidinyl, piperidinyl, or piperazinyl.

(3-4) The compound of the formula (I) or a salt thereof in which $R^1$ and $R^2$ are combined with the adjacent nitrogen atom to form cyclic amino which may be substituted with $C_{1-6}$ alkyl, —O—$C_{1-6}$ alkyl, or $C_{3-8}$ cycloalkyl, and the cyclic amino is azetidinyl, pyrrolidinyl, piperidinyl, or piperazinyl.

(3-5) The compound of the formula (I) or a salt thereof in which $R^1$ and $R^2$ are combined with the adjacent nitrogen atom to form pyrrolidine which is substituted with one or two $C_{1-6}$ alkyl.

(3-6) The compound of the formula (I) or a salt thereof in which $R^1$ and $R^2$ are combined with the adjacent nitrogen atom to form pyrrolidine which is substituted with one or two methyl.

(3-7) The compound of the formula (I) or a salt thereof in which $R^1$ and $R^2$ are combined with the adjacent nitrogen atom to form pyrrolidine which is substituted with one methyl.

(3-8) The compound of the formula (I) or a salt thereof in which $R^1$ and $R^2$ are combined with the adjacent nitrogen atom to form pyrrolidine which is substituted with two methyl.

(4) The compound of the formula (I) or a salt thereof in which $R^{3a}$, $R^{3b}$, $R^{3c}$, $R^{3d}$, and $R^{3e}$ are the same as each other or are different from each other, and are H, halogen, $C_{1-6}$ alkyl, halogeno $C_{1-6}$ alkyl, —O—$C_{1-6}$ alkyl, $C_{2-6}$ alkenyl, $C_{3-8}$ cycloalkyl, or —O-halogeno $C_{1-6}$ alkyl.

(4-A) The compound of the formula (I) or a salt thereof in which $R^{3a}$, $R^{3b}$, $R^{3c}$, and $R^{3d}$ are the same as each other or are different from each other, and are H, halogen, $C_{1-6}$ alkyl, halogeno $C_{1-6}$ alkyl, —O—$C_{1-6}$ alkyl, $C_{2-6}$ alkenyl, $C_{3-8}$ cycloalkyl, or —O-halogeno $C_{1-6}$ alkyl, and
in a case where Y is C—$R^{3e}$, $R^{3e}$ is H, halogen, $C_{1-6}$ alkyl, halogeno $C_{1-6}$ alkyl, —O—$C_{1-6}$ alkyl, $C_{2-6}$ alkenyl, $C_{3-8}$ cycloalkyl, or —O-halogeno $C_{1-6}$ alkyl.

(4-1) The compound of the formula (I) or a salt thereof in which Y is C—$R^{3e}$, $R^{3a}$, $R^{3c}$, $R^{3d}$ and $R^{3e}$ are the same as each other or are different from each other, and are H or halogen, and $R^{3b}$ is halogeno $C_{1-6}$ alkyl.

(4-2) The compound of the formula (I) or a salt thereof in which Y is C—$R^{3e}$, $R^{3a}$, $R^{3c}$, $R^{3d}$, and $R^{3e}$ are the same as each other or are different from each other, and are H or halogen, and $R^{3b}$ is trifluoromethyl.

(4-3) The compound of the formula (I) or a salt thereof in which Y is C—$R^{3e}$, $R^{3a}$ and $R^{3e}$ are the same as each other or are different from each other, and are H, fluoro, or chloro, $R^{3c}$ and $R^{3d}$ are H, and $R^{3b}$ is trifluoromethyl.

(4-4) The compound of the formula (I) or a salt thereof in which Y is C—$R^{3e}$, $R^{3a}$ is chloro, $R^{3b}$ is trifluoromethyl, and $R^{3c}$, $R^{3d}$, and $R^{3e}$ are H.

(4-5) The compound of the formula (I) or a salt thereof in which Y is C—$R^{3e}$, $R^{3a}$$R^{3c}$, and $R^{3d}$ are H, $R^{3b}$ is trifluoromethyl, and $R^{3e}$ is fluoro.

(5) The compound of the formula (I) or a salt thereof in which $R^4$ is H, halogen, or —O—$C_{1-6}$ alkyl.

(5-1) The compound of the formula (I) or a salt thereof in which $R^4$ is H or halogen.

(5-2) The compound of the formula (I) or a salt thereof in which $R^4$ is H or fluoro.

(5-3) The compound of the formula (I) or a salt thereof in which $R^4$ is H.

(5-4) The compound of the formula (I) or a salt thereof in which $R^4$ is fluoro.

(6) The compound of the formula (I) or a salt thereof in which $R^5$ is H, $C_{1-6}$ alkyl, or —$NR^{51}R^{52}$ and $R^{51}$ and $R^{52}$ are the same as each other or are different from each other, and are H or $C_{1-6}$ alkyl.

(6-1) The compound of the formula (I) or a salt thereof in which $R^5$ is H, $C_{1-6}$ alkyl, or —$NR^{51}R^{52}$, and $R^{51}$ and $R^{52}$ are the same as each other or are different from each other, and are $C_{1-6}$ alkyl.

(6-2) The compound of the formula (I) or a salt thereof in which $R^5$ is H or $C_{1-6}$ alkyl.

(6-3) The compound of the formula (I) or a salt thereof in which $R^5$ is H or methyl.

(6-4) The compound of the formula (I) or a salt thereof in which $R^5$ is H.

(6-5) The compound of the formula (I) or a salt thereof in which $R^5$ is methyl.

(7) The compound of the formula (I) or a salt thereof in which Q is heterocyclylene which may be substituted.

(7-1) The compound of the formula (I) or a salt thereof in which Q is heterocyclylene which may be substituted, and the heterocyclylene is pyrrolidine-diyl, piperidine-diyl, or piperazine-diyl.

(7-1-A) The compound of the formula (I) or a salt thereof in which Q is heterocyclylene which may be substituted, and the heterocyclylene is pyrrolidine-1,3-diyl, piperidine-1,4-diyl, or piperazine-1,4-diyl.

(7-2) The compound of the formula (I) or a salt thereof in which Q is heterocyclylene which may be substituted with $C_{1-6}$ alkyl which may be substituted with a group selected from the group consisting of —O—$C_{1-6}$ alkyl, —OH and halogen, —O—$C_{1-6}$ alkyl or halogen, and the heterocyclylene is piperidine-diyl or piperazine-diyl.

(7-3) The compound of the formula (I) or a salt thereof in which Q is heterocyclylene which may be substituted with —$C_{1-6}$ alkylene-O—$C_{1-6}$ alkyl, and the heterocyclylene is piperidine-diyl or piperazine-diyl.

(7-3-A) The compound of the formula (I) or a salt thereof in which Q is heterocyclylene which may be substituted with —$C_{1-6}$ alkylene-O—$C_{1-6}$ alkyl, and the heterocyclylene is piperidine-1,4-diyl or piperazine-1,4-diyl.

(7-4) The compound of the formula (I) or a salt thereof in which Q is heterocyclylene which may be substituted with methoxymethyl, and the heterocyclylene is piperidine-diyl or piperazine-diyl.

(7-4-A) The compound of the formula (I) or a salt thereof in which Q is heterocyclylene which may be substituted with methoxymethyl, and the heterocyclylene is piperidine-1,4-diyl or piperazine-1,4-diyl.

(7-5) The compound of the formula (I) or a salt thereof in which Q is i) piperidine-1,4-diyl, or ii) piperazine-1,4-diyl which may be substituted with methoxymethyl.

(7-6) The compound of the formula (I) or a salt thereof in which Q is piperidine-1,4-diyl.

(7-7) The compound of the formula (I) or a salt thereof in which Q is piperazine-1,4-diyl which may be substituted with methoxymethyl.

(8) The compound of the formula (1) or a salt thereof in which W is a bond, $C_{1-6}$ alkylene, —O—$C_{1-6}$ alkylene, or —$N(R^N)$—$C_{1-6}$ alkylene, and $R^N$ is H or $C_{1-6}$ alkyl.

(8-1) The compound of the formula (I) or a salt thereof in which W is a bond, $C_{1-6}$ alkylene, —O—$C_{1-6}$ alkylene, or —$N(R^N)$—$C_{1-6}$ alkylene, and $R^N$ is $C_{1-6}$ alkyl.

(8-2) The compound of the formula (I) or a salt thereof in which W is $C_{1-6}$ alkylene or —O—$C_{1-6}$ alkylene.

(8-3) The compound of the formula (I) or a salt thereof in which W is —$CH_2$—$CH_2$— or —O—$CH_2$—.

(8-4) The compound of the formula (I) or a salt thereof in which W is —$CH_2$—$CH_2$—.

(8-5) The compound of the formula (I) or a salt thereof in which W is —O—$CH_2$—.

(9) The compound of the formula (I) or a salt thereof in which n is 0 or 1.

(9-1) The compound of the formula (I) or a salt thereof in which n is 0.

(9-2) The compound of the formula (I) or a salt thereof in which n is 1.

(10) The compound of the formula (I) or a salt thereof, which is a combination of any two or more of the groups, which are not inconsistent with each other, among some embodiments of each group described in (1) to (9-2) above. Examples thereof include the compounds or salts thereof shown below.

(10-1) The compound of the formula (I) or a salt thereof in which
X is as described in (1) above,
Y is as described in (2) above,
$R^1$ and $R^2$ are as described in (3-1) above,
$R^{3a}$, $R^{3b}$, $R^{3c}$, $R^{3d}$ and $R^{3e}$ are as described in (4) above,
$R^4$ is as described in (5) above,
$R^5$ is as described in (6) above,
Q is as described in (7-1) above,
W is as described in (8-1) above, and
n is as described in (9) above.

(10-1-A) The compound of the formula (I) or a salt thereof in which
X is as described in (1) above,
Y is as described in (2) above,
$R^1$ and $R^2$ are as described in (3-1) above,
$R^{3a}$, $R^{3b}$, $R^{3c}$, $R^{3d}$, and $R^{3e}$ are as described in (4-A) above,
$R^4$ is as described in (5) above,
$R^5$ is as described in (6) above,
Q is as described in (7-1-A) above,
W is as described in (8-1) above, and
n is as described in (9) above.

(10-2) The compound of the formula (I) or a salt thereof in which
X is as described in (1-2) above,
Y is as described in (2-1) above,
$R^1$ and $R^2$ are as described in (3-4) above,
$R^{3a}$, $R^{3b}$, $R^{3c}$, $R^{3d}$, and $R^{3e}$ are as described in (4-1) above,
$R^4$ is as described in (5-1) above,
$R^5$ is as described in (6-2) above,
Q is as described in (7-3) above,
W is as described in (8-2) above, and
n is as described in (9-2) above.

(10-2-A) The compound of the formula (I) or a salt thereof in which
X is as described in (1-2) above,
Y is as described in (2-1) above,
$R^1$ and $R^2$ are as described in (3-4) above
$R^{3a}$, $R^{3b}$, $R^{3c}$, $R^{3d}$, and $R^{3e}$ are as described in (4-1) above,
$R^4$ is as described in (5-1) above,
$R^5$ is as described in (6-2) above,
Q is as described in (7-3-A) above,
W is as described in (8-2) above, and
n is as described in (9-2) above.

(10-3) The compound of the formula (I) described in (10-2) or a salt thereof in which R$^1$ and R$^2$ are as described in (3-5) above, R$^{3a}$, R$^{3b}$, R$^{3c}$, R$^{3d}$, and R$^{3e}$ are as described in (4-2) above, and W is as described in (8-3) above.

(10-3-A)

The compound of the formula (I) described in (10-2-A) or a salt thereof in which R$^1$ and R$^2$ are as described in (3-5) above, R$^{3a}$, R$^{3b}$, R$^{3c}$, R$^{3d}$, and R$^{3e}$ are as described in (4-2) above, and W is as described in (8-3) above.

Examples of the specific compounds of the formula (I) include the following compounds or salts thereof:

3-(4-{6-[(5-{[(2R,5R)-2,5-dimethylpyrrolidin-1-yl]methyl}-4-[3-fluoro-5-(trifluoromethyl)phenyl]-1,3-thiazol-2-yl)amino]-5-fluoropyrimidin-4-yl}piperazin-1-yl)propanoic acid, 3-(4-{6-[(5-{[(2R,5R)-2,5-dimethylpyrrolidin-1-yl]methyl}-4-[3-fluoro-5-(trifluoromethyl)phenyl]-1,3-thiazol-2-yl)amino]-5-fluoro-2-methylpyrimidin-4-yl}piperazin-1-yl)propanoic acid, 3-(4-{6-[(4-[4-chloro-3-(trifluoromethyl)phenyl]-5-{[(2R)-2-methylpyrrolidin-1-yl]methyl-1,3}-thiazol-2-yl)amino]-5-fluoropyrimidin-4-yl}piperazin-1-yl)propanoic acid, 3-[(2S)-4-{5-fluoro-6-[(4-[3-fluoro-5-(trifluoromethyl)phenyl]-5-{[(2R)-2-methylpyrrolidin-1-yl]methyl}-1,3-thiazol-2-yl)amino]pyrimidin-4-yl}-2-(methoxymethyl)piperazin-1-yl]propanoic acid),

[(1-{5-fluoro-6-[(4-[3-fluoro-5-(trifluoromethyl)phenyl]-5-{[(2R)-2-methylpyrrolidin-1-yl]methyl}-1,3-thiazol-2-yl)amino]pyrimidin-4-yl}piperidin-4-yl) oxy]acetic acid, 3-[(2S)-4-{6-[(4-[4-chloro-3-(trifluoromethyl)phenyl]-5-{[(2R)-2-methylpyrrolidin-1-yl]methyl}-1,3-thiazol-2-yl)amino]-5-fluoropyrimidin-4-yl}-2-(methoxymethyl)piperazin-1-yl]propanoic acid,

[(1-{6-[(4-[3-chloro-5-(trifluoromethyl)phenyl]-5-{[(2R)-2-ethylpyrrolidin-1-yl]methyl}-1,3-thiazol-2-yl)amino]-5-fluoropyrimidin-4-yl}piperidin-4-yl)oxy]acetic acid, 3-(4-{6-[(4-[3-chloro-5-(trifluoromethyl)phenyl]-5-{[(2R)-2-methylpyrrolidin-1-yl]methyl}-1,3-thiazol-2-yl)amino]-5-fluoropyrimidin-4-yl}piperazin-1-yl)propanoic acid, 3-(4-{6-[(4-[3-fluoro-5-(trifluoromethyl)phenyl]-5-{[(2R)-2-methylpyrrolidin-1-yl]methyl}-1,3-thiazol-2-yl)amino]-2-methylpyrimidin-4-yl}piperazin-1-yl)propanoic acid, 3-(4-{5-fluoro-6-[(4-[3-fluoro-5-(trifluoromethyl)phenyl]-5-{[(2R)-2-methylpyrrolidin-1-yl]methyl}-1,3-thiazol-2-yl)amino]pyrimidin-4-yl}piperazin-1-yl)propanoic acid, and 3-(4-{5-fluoro-6-[(4-[3-fluoro-5-(trifluoromethyl)phenyl]-5-{[(2R)-2-methylpyrrolidin-1-yl]methyl}-1,3-thiazol-2-yl)amino]-2-methylpyrimidin-4-yl}piperazin-1-yl)propanoic acid.

In another embodiment, examples of the specific compounds of the formula (I) include the following compounds or salts thereof:

3-(4-{6-[(4-[3-fluoro-5-(trifluoromethyl)phenyl]-5-{[(2R)-2-methylpyrrolidin-1-yl]methyl}-1,3-thiazol-2-yl)amino]pyrimidin-4-yl}piperazin-1-yl)propanoic acid, 3-(4-{2-[(4-[3-fluoro-5-(trifluoromethyl)phenyl]-5-{[(2R)-2-methylpyrrolidin-1-yl]methyl}-1,3-thiazol-2-yl)amino]pyridin-4-yl}piperazin-1-yl)propanoic acid, 3-(4-{6-[(4-[3-fluoro-5-(trifluoromethyl)phenyl]-5-{[(2R)-2-methylpyrrolidin-1-yl]methyl}-1,3-thiazol-2-yl)amino]-5-methoxypyrimidin-4-yl}piperazin-1-yl)propanoic acid, 3-(4-{3-fluoro-2-[(4-[3-fluoro-5-(trifluoromethyl)phenyl]-5-{[(2R)-2-methylpyrrolidin-1-yl]methyl}-1,3-thiazol-2-yl)amino]pyridin-4-yl}piperazin-1-yl)propanoic acid, 3-{4-[6-({4-[3-fluoro-5-(trifluoromethyl)phenyl]-5-[isopropyl(2-methoxyethyl)amino]-1,3-thiazol-2-yl}amino)-2-methyl pyrimidin-4-yl]piperazin-1-yl}propanoic acid, 3-{4-[6-({4-[4-chloro-3-(trifluoromethyl)phenyl]-5-[(3 S)-3-methoxypiperidin-1-yl]-1,3-thiazol-2-yl}amino)-5-fluoropyrimidin-4-yl]piperazin-1-yl}propanoic acid, N-[(3 S)-1-{5-fluoro-6-[(4-[3-fluoro-5-(trifluoromethyl)phenyl]-5-{[(2R)-2-methylpyrrolidin-1-yl]methyl}-1,3-thiazol-2-yl)amino]pyrimidin-4-yl}pyrrolidin-3-yl]-N-methyl-β-alanine, 1-{5-fluoro-6-[(4-[3-fluoro-5-(trifluoromethyl)phenyl]-5-{[(2R)-2-methyl pyrrolidin-1-yl]methyl}-1,3-thiazol-2-yl)amino]pyrimidin-4-yl}-4-methoxypiperidine-4-carboxylic acid, 3-[4-(5-fluoro-6-[(4-[3-fluoro-5-(trifluoromethyl)phenyl]-5-{[(2R)-2-methylpyrrolidin-1-yl]methyl}-1,3-thiazol-2-yl)amino]pyrimidin-4-yl}-2-(fluoromethyl)piperazin-1-yl]propanoic acid, 3-(4-{6-[(4-[3-chloro-5-(trifluoromethoxy)phenyl]-5-{[(2R)-2-methylpyrrolidin-1-yl]methyl}-1,3-thiazol-2-yl)amino]-5-fluoropyrimidin-4-yl}piperazin-1-yl)propanoic acid, 3-[(2S)-4-{6-[(4-[4-chloro-3-(trifluoromethyl)phenyl]-5-{[(2R)-2-methylpyrrolidin-1-yl]methyl}-1,3-thiazol-2-yl)amino]-5-fluoropyrimidin-4-yl}-2-(fluoromethyl)piperazin-1-yl]propanoic acid, (4-{6-[(4-[3-chloro-5-(trifluoromethyl)phenyl]-5-{[(2R)-2-methylpyrrolidin-1-yl]methyl}-1,3-thiazol-2-yl)amino]-5-fluoropyrimidin-4-yl}piperazin-1-yl)acetic acid, 3-(1-{6-[(4-[3-fluoro-5-(trifluoromethyl)phenyl]-5-{[(2R)-2-methylpyrrolidin-1-yl]methyl}-1,3-thiazol-2-yl)amino]-2-methylpyrimidin-4-yl}piperidin-4-yl)propanoic acid, 3-(4-{2-(dimethylamino)-6-[(4-[3-fluoro-5-(trifluoromethyl)phenyl]-5-{[(2R)-2-methylpyrrolidin-1-yl]methyl}-1,3-thiazol-2-yl)amino]pyrimidin-4-yl}piperazin-1-yl)propanoic acid, 3-{[(3R)-1-{6-[(4-[3-fluoro-5-(trifluoromethyl)phenyl]-5-{[(2R)-2-methylpyrrolidin-1-yl]methyl}-1,3-thiazol-2-yl)amino]-2-methylpyrimidin-4-yl}pyrrolidin-3-yl]oxy}propanoic acid, 3-{4-[6-({5-(4-cyclopropylpiperazin-1-yl)-4-[3-fluoro-5-(trifluoromethyl)phenyl]-1,3-thiazol-2-yl}amino)-5-fluoropyrimidin-4-yl]piperazin-1-yl}propanoic acid, and 3-(4-{5-fluoro-6-[(4-[6-methoxy-5-(trifluoromethyl)pyridin-3-yl]-5-{[(2R)-2-methylpyrrolidin-1-yl]methyl}-1,3-thiazol-2-yl)amino]pyrimidin-4-yl}piperazin-1-yl)propanoic acid.

With regard to the compound of the formula (I), tautomers or geometrical isomers thereof may exist, depending on the kinds of the substituents. In the present specification, the compound of the formula (I) may be described in only one form of isomers in some cases, but the present invention includes other isomers, isolated forms of the isomers, or a mixture thereof.

Furthermore, some of the compounds of the formula (I) may have asymmetric carbon atoms or axis chirality in some cases, and correspondingly, the optical isomers or diastereomers thereof can exist. The present invention includes the isolated form of the optical isomer of the compound of the formula (I) or a mixture thereof.

In addition, a pharmaceutically acceptable prodrug of the compound represented by the formula (I) is also included in the present invention. The pharmaceutically acceptable prodrug refers to a compound having a group which can be converted into an amino group, a hydroxyl group, a carboxyl group, or the like, by solvolysis or under a physiological condition. Examples of the groups forming the prodrug include those as described in Prog. Med., 5, 2157-2161 (1985) or "Pharmaceutical Research and Development" (Hirokawa Publishing Company, 1990), vol. 7, Molecular Design, 163-198, and "Methods and Principles in Medicinal Chemistry, vol. 47, Prodrugs and Targeted Delivery (Wiley-VCH, 2010)".

Moreover, the salt of the compound of the formula (1) is a pharmaceutically acceptable salt of the compound of the formula (I), and the compounds of the formula (I) may form an acid addition salt or a salt with a base, depending on the kinds of the substituents in some cases. Specifically, examples thereof include acid addition salts with inorganic acids such as hydrochloric acid, hydrobromic acid, hydroiodic acid, sulfuric acid, nitric acid, and phosphoric acid, and with organic acids such as formic acid, acetic acid, propanoic acid, oxalic acid, malonic acid, succinic acid, fumaric acid, maleic acid, lactic acid, malic acid, mandelic acid, tartaric acid, dibenzoyl tartaric acid, ditoluoyl tartaric acid, citric acid, methanesulfonic acid, ethanesulfonic acid, benzenesulfonic acid, p-toluenesulfonic acid, aspartic acid, and glutamic acid, and salts with metal cations such as sodium, potassium, magnesium, calcium, and aluminum, and with organic bases such as methylamine, ethylamine, ethanolamine, lysine, ornithine, and salts with various amino acids or derivatives of amino acids such as acetyl leucine, lysine, and ornithine, ammonium salts, and others.

In addition, the present invention also includes various hydrates or solvates, and crystal polymorph substances of the compound of the formula (I) and a salt thereof. In addition, the present invention also includes the compounds labeled with various radioactive or non-radioactive isotopes.

(Production Process)

The compound of the formula (I) or a salt thereof can be prepared by applying various known synthetic methods, using the characteristics based on their basic structures or the kinds of the substituents. At this time, depending on the types of the functional groups, it is in some cases effective from the viewpoint of the preparation techniques to protect the functional group with an appropriate protective group (a group which is capable of being easily converted into the functional group), during the steps from starting materials to intermediates. Examples of the protective group include the protective groups as described in "Greene's Protective Groups in Organic Synthesis (4th edition, 2006)", edited by P. G. M. Wuts and T. W. Greene, and the like, which may be appropriately selected and used depending on the reaction conditions. In these methods, a desired compound can be obtained by introducing the protective group to carry out the reaction, and then, if desired, removing the protective group.

In addition, the prodrug of the compound of the formula (I) can be prepared by introducing a specific group during the steps from starting materials to intermediates, in the same manner as for the above protective groups, or by further carrying out the reaction using the obtained compound of the formula (I). The reaction can be carried out by applying a method known to a person skilled in the art, such as common esterification, amidation, and dehydration.

Hereinbelow, typical preparation methods of the compound of the formula (I) will be described. Each of the production processes can also be carried out with reference to the documents appended to the description herein. Further, the preparation methods of the present invention are not limited to the examples as shown below.

(Production Process 1)

[Chem. 6]

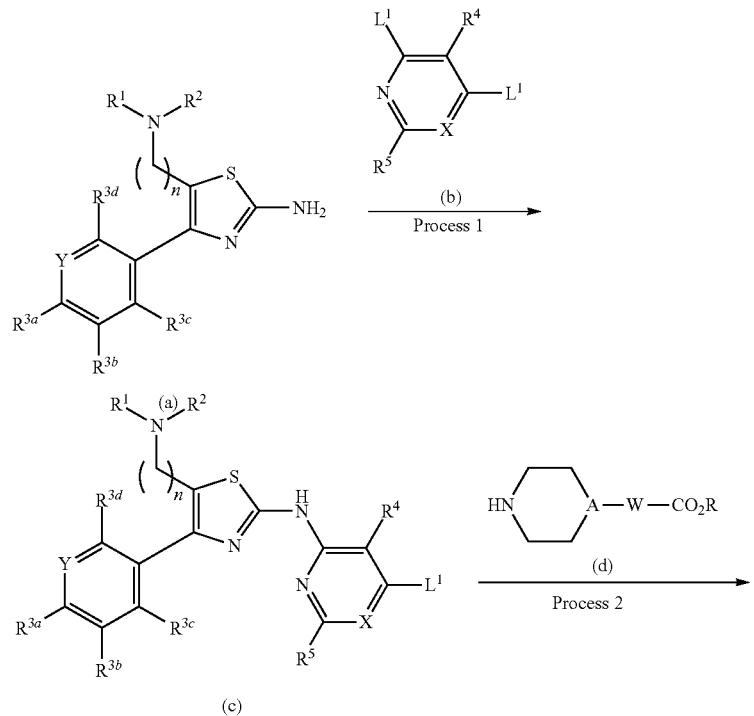

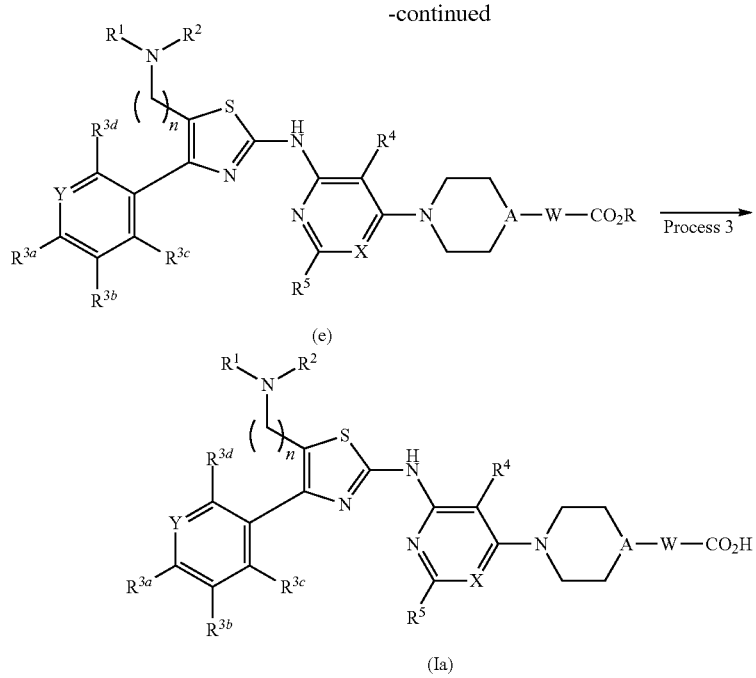

(in which, R represents $C_{1-6}$ alkyl or benzyl, $L^1$ represents a leaving group, A represents N or CH, which shall apply hereinafter).

This production process is a method for producing a compound of the formula (Ia) in which Q is piperazine-1,4-diyl or piperidine-1,4-diyl among the compounds of the formula (I) which are the compounds of the present invention, from the compound of the formula (a).

(Process 1)

This step is a step of obtaining a compound of the formula (c) by reacting a compound of the formula (a) with the compound of the formula (b). Here, examples of the leaving group $L^1$ include a halogen group, a methanesulfonyloxy group, and a p-toluenesulfonyloxy group.

This reaction is carried out using the compound of the formula (a) and the compound of the formula (b), by stirring the mixture under the temperature condition ranging from under cooling to under heating to reflux, preferably at 0° C. to 90° C., usually for 0.1 hours to 5 days, in a solvent which is inert to the reaction or without a solvent. Examples of the solvent used herein are not particularly limited, but include aromatic hydrocarbons such as benzene, toluene and xylene, ethers such as diethyl ether, tetrahydrofuran (THF), dioxane, 1,2-dimethoxyethane, and the like, halogenated hydrocarbons such as methylene chloride, 1,2-dichloroethane, chloroform, and the like, N,N-dimethylformamide (DMF), dimethylsulfoxide (DMSO), ethyl acetate, acetonitrile, 1-methylpyrrolidin-2-one (NMP), and a mixture thereof. It may be advantageous in some cases for the smooth progress of the reaction to carry out the reaction in the presence of an organic base such as triethylamine, N,N-diisopropylethylamine, N-methylmorpholine, and the like or an inorganic base such as sodium hydride, potassium carbonate, sodium carbonate, potassium hydroxide, and the like.

REFERENCES

"Organic Functional Group Preparations" written by S. R. Sandler and W. Karo, 2$^{nd}$ edition, Vol. 1, Academic Press Inc., 1991

"Courses in Experimental Chemistry (5$^{th}$ edition)" edited by The Chemical Society of Japan, Vol. 14 (2005) (Maruzen).

(Process 2)

This step is a step of obtaining a compound of the formula (e) by reacting the compound of the formula (c) with a compound of the formula (d). The reaction conditions are the same as in Process 1 of Production Process 1. In addition, it is possible to switch the order of Process 1 and Process 2.

(Process 3)

This step is a step of obtaining a compound of formula (Ia) by deprotecting the compound of the formula (e).

This reaction is carried out by using the compound of the formula (e) and a deprotecting reagent by stirring the mixture under the temperature condition ranging from under cooling to heating to reflux, usually for 0.1 hours to 5 days, in a solvent which is inert to the reaction or without a solvent. In the case where R is benzyl, this reaction can also be carried out by subjecting the compound of the formula (e) to a hydrogenation reaction using a metal catalyst in a hydrogen atmosphere. Examples of the solvent used herein are not particularly limited, but include alcohols such as methanol, ethanol, n-propanol and the like, DMF, THF, and the like. Further, there are some cases where a mixed solvent of the solvent and water is highly suitable for the reaction. Examples of the deprotecting reagent are not particularly limited, but include bases such as an aqueous sodium hydroxide solution, an aqueous potassium hydroxide solution and the like, and acids such as hydrochloric acid, trifluoroacetic acid and the like. In addition, examples of the metal catalyst that can be used in the hydrogenation reaction include palladium on carbon and palladium hydroxide.

(Production Process 2)

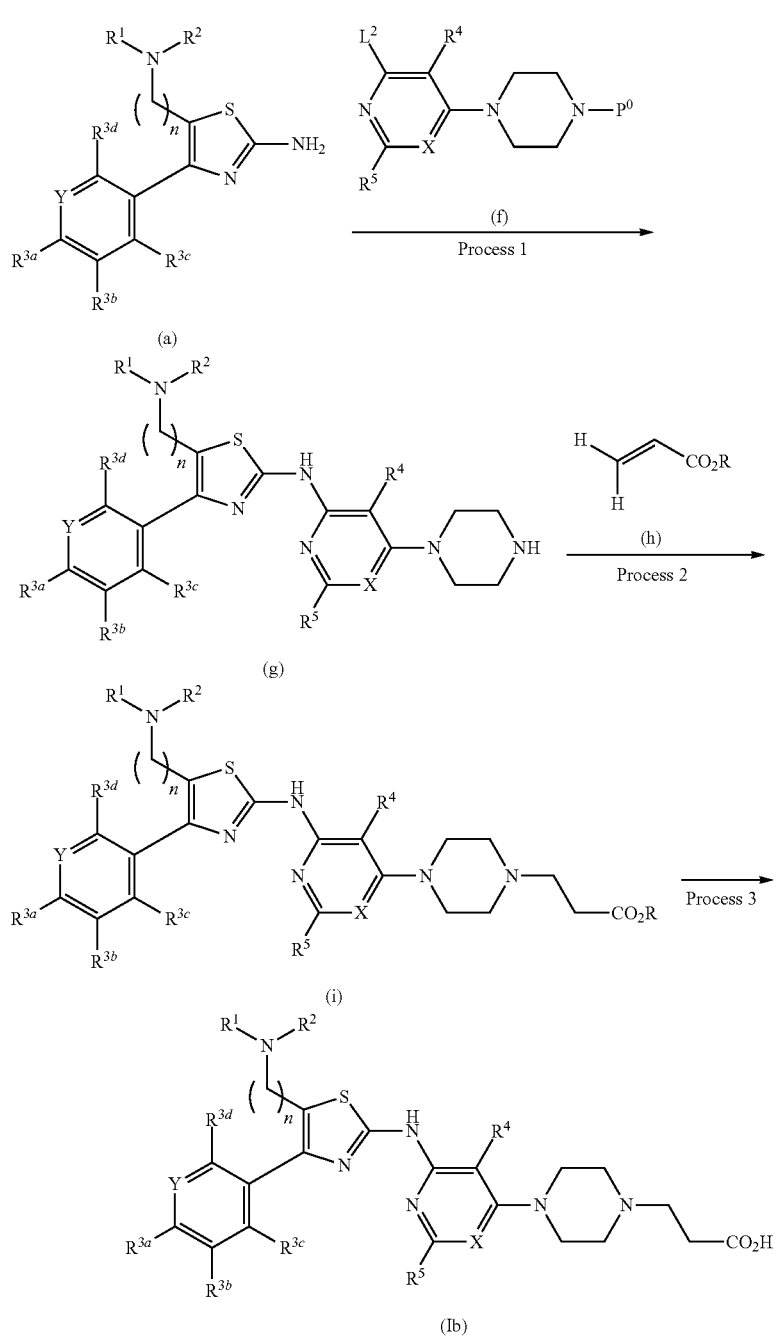

(in which, $L^2$ represents a leaving group, and $P^0$ represents a protecting group, which shall apply hereinafter).

This production process is a method for producing a compound of the compound of the formula (Ib) in which W is ethylene, and Q is piperazine-1,4-diyl among the compounds of the formula (I) which are the compounds of the present invention, from the compound of the formula (a).

(Process 1)

This step is a step of obtaining a compound of the formula (g) by a deprotecting after reacting a compound of the formula (a) with a compound of the formula (f). Here, examples of a leaving group $L^2$ include a halogen, a trifluoromethanesulfonyloxy group, and the like. In addition, examples of a protecting group $P^0$ include a t-butoxycarbonyl (Boc), and the like.

The reaction is carried out by using the compound of the formula (a) and the compound of the formula (f) in equivalent amounts, or either thereof in an excess amount, by stirring the mixture under the temperature condition ranging from under cooling to under heating, preferably at room temperature to 150° C., usually for 0.1 hours to 5 days, in a solvent which is inert to the reaction, in the presence of a palladium catalyst, a ligand, and a base. Examples of the solvent used herein are not particularly limited, but include aromatic hydrocarbons such as benzene, toluene, xylene and the like, N,N-dimethylformamide, acetonitrile, water, and a mixture thereof. Examples of the palladium catalyst include palladium acetate or tris(dibenzylideneacetone) dipalladium, and the like. In addition, examples of the ligand include 1,1'-bis(diphenylphosphino)ferrocene (dppf), 1,1'-binaphthalene-2,2'-diyl bis(diphenylphosphine) (BINAP), 2-dicyclohexylphosphino-2',4',6'-triisopropylbiphenyl (XPhos), dicyclohexyl(2',6'-dimethoxybiphenyl-2-yl)phosphine (SPhos), tricyclohexylphosphine, di-tert-butyl(2',4',6'-triisopropylbiphenyl-2-yl)phosphine, (9,9-dimethyl-9H-xanthene-4,5-diyl) bis(diphenylphosphine), and the like. Further, examples of the base include sodium tert-butoxide, lithium hexamethyldisilazide, potassium phosphate, and the like.

In addition, deprotecting the $P^0$ group can be carried out by referring "Protective Groups in Organic Synthesis" written by Wuts and Greene, 4th edition, John Wiley & Sons Inc., 2006".

REFERENCES

Wolfe, J. P.; Wagaw, S.; Marcoux, J. F.; Buchwald, S. L. Acc. Chem. Res. 1998, 31, 805
Harwig, J. F. Ace. Chem. Res. 1998, 31, 852.

(Process 2)

This step is a step of preparing a compound of the formula (i) by reacting the compound of the formula (g) with a compound of the formula (h).

This reaction is carried out using the compound of the formula (g) and the compound of the formula (h) in equivalent amounts, or either thereof in an excess amount, by stirring the mixture under the temperature condition ranging from under cooling to under heating to reflux, preferably at 0° C. to 100° C., usually for 0.1 hours to 5 days, in a solvent which is inert to the reaction. Examples of the solvent used herein are not particularly limited, but include aromatic hydrocarbons such as benzene, toluene, xylene and the like, ethers such as diethyl ether, tetrahydrofuran, dioxane, 1,2-dimethoxyethane and the like, halogenated hydrocarbons such as methylene chloride, 1,2-dichloroethane, chloroform and the like, DMF, NMP, DMSO, ethyl acetate, acetonitrile, ethanol, and a mixture thereof. It may be advantageous in some cases for the smooth progress of the reaction to carry out the reaction in the presence of an organic base such as piperidine, triethylamine, N,N-diisopropylethylamine, N-methylmorpholine and the like, or an inorganic base such as potassium carbonate, sodium carbonate, potassium hydroxide and the like.

REFERENCES

"Courses in Experimental Chemistry (5$^{th}$ edition)" edited by The Chemical Society of Japan, Vol. 16 (2005) (Maruzen).

(Process 3)

This step is a step of obtaining a compound of formula (Ib) by deprotecting the compound of the formula (i). The reaction conditions are the same as in Process 3 of Production Process 1.

(Production Process 3)

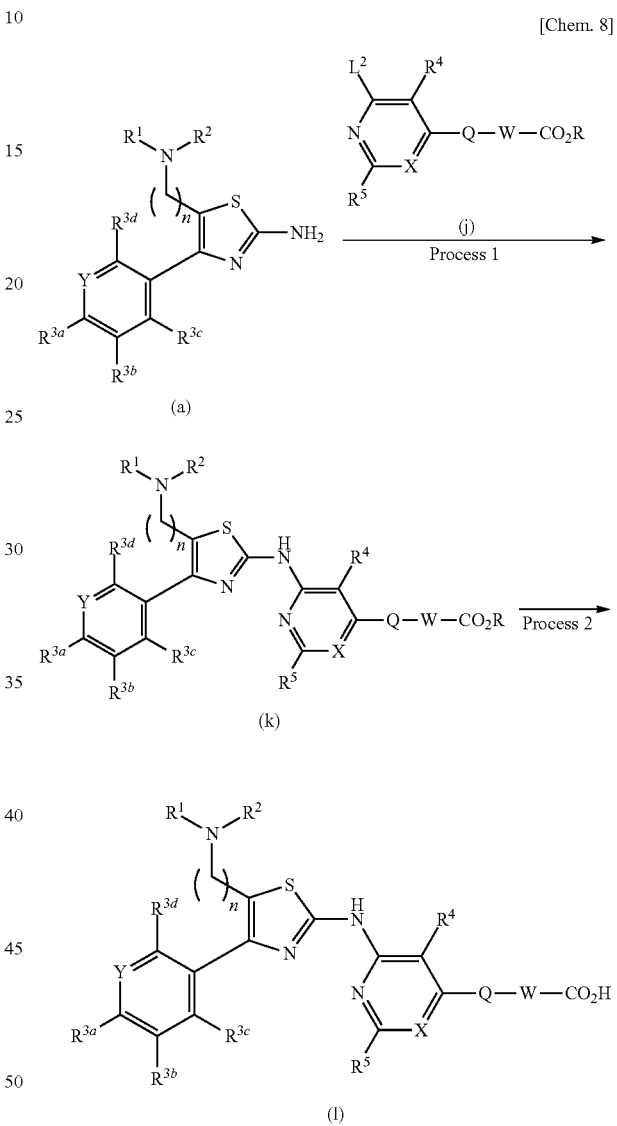

This production process is another preparation method for the compound of the formula (I).

(Process 1)

This step is a step of preparing a compound of the formula (k) by reacting a compound of the formula (a) with a compound of the formula (j). The reaction conditions are the same as in Process 1 of Production Process 2.

(Process 2)

This step is a step of obtaining a compound of formula (I) by deprotecting the compound of the formula (k). The reaction conditions are the same as in Process 3 of Production Process 1.

(Production Process 4)
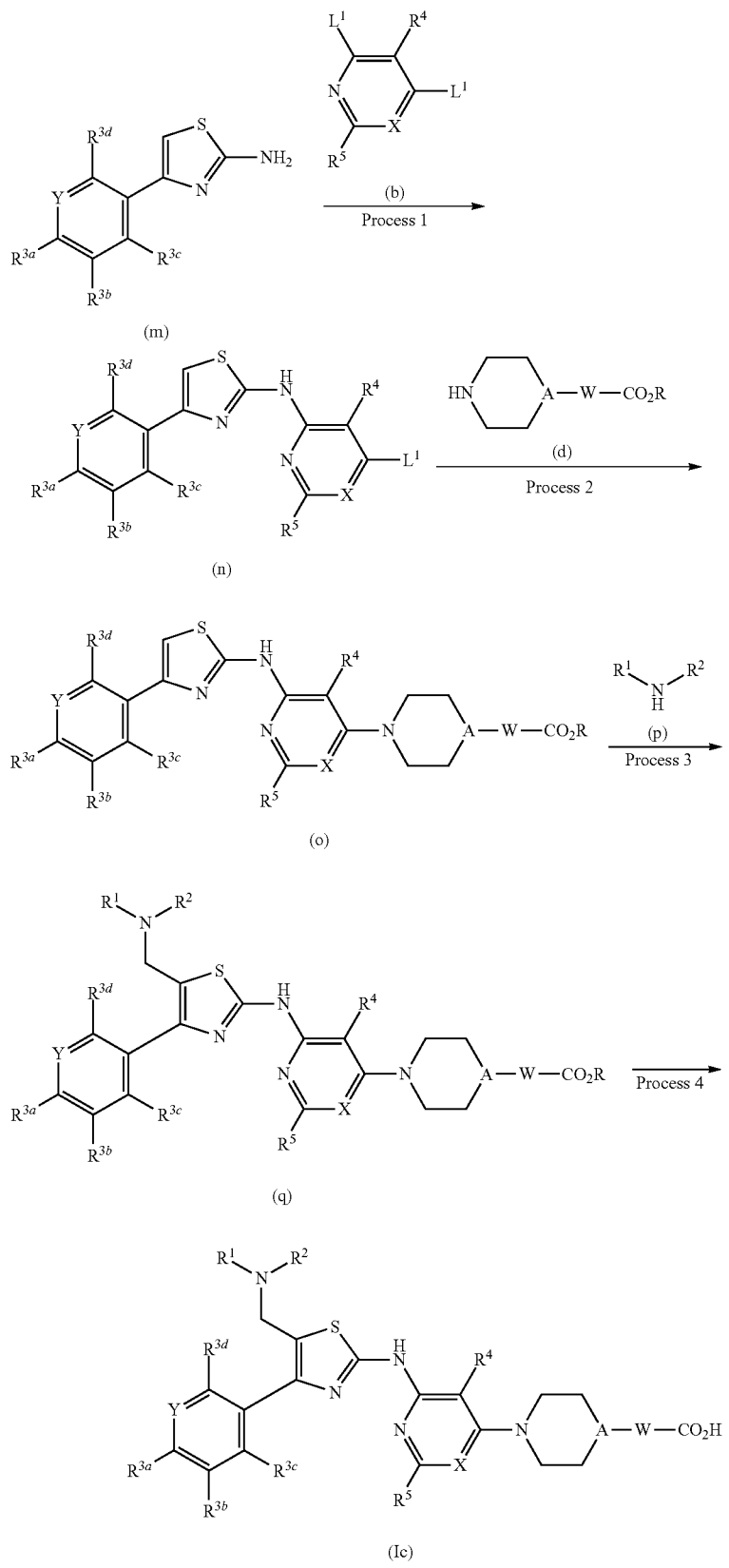

This production process is a method for producing a compound of the formula (Ic) in which Q is piperazine-1,4-diyl or piperidine-1,4-diyl, and n is 1 among the compounds of the formula (I).

(Process 1)

This step is a step of obtaining a compound of the formula (n) by reacting a compound of the formula (m) with the compound of the formula (b). The reaction conditions are the same as in Process 1 of Production Process 1.

(Process 2)

This step is a step of obtaining a compound of the formula (o) by reacting the compound of the formula (n) with a compound of the formula (d). The reaction conditions are the same as in Process 1 of Production Process 1.

(Process 3)

This step is a step of obtaining a compound of the formula (q) by subjecting the compound of the formula (o) to a Mannich reaction by using a compound of the formula (p) and formaldehyde. It is possible to employ a method described in Journal of the American Chemical Society written by Albertson, N. F. 1948, 70, 669 and Bulletin of the Chemical Society of Japan written by Bhargava, P. N., Sharma, S. C. 1965, 38, 909, or a method similar to that.

(Process 4)

This step is a step of preparing a compound of formula (Ic) by deprotecting the compound of the formula (q). The reaction conditions are the same as in Process 3 of Production Process 1.

(Synthesis of Starting Materials)

[Chem. 10]

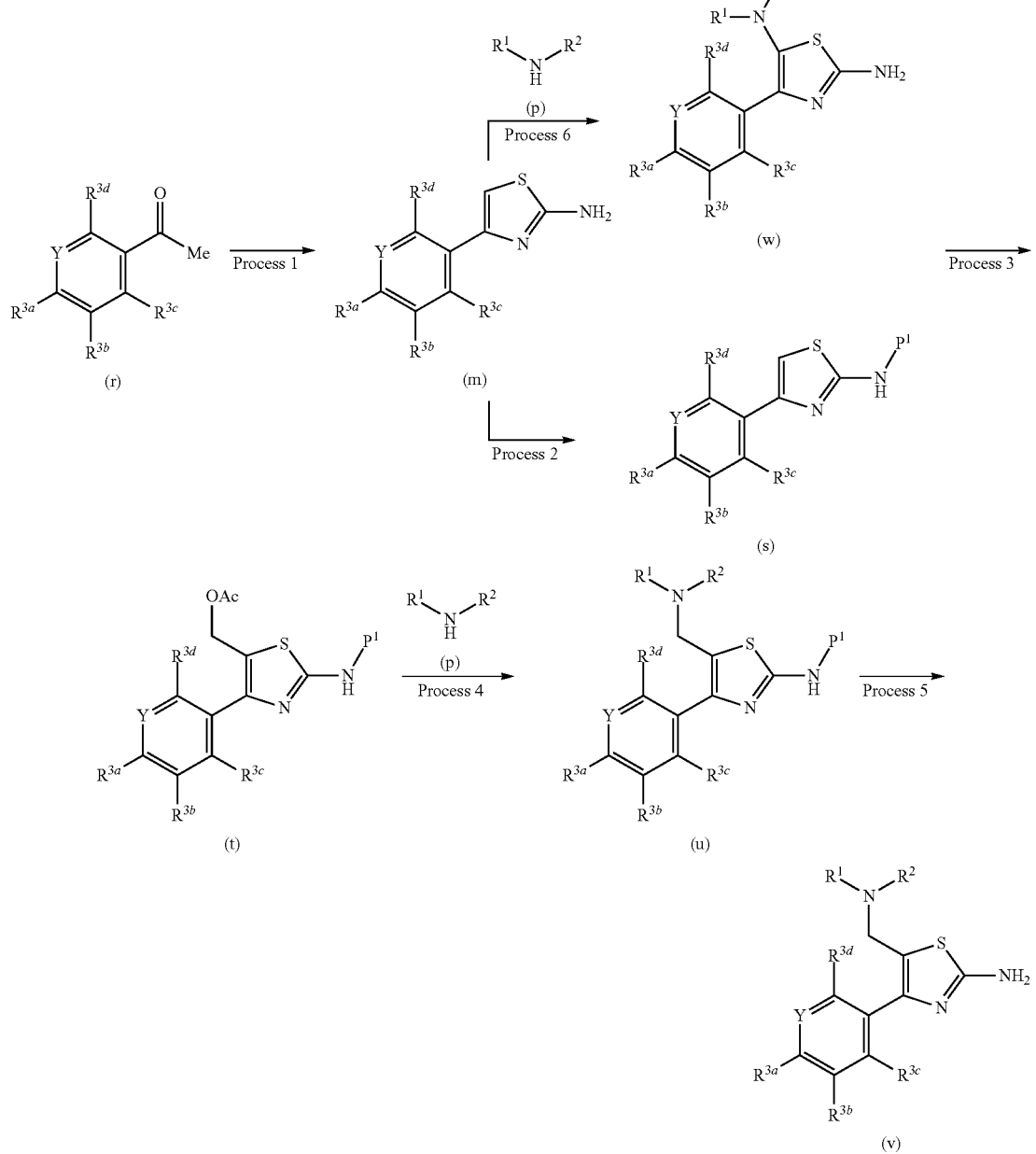

(in which, Me represents methyl, Ac represents acetyl, and P¹ represents a protecting group).

This production process is a method for producing a compound of the formula (v) in which n=1, a compound of the formula (w) in which n=0 among the compounds of the formula (a) which are starting materials in the above-described Production Processes 1 to 3, and the compound of the formula (m) which is a starting material of Production Process 4. Here, examples of the protecting group P¹ include the protecting groups of the amino groups described in "Protective Groups in Organic Synthesis" written by Wuts and Greene, 4th edition, John Wiley & Sons Inc., 2006, such as an acetyl group.

(Process 1)

This step is a step of obtaining a compound of the formula (m) having 2-aminothiazole from a compound of the formula (r). It is possible to obtain the compound of the formula (m) having 2-aminothiazole by reacting the compound of the formula (r) with a brominating agent such as trimethylphenylammonium tribromide, and then reacting with thiourea in a solvent which is inert to the reaction. It is possible to employ a method described in Journal of the American Chemical Society written by Dodson R. M. et al., 1945, 67, 2242, or a method similar to that.

(Process 2)

This step is a step of protecting the amino group of the compound of the formula (m). Here, the present reaction can be carried out with reference to "Protective Groups in Organic Synthesis" written by Wuts and Greene, 4$^{th}$ edition, John Wiley & Sons Inc., 2006.

(Process 3)

This step is a step of preparing a compound of the formula (t) by introducing an acetoxymethyl group into the 5-position of thiazole in a compound of the formula (s). The step can be carried out by reacting a formaldehyde aqueous solution or a paraformaldehyde with a compound of the formula (s) in the presence of an acetic acid solvent under the temperature condition ranging from at room temperature to under heating, or from at room temperature to under refluxing. In addition, this reaction can also be carried out under microwave irradiation. Note that, it is possible to carry out the reaction by adding acetic acid into a solvent which is inert to the reaction such as halogenated hydrocarbons, aromatic hydrocarbons, and ethers, instead of the acetic acid solvent. In addition, the reaction can also be carried out by further adding acetic anhydride.

(Process 4)

This step is a step of preparing a compound of the formula (u) by reacting the compound of the formula (p) with respect to and the compound of the formula (t) under a basic condition. The present reaction can be carried out by reacting the compound of the formula (t) with the compound of the formula (p) in the presence of an organic base such as triethylamine and N,N-diisopropylethylamine in an organic solvent which is inert to the reaction such as halogenated hydrocarbons, aromatic hydrocarbons, ethers, esters, acetonitrile, DMF, DMSO, and NMP. In addition, the compound of the formula (p) can also be used in an excess amount instead of the organic base. The reaction can be carried out under the temperature condition ranging from under cooling to at room temperature; from at room temperature to under heating; or from at room temperature to under refluxing.

(Process 5)

The step is a step of obtaining the compound of the formula (v) by removing the protecting group of the compound of the formula (u). Here, this reaction can be carried out by referring "Protective Groups in Organic Synthesis" written by Wuts and Greene, 4th edition, John Wiley & Sons Inc., 2006".

(Process 6)

This step is a step of obtaining the compound of the formula (w) from the compound of the formula (m). This reaction is carried out by an ipso-substitution reaction by using the compound of the formula (p) after brominating the 5-position of thiazole in the compound of the formula (m) by using a brominating agent such as N-bromosuccinimide so as to obtain the compound of the formula (w).

The compound of the formula (I) is isolated and purified as its free compound, or a salt, a hydrate, a solvate, or crystal polymorph substance thereof. The salt of the compound of the formula (I) can also be prepared by a conventional method.

Isolation and purification are carried out by employing general chemical operations such as extraction, fractional crystallization, and various types of fractional chromatography.

Various isomers can be prepared by selecting appropriate starting compound, or separated by using differences in the physicochemical properties among the isomers. For example, the optical isomers can be obtained by means of general optical resolution methods of racemic compounds (for example, fractional crystallization introducing the compound into a diastereomer salt with an optically active base or acid; chromatography using a chiral column or the like; and others), or can also be prepared from appropriate optically active starting compound.

The pharmacological activity of the compound of the formula (I) was confirmed by the following test.

Test Example 1: Evaluation of Muscarinic $M_3$ Receptor Positive Allosteric Modulator Activity a) Construction of Vector Expressing Human Muscarinic $M_3$ Receptor A human muscarinic $M_3$ receptor gene (GenBank Accession No.: NM_000740.2) was introduced into an expression vector pcDNA3.1 (registered trademark) (Life Technologies).

b) Construction of Cells Stably Expressing Human Muscarinic $M_3$ Receptor

A vector expressing a human muscarinic $M_3$ receptor was introduced into a CHO-K1 cell (ATCC No.: CCL-61). The introduction was carried out according to the attached instructions, using a transfection reagent, Lipofectoamine (registered trademark) 2000 Reagent (Life Technologies). The cells were incubated in an alpha Modified Eagle Minimum Essential Medium (α-MEM) including 2 mM L-glutamine, 10% fetal bovine serum, and 2.0 mg/mL Geneticin (registered trademark) (Life Technologies) for 4 weeks to acquire a drug-resistant clone.

c) Measurement of Intracellular $Ca^{2+}$ Concentration

The cells obtained in b) above were suspended in an α-MEM including 2 mM glutamine, 10% fetal bovine serum, and 0.2 mg/mL Geneticin (registered trademark) to the amount from 1.2 to $1.5 \times 10^4$ cells/well the day before the experiment, dispensed into a 384-well plate (Model No. 353962, BD Biosciences), and incubated overnight at 37° C. and 5% $CO_2$. The medium was replaced with a loading buffer (an assay buffer (Hank's balanced salt solution (HBSS) including 3.1 μM Fluo 4-AM (Dojindo Laboratories), 1 g/L BSA, 20 mM HEPES (pH 7.5), and 2.5 mM probenecid)), and incubated for about 2 hours at room temperature. Thereafter, the cells were washed with a plate washer ELx405 (registered trademark) (BIO-TEK Instrument, Inc.) set with the assay buffer, and set in an intracellular $Ca^{2+}$ concentration measuring system (FLIPR$^{tetra}$ (registered trademark), Molecular Device). The test substances were dissolved by using DMSO. The test substances (final concentration of 1 μM or 10 μM) and carbachol (Sigma, final concentration of 0.0024 nM to 10 μM) which had each been diluted in the assay buffer in advance were set in a FLIPR$^{tetra}$ (registered trademark). The test substances were added to the cells in the device and after about 5 minutes, carbachol was added to the cells. An increase rate of the intracellular $Ca^{2+}$ concentration by carbachol was measured (excitement wavelength of 470 to 495 nm and a fluorescence wavelength of 515 to 575 nm).

For the muscarinic $M_3$ receptor-positive allosteric modulator activity, a shift toward a lower concentration side of a carbachol concentration-response curve by the test substance was used as an index. That is, a minimum value in the carbachol response was taken as 0%; a maximum value in the carbachol response was taken as 100% from the concentration-response curve of carbachol; the carbachol concentration exhibiting a 50% response was calculated as an $EC_{50}$ value, using a Sigmoid-Emax model non-linear regression method, and thus, the muscarinic $M_3$ receptor-positive allosteric modulator activity was determined by dividing the $EC_{50}$ value of carbachol in the absence of the test substance by the $EC_{50}$ value of carbachol in the presence of the test substance. For example, when the $EC_{50}$ value of carbachol in the absence of the test substance was 0.1 μM and the $EC_{50}$ value of carbachol in the presence of the test substance was 0.01 μM, the value of the muscarinic $M_3$ receptor-positive allosteric modulator activity becomes 10, showing that the test substance causes a 10-fold shift in the $EC_{50}$ value toward to the low concentration side. In Tables below, the columns of 10 μM (-fold shift) show the values in a case where the test substance is added to a final concentration of 10 μM and the columns of 1 μM (-fold shift) show the values in a case where the test substance is added to a final concentration of 1 μM.

The muscarinic $M_3$ receptor-positive allosteric modulator activity (-fold shift) of Example compounds of the present invention are shown in Tables 1 and 2. However, Ex represents Example Compound Nos. as described later (this shall apply hereinafter).

TABLE 1

| Ex | 10 μM (Fold shift) | 1 μM (Fold shift) | Ex | 10 μM (Fold shift) | 1 μM (Fold shift) |
|---|---|---|---|---|---|
| 1 | 310 | 165 | 33 | 43 | 10 |
| 2 | 182 | 43 | 34 | 54 | 24 |
| 3 | 86 | 31 | 35 | 114 | 36 |
| 4 | 163 | 26 | 36 | 201 | 99 |
| 5 | 116 | 31 | 37 | 178 | 18 |
| 6 | 222 | 21 | 38 | 70 | 22 |
| 7 | 153 | 71 | 39 | 106 | 21 |
| 8 | 131 | 32 | 40 | 125 | 34 |
| 9 | 203 | 68 | 41 | 116 | 14 |
| 10 | 176 | 42 | 42 | 21 | 3 |
| 11 | 173 | 62 | 43 | 159 | 35 |
| 12 | 163 | 34 | 44 | 167 | 26 |
| 13 | 217 | 90 | 45 | 118 | 36 |
| 14 | 155 | 23 | 46 | 210 | 19 |
| 15 | 173 | 42 | 47 | 55 | 26 |
| 16 | 96 | 34 | 48 | 38 | 5 |
| 17 | 118 | 35 | 49 | 76 | 18 |
| 18 | 157 | 31 | 50 | 223 | 88 |
| 19 | 84 | 12 | 51 | 123 | 45 |
| 20 | 106 | 17 | 52 | 92 | 14 |
| 21 | 139 | 33 | 53 | 126 | 31 |

TABLE 1-continued

| Ex | 10 μM (Fold shift) | 1 μM (Fold shift) | Ex | 10 μM (Fold shift) | 1 μM (Fold shift) |
|---|---|---|---|---|---|
| 22 | 59 | 10 | 54 | 119 | 35 |
| 23 | 82 | 16 | 55 | 123 | 35 |
| 24 | 102 | 9 | 56 | 127 | 62 |
| 25 | 61 | 6 | 57 | 144 | 54 |
| 26 | 158 | 23 | 58 | 289 | 70 |
| 27 | 114 | 30 | 59 | 259 | 120 |
| 28 | 23 | 4 | 60 | 61 | 24 |
| 29 | 78 | 12 | 61 | 74 | 29 |
| 30 | 141 | 35 | 62 | 137 | 32 |
| 31 | 92 | 23 | 63 | 150 | 61 |
| 32 | 218 | 123 | 64 | 120 | 24 |

TABLE 2

| Ex | 10 μM (Fold shift) | 1 μM (Fold shift) | Ex | 10 μM (Fold shift) | 1 μM (Fold shift) |
|---|---|---|---|---|---|
| 65 | 318 | 59 | 84 | 100 | 48 |
| 66 | 155 | 34 | 85 | 169 | 69 |
| 67 | 328 | 102 | 86 | 74 | 28 |
| 68 | 625 | 196 | 87 | 15 | 2 |
| 69 | 114 | 54 | 88 | 22 | 4 |
| 70 | 117 | 49 | 89 | 118 | 19 |
| 71 | 215 | 63 | 90 | 236 | 65 |
| 72 | 167 | 172 | 91 | 42 | 11 |
| 73 | 369 | 84 | 92 | 84 | 29 |
| 74 | 140 | 45 | 93 | 51 | 7 |
| 75 | 129 | 98 | 94 | 54 | 19 |
| 76 | 128 | 26 | 95 | 163 | 38 |
| 77 | 65 | 32 | 96 | 58 | 8 |
| 78 | 81 | 14 | 97 | 67 | 12 |
| 79 | 99 | 16 | 98 | 91 | 10 |
| 80 | 365 | 141 | 99 | 90 | 25 |
| 81 | 55 | 12 | 100 | 261 | 59 |
| 82 | 303 | 94 | 101 | 78 | 36 |
| 83 | 162 | 41 | 102 | 110 | 32 |

Example compounds in Tables 1 and 2 shifted a carbachol concentration-response curve toward a lower concentration side when added at 1 μM and 10 μM. In addition, for all Example compounds, from the viewpoint that the compounds alone do not change the intracellular $Ca^{2+}$ concentration, it was found that these compounds have no muscarinic $M_3$ receptor agonistic activity.

Test Example 2: Effect on Electrical Field Stimulation-Induced Contraction in Rat Isolated Bladder As an effect on the nerve stimulation-dependent bladder contraction in in vitro, the effect of the Example compounds of the present invention in the electrical field stimulation-induced contraction of the rat isolated bladder was measured by the following method. That is, a bladder specimen having a width of about 2 mm and a length of about 10 mm in the longitudinal direction from the bladder isolated from a Sprague-Dawley (SD) female rat (Japan SLC, Inc.) was prepared. The prepared bladder specimen was suspended in an organ bath filled with 10 mL of a Krebs-Henseleite solution. The Krebs-Henseleite solution was aerated at 95% $O_2$ and 5% $CO_2$, and kept at 37° C. After carrying out stabilization at an initial tension of 1 g, the contraction was caused twice with 60 mM KCl. After stabilization of the specimen with a Krebs-Henseleite solution, the contraction was caused by carrying out electrical field stimulation at 20 V with an electrical stimulation device (Nihon Kohden) (a stimulation frequency of 8 Hz, a pulse width of 0.3 msec, and a stimulation time of 10 seconds). By repeating the transmural electrical stimulation at an interval of 2 minutes, a voltage was adjusted to obtain a contraction height of approximately 50% of the contractile response at 20 V. After the contraction by electrical field stimulation had been stabilized, 10 µL of the test substances dissolved in 100% DMSO in advance (final concentrations of 3 µM, 10 µM, and 30 µM) was added thereto. The test substances were cumulatively administered at the following concentrations after the low-concentration contractile response had been stabilized. The response was taken into a personal computer through a PowerLab (registered trademark) (AD Instruments, Inc.), and analyzed by LabChart (registered trademark) (AD Instruments, Inc.). When the area under the response (area under curve, AUC) in each contraction response was calculated and the value before treatment with the test substance was taken as 100%, the enhancement rate (% of pre) of the isolated bladder contractions after treatment with the test substance was calculated.

The enhancement rates of the isolated bladder contractions by 10 µM of some Example compounds are shown in Table 3.

Furthermore, it was separately confirmed that all the Example compounds which have been subjected to the present test do not cause contraction in a state in which there is no electrical stimulation and the compounds alone do not show a bladder contraction action.

TABLE 3

| Ex | Enhancement rate of extracted bladder contractions (% of pre) |
|----|---|
| 1  | 120 |
| 3  | 136 |
| 4  | 127 |
| 8  | 193 |
| 9  | 187 |
| 10 | 271 |
| 11 | 219 |
| 12 | 166 |
| 13 | 127 |
| 14 | 169 |
| 17 | 199 |
| 18 | 199 |
| 19 | 161 |
| 91 | 124 |

From the above, it was confirmed that the Example compounds alone, which have been subjected to the present test, do not cause a contraction action in the isolated rat bladder, but have an action of enhancing electrical field stimulation-induced contraction.

Test Example 3: Effect on Pelvic Nerve Stimulation-Induced Elevation of Intravesical Pressure in Anesthetized Rats The effect of the Example compounds of the present invention in the pelvic nerve electrical stimulation-induced elevation of intravesical pressure using rats as an action of nerve stimulation-dependent bladder contraction in vivo was measured by the following method. That is, SD female rats (Japan SLC, Inc.) were used and its lower abdomen was dissected at the midline under pentobarbital anesthesia (50 mg/kg ip). After ligating and cutting the ureter on both sides, a cannula (PE-50) for measuring the intravesical pressure was inserted into the bladder from the external urethral opening and fixed by a clip. After injecting about 200 µL of saline through the cannula that had been inserted into the bladder, the other side was connected to a pressure transducer to measure the intravesical pressure. Under a stereoscopic microscope observation, the pelvic nerve in the vicinity of the bladder was peeled and an electrode for nerve stimulation (unique Medical) was placed. The abdominal cavity was filled with mineral oil (MP BIOMEDICALS). After placing in a post-operative stabilization period, the pelvic nerve was subjected to electrical stimulation (stimulation voltage: 10 V, stimulation frequency: 8 Hz, pulse width: 0.3 msec, and stimulation time: 10 seconds) to elicit the elevation of intravesical pressure, using an electrical stimulator (Nihon Kohden). By repeating the electrical stimulation at an interval of 2 minutes while adjusting the voltage, the voltage was adjusted to elicit about 50% to 70% elevation of intravesical pressure elicited at 10 V. Thereafter, by repeating the electrical stimulation at an interval of 10 minutes, the increase in the intravesical pressure by electrical stimulation was stabilized three times or more, and the test substance (an administration amount of 3 mg/kg) was then administered from the catheter detained in the vein at a volume of 1 mL/kg, thus measuring an effect of the elevation of the intravesical pressure of the test substance for 1 hour. The test substance was dissolved in water supplemented with 10% DMSO and 10% Cremophor.

The response was applied to a personal computer through a PowerLab (registered trademark) and analyzed by LabChart (registered trademark). The AUC of each elevation of the intravesical pressure was calculated, the intravesical pressure elevation rate (% of pre) after the treatment with the test substance was calculated by taking an average value of the values measured three times before the treatment with the test substance as 100%, and the maximum effect during a period within one hour after administration of the compound was considered as the effect of the test substance.

The elevation rates (% of pre) of the intravesical pressure when some Example compounds were administered at 3 mg/kg are shown in Table 4.

TABLE 4

| Ex | Increase rate of intravesical pressure (% of pre) | Ex | Increase rate of intravesical pressure (% of pre) |
|----|------|----|------|
| 1  | 197  | 38 | 142  |
| 2  | 143  | 39 | 123  |
| 3  | 146  | 40 | 212  |
| 4  | 178  | 43 | 177  |
| 5  | 146  | 45 | 182  |
| 8  | 178  | 51 | 129  |
| 9  | 200  | 53 | 145  |
| 10 | 169  | 54 | 150  |
| 11 | 181  | 55 | 189  |
| 12 | 152  | 58 | 175  |
| 13 | 186  | 59 | 225  |
| 14 | 121  | 63 | 198  |
| 15 | 130  | 65 | 174  |
| 16 | 111  | 67 | 169  |
| 17 | 144  | 68 | 172  |
| 18 | 153  | 69 | 150  |
| 19 | 125  | 70 | 151  |
| 20 | 118  | 71 | 197  |
| 21 | 116  | 77 | 140  |
| 26 | 125  | 86 | 164  |
| 27 | 123  | 91 | 144  |
| 29 | 145  | 92 | 105  |
| 30 | 124  | 94 | 114  |
| 31 | 138  | 97 | 143  |
| 32 | 232  | 98 | 139  |

TABLE 4-continued

| Ex | Increase rate of intravesical pressure (% of pre) | Ex | Increase rate of intravesical pressure (% of pre) |
| --- | --- | --- | --- |
| 34 | 159 | 99 | 121 |
| 35 | 154 | 100 | 145 |
| 36 | 191 | | |

In addition, it was confirmed that the Example compounds evaluated in the present test do not cause an elevation of the intravesical pressure in a state in which electrical stimulation is not given, and the compounds alone do not show elevation of the intravesical pressure.

From the above, it was confirmed that the Example compounds listed in Table 4 alone do not show elevation of the intravesical pressure but have an action of enhancing effect on the pelvic nerve electrical stimulation-induced elevation of intravesical pressure in the anesthetized rats.

As shown in the results of each the tests above, it was confirmed that the compound of the formula (I) has a muscarinic $M_3$ receptor-positive allosteric modulator activity, and further, it enhances the bladder contraction in a nerve stimulation-dependent manner in in vitro, as well as enhances an elevation in the intravesical pressure in a nerve stimulation-dependent manner in in vivo. Accordingly, the compound of the formula (I) can be used to prevent or treat bladder/urinary tract diseases associated with bladder contractions via a muscarinic $M_3$ receptor, in particular, voiding dysfunction or urine storage dysfunction in the bladder/urethral diseases. The compound of the formula (I) can be used for preventing or treating, for example, voiding dysfunction or urine storage dysfunction in underactive bladder, hypotonic bladder, acontraction bladder, detrusor underactivity, neurogenic bladder, urethra relaxation failure, detrusor-external urethral sphincter dyssynergia, overactive bladder, urinary frequency, nocturia, urinary incontinence, benign prostatic hyperplasia, interstitial cystitis, chronic prostatitis, and urinary tract stones. In particular, the compound of the formula (I) can be used for preventing or treating voiding dysfunction or urine storage dysfunction in underactive bladder, hypotonic bladder, acontraction bladder, detrusor underactivity, and neurogenic bladder.

In addition, the compound of formula (I) can become a therapeutic drug that is more excellent in safety from the viewpoint that the compound alone does not show an agonistic effect on a muscarinic $M_3$ receptor, but shows an effect on enhancing the nerve stimulation-dependent bladder contraction, and accordingly, cholinergic side effects that have been reported in the existing drugs can be avoided.

A pharmaceutical composition including one or two or more kinds of the compound of the formula (I) as an active ingredient can be prepared using an excipient which is usually used in the art, that is, an excipient for a pharmaceutical preparation, a carrier for a pharmaceutical preparation, and the like, according to a method usually used.

Administration can be accomplished either by oral administration via tablets, pills, capsules, granules, powders, solutions, and the like, or parenteral administration via injections, such as intraarticular, intravenous, and intramuscular injections, suppositories, transdermal liquid preparations, ointments, transdermal patches, transmucosal liquid preparations, transmucosal patches, inhalers, and the like.

As a solid composition for oral administration, tablets, powders, granules, and the like are used. In such a solid composition, one kind or two or more kinds of the active ingredients are mixed with at least one inactive excipient. In a conventional method, the composition may contain inactive additives such as a lubricant, a disintegrating agent, a stabilizer, or a solubilization assisting agent. If necessary, tablets or pills may be coated with a sugar or with a film of a gastric or enteric coating substance.

The liquid composition for oral administration includes pharmaceutically acceptable emulsions, solutions, suspensions, syrups, elixirs, or the like, and also includes generally used inert diluents, for example, purified water or ethanol. The liquid composition may also include auxiliary agents such as a solubilization assisting agent, a moistening agent, and a suspending agent, sweeteners, flavors, aromatics, and antiseptics, in addition to the inert diluent.

The injections for parenteral administration include sterile aqueous or non-aqueous solution preparations, suspensions, or emulsions. The aqueous solvent includes, for example, distilled water for injection and saline. Examples of the non-aqueous solvent include alcohols such as ethanol. Such a composition may further include a tonicity agent, an antiseptic, a moistening agent, an emulsifying agent, a dispersing agent, a stabilizing agent, or a solubilizing assisting agent. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to its use.

Examples of the agent for external use include ointments, hard plasters, creams, jellies, cataplasms, sprays, and lotions. The agent further contains generally used ointment bases, lotion bases, aqueous or non-aqueous liquid preparations, suspensions, emulsions, or the like.

As the transmucosal agents such as an inhaler and a transnasal agent, those in the form of a solid, liquid, or semi-solid state are used, and can be prepared in accordance with a method known in the related art. For example, a known excipient, and also a pH adjusting agent, an antiseptic, a surfactant, a lubricant, a stabilizing agent, a thickening agent, or the like may be appropriately added thereto. For the administration, an appropriate device for inhalation or blowing can be used. For example, a compound may be administered alone or as a powder of formulated mixture, or as a solution or suspension in combination with a pharmaceutically acceptable carrier, using a known device or sprayer such as a metered administration inhalation device. A dry powder inhaler or the like may be for single or multiple administration use, and a dry powder or a powder-containing capsule may be used. Alternatively, this may be in a form such as a pressurized aerosol spray that uses an appropriate propellant agent, for example, a suitable gas such as chlorofluoroalkanes, and carbon dioxide, or other forms.

Usually, in the case of oral administration, the daily dose is from about 0.001 mg/kg to 100 mg/kg, preferably from 0.1 mg/kg to 30 mg/kg, and more preferably from 0.1 mg/kg to 10 mg/kg, per body weight, administered in one portion or in 2 to 4 divided portions. In the case of intravenous administration, the daily dose is suitably administered from about 0.0001 mg/kg to 10 mg/kg per body weight, once a day or two or more times a day. In addition, a transmucosal agent is administered at a dose from about 0.001 mg/kg to 100 mg/kg per body weight, once or plural times a day. The dose is appropriately decided in response to the individual case by taking the symptoms, the age, and the gender, and the like into consideration.

Although there are differences depending on a route of administration, a dosage form, an administration site, and a type of the excipient or additive, a pharmaceutical composition of the present invention comprises 0.01% by weight to 100% by weight of, as an embodiment, 0.01% by weight to 50% by weight of, one or more of the compound of the formula (I) or a salt thereof which is the active ingredient.

The compound of the formula (I) may be used in combination with various agents for treating or preventing diseases on which the compound of the formula (I) is considered to show the effect. Such combined preparations may be administered simultaneously, or separately and continuously, or at a desired time interval. The preparations to be co-administered may be a blend, or may be prepared individually.

EXAMPLES

Hereinbelow, the production process for the compound of the formula (I) will be described in more detail with reference to Examples. Further, the present invention is not limited to the compounds described in the Examples below. Further, the production processes for the starting compounds will be described in Preparation Examples. In addition, the production processes for the compound of the formula (I) are not limited to the production processes of the specific Examples shown below, but the compound of the formula (I) can be prepared by a combination of these production processes or a method that is apparent to a person skilled in the art.

Further, in the present specification, nomenclature software such as ACD/Name (registered trademark, Advanced Chemistry Development, Inc.) may be used for nomenclature of compounds in some cases.

Moreover, the following abbreviations may be used in Examples, Preparation Examples, and Tables below in some cases.

PEx: Preparation Example No., Ex: Example No., PSyn: Preparation method of Preparation Example compound (the number in the PSyn column indicates that the compound was produced by using the corresponding starting material in the same manner as the compound having the number as the number of Preparation Example compound. For example, the compound in which the PSyn column is 2 means that it was prepared in the same manner as the compound of Preparation Example 2), Syn: Preparation method of Example compounds (the number in the Syn column indicates that the compound was produced by using the corresponding starting material in the same manner as the compound having the number as the number of Example compound. For example, the compound in which the Syn column is 2 means that it was prepared in the same manner as the compound of Example 2), Str: Structural chemical formula (Me represents methyl, Et represents ethyl, i-Pr represents isopropyl, c-Pr represents cyclopropyl, tBu represents tert-butyl, Boc represents tert-butoxycarbonyl, and Ac represents acetyl), DAT: Physicochemical data, ESI+: m/z values in mass spectroscopy (Ionization method ESI, representing [M+H]$^+$ unless otherwise specified), ESI-: m/z values in mass spectroscopy (Ionization method ESI, representing [M−H]$^+$ unless otherwise specified), APCI/ESI+: m/z values in mass spectroscopy (APCI/ESI-MS (atmospheric pressure chemical ionization method APCI, representing [M+H]$^+$ unless otherwise specified; in which APCI/ESI means simultaneous measurement of APCI and ESI)), EI: m/z values in mass spectroscopy (ionization method EI, representing [M]$^+$ unless otherwise specified), CI: m/z values in mass spectroscopy (Ionization method CI, representing [M+H]$^+$ unless otherwise specified), NMR-CDCl3: δ (ppm) of peaks in $^1$H-NMR in CDCl$_3$, NMR-DMSO-d6: δ (ppm) of peaks in $^1$H-NMR in DMSO-d$_6$, s: singlet (spectrum), d: doublet (spectrum), t: triplet (spectrum), q: quartet (spectrum) br: broad (spectrum) (e.g.: brs), m: multiplet (spectrum). Further, HCl in the structural formula indicates that the compound is a monohydrochloride; and 2HCl indicates that the compound is a dihydrochloride.

In addition, for the sake of convenience, a concentration of mol/L is represented by M. For example, a 1 M aqueous sodium hydroxide solution means a 1 mol/L aqueous sodium hydroxide solution.

Preparation Example 1

Sodium hydride (90 mg, 60% oil dispersion) was added to a mixture of 5-{[(2R,5R)-2,5-dimethylpyrrolidin-1-yl]methyl}-4-[3-fluoro-5-(trifluoromethyl)phenyl]-1,3-thiazol-2-amine (300 mg), 4,6-dichloro-5-fluoro-2-methylpyrimidine (175 mg), and dehydrated tetrahydrofuran (6.0 mL) in an argon atmosphere under ice-methanol bath cooling, followed by stirring at 0° C. for 30 minutes. The resultant was extracted with ethyl acetate after adding ice-water to the reaction mixture. The organic layer was washed with saturated brine, dried over anhydrous magnesium sulfate, and concentrated under reduced pressure. The obtained residue was purified by silica gel column chromatography (hexane-ethyl acetate) to obtain 6-chloro-N-(5-{[(2R,5R)-2,5-dimethylpyrrolidin-1-yl]methyl}-4-[3-fluoro-5-(trifluoromethyl)phenyl]-1,3-thiazol-2-yl)-5-fluoro-2-methylpyrimidin-4-amine (407 mg) as a solid.

Preparation Example 2

N,N-diisopropylethylamine (1.2 mL) was added to a mixture of N$^2$-(6-chloro-2-methylpyrimidin-4-yl)-4-[3-fluoro-5-(trifluoromethyl)phenyl]-N$^5$-isopropyl-N$^5$-(2-methoxyethyl)-1,3-thiazole-2,5-diamine (279 mg), ethyl 3-(piperazin-1-yl)propanoate dihydrochloride (440 mg), and 1-methylpyrrolidin-2-one (NMP) (6.0 mL) at room temperature. The reaction mixture was stirred at 80° C. for 12 hours. Ethyl acetate and water were added the reaction mixture so as to separate the organic layer. The organic layer was dried over anhydrous magnesium sulfate, and concentrated under reduced pressure. The obtained residue was purified by silica gel column chromatography (hexane-ethyl acetate) to obtain ethyl 3-{4-[6-({4-[3-fluoro-5-(trifluoromethyl)phenyl]-5-[isopropyl(2-methoxyethyl)amino]-1,3-thiazol-2-yl}amino)-2-methylpyrimidin-4-yl]piperazin-1-yl}propanoate (303 mg) as a solid.

Preparation Example 3

A mixture of 6-chloro-5-fluoro-N-(4-[3-fluoro-5-(trifluoromethyl)phenyl]-5-{[(2R)-2-methylpyrrolidin-I-yl]methyl}-1,3-thiazol-2-yl)-2-methylpyrimidin-4-amine (662 mg), ethyl 3-(piperazin-1-yl)propanate dihydrochloride (1.7 g), N,N-diisopropylethylamine (4.0 mL), and NMP (10 mL) was stirred at 80° C. for 4 hours. Ethyl acetate and water were added the reaction mixture so as to separate the organic layer. The organic layer was washed with water, dried over anhydrous magnesium sulfate, and concentrated under reduced pressure. The obtained residue was purified by silica gel column chromatography (hexane-ethyl acetate) and silica gel column chromatography (chloroform-ethyl acetate) to obtain ethyl 3-(4-{5-fluoro-6-[(4-[3-fluoro-5-(trifluoromethyl)phenyl]-5-{[(2R)-2-methylpyrrolidin-1-yl]

Preparation Example 4

A mixture of ethyl 3-[(2S)-4-(6-chloro-5-fluoropyrimidin-4-yl)-2-(methoxymethyl)piperazin-1-yl]propanoate (145 mg), 4-[4-chloro-3-(trifluoromethyl)phenyl]-5-{[(2R)-2-methylpyrrolidin-1-yl]methyl}-1,3-thiazol-2-amine (150 mg), tris(dibenzylideneacetone) dipalladium (110 mg), 1,1'-binaphthalene-2,2'-diyl bis(diphenylphosphine) (150 mg), cesium carbonate (520 mg), and toluene (3.0 mL) was stirred at 100° C. for 5 hours under an argon atmosphere. The reaction mixture was concentrated under reduced pressure, and the residue was purified by silica gel column chromatography (hexane-ethyl acetate) and basic silica gel column chromatography (hexane-ethyl acetate) to obtain ethyl 3-[(2S)-4-{6-[(4-[4-chloro-3-(trifluoromethyl)phenyl]-5-{[(2R)-2-methylpyrrolidin-1-yl]methyl}-1,3-thiazol-2-yl)amino]-5-fluoropyrimidin-4-yl}-2-(methoxymethyl)piperazin-1-yl]propanoate (192 mg) as a solid.

Preparation Example 5

A mixture of tert-butyl 3-[4-(2-chloro-3-fluoropyridin-4-yl)piperazin-1-yl]propanate (497 mg), 4-[3-fluoro-5-(trifluoromethyl)phenyl]-5-{[(2R)-2-methylpyrrolidin-1-yl]methyl}-1,3-thiazol-2-amine (500 mg), tris(dibenzylideneacetone) dipalladium (640 mg), 1,1'-binaphthalene-2,2'-diyl bis(diphenylphosphine) (900 mg), cesium carbonate (1.9 g), and NMP (15 mL) was stirred at 100° C. for 6 hours under an argon atmosphere. The reaction mixture was diluted with ethyl acetate and water, and filtered through a celite pad. A filtrate was washed with water and saturated brine, dried over anhydrous magnesium sulfate, and concentrated under reduced pressure. The residue was purified by silica gel column chromatography (chloroform-ethyl acetate), silica gel column chromatography (hexane-ethyl acetate), and silica gel column chromatography (chloroform-ethyl acetate) to obtain tert-butyl 3-(4-{3-fluoro-2-[(4-[3-fluoro-5-(trifluoromethyl)phenyl]-5-{[(2R)-2-methylpyrrolidin-1-yl]methyl}-1,3-thiazol-2-yl)amino]pyridin-4-yl}piperazin-1-yl)propanate (387 mg) as a solid.

Preparation Example 6

(2R)-2-methylpyrrolidine (0.15 mL) was added to a mixture of ethyl 3-{4-[5-fluoro-6-({4-[6-methoxy-5-(trifluoromethyl)pyridin-3-yl]-1,3-thiazol-2-yl}amino)pyrimidin-4-yl]piperazin-1-yl}propanoate (400 mg), paraformaldehyde (65 mg), and acetic acid (6.0 mL), and stirred at 75° C. for 2.5 hours. The reaction mixture was concentrated under reduced pressure, and the residue was diluted with ethyl acetate and water. To the reaction mixture was added a saturated aqueous sodium hydrogen carbonate solution, followed by extraction with ethyl acetate. The organic layer was dried over anhydrous magnesium sulfate, and concentrated under reduced pressure. The residue was purified by silica gel column chromatography (hexane-ethyl acetate) to obtain ethyl 3-(4-{5-fluoro-6-[(4-[6-methoxy-5-(trifluoromethyl)pyridin-3-yl]-5-{[(2R)-2-methylpyrrolidin-1-yl]methyl}-1,3-thiazol-2-yl)amino]pyrimidin-4-yl}piperazin-1-yl)propanoate (328 mg) as a solid.

Preparation Example 7

Paraformaldehyde (55 mg) was added to a mixture of ethyl 3-{4-[5-fluoro-6-({4-[3-fluoro-5-(trifluoromethyl)phenyl]-1,3-thiazol-2-yl}amino)pyrimidin-4-yl]piperazin-1-yl}propanoate (300 mg), (3S)-3-methoxypyrrolidine hydrochloride (110 mg), and acetic acid (5.0 mL) at room temperature. The reaction mixture was stirred at 85° C. for 1 hour. The reaction mixture was added acetic anhydride (0.50 mL) and was stirred at 85° C. for 4 hours. To the reaction mixture was added water, followed by extraction with ethyl acetate. The organic layer was washed with water, dried over anhydrous magnesium sulfate, and concentrated under reduced pressure. The obtained residue was purified by neutral silica gel column chromatography (hexane-ethyl acetate) and neutral silica gel column chromatography (chloroform-methanol) to obtain ethyl 3-(4-{5-fluoro-6-[(4-[3-fluoro-5-(trifluoromethyl)phenyl]-5-{[(3 S)-3-methoxypyrrolidin-1-yl]methyl}-1,3-thiazol-2-yl)amino]pyrimidin-4-yl}piperazin-1-yl)propanoate (150 mg) as a solid.

Preparation Example 8

A mixture of N-(4-[4-chloro-3-(trifluoromethyl)phenyl]-5-{[(2R)-2-methylpyrrolidin-1-yl]methyl}-1,3-thiazol-2-yl)-3-fluoro-4-(piperazin-1-yl)pyridin-2-amine (300 mg), ethyl acrylate (0.50 mL), and ethanol (10 mL) was stirred at 100° C. for 15 minutes under microwave irradiation. The reaction liquid was concentrated under reduced pressure, and the residue was purified by basic silica gel column chromatography (hexane-ethyl acetate) to obtain ethyl 3-(4-{2-[(4-[4-chloro-3-(trifluoromethyl)phenyl]-5-{[(2R)-2-methylpyrrolidin-1-yl]methyl}-1,3-thiazol-2-yl)amino]-3-fluoropyridin-4-yl}piperazin-1-yl)propanoate (137 mg) as a solid.

Preparation Example 9

A mixture of tert-butyl 4-{2-[(4-[4-chloro-3-(trifluoromethyl)phenyl]-5-{[(2R)-2-methylpyrrolidin-1-yl]methyl}-1,3-thiazol-2-yl)amino]-3-fluoropyridin-4-yl}piperazine-1-carboxylate (457 mg), and 4 M hydrogen chloride dioxane solution (13 mL) was stirred at room temperature for 2 hours. The reaction mixture was concentrated under reduced pressure, and chloroform and saturated aqueous sodium hydrogen carbonate solution were added to the residue. The organic layer was separated, dried over anhydrous sodium sulfate, and then concentrated under reduced pressure. The residue was purified by basic silica gel column chromatography (chloroform-methanol) to obtain N-(4-[4-chloro-3-(trifluoromethyl)phenyl]-5-{[(2R)-2-methylpyrrolidin-1-yl]methyl}-1,3-thiazol-2-yl)-3-fluoro-4-(piperazin-1-yl)pyridin-2-amine (302 mg) as a solid.

Preparation Example 10

4 M hydrogen chloride ethyl acetate solution (2.2 mL) was added to a mixture of tert-butyl (3S)-4-{5-fluoro-6-[(4-[3-fluoro-5-(trifluoromethyl)phenyl]-5-{[(2R)-2-methylpyrrolidin-1-yl]methyl}-1,3-thiazol-2-yl)amino]pyrimidin-4-yl}-3-(methoxymethyl)piperazine-1-carboxylate (154 mg) and tetrahydrofuran (0.64 mL), and the reaction mixture was stirred at room temperature for 6 hours. The reaction mixture was concentrated under reduced pressure to obtain 5-fluoro-N-(4-[3-fluoro-5-(trifluoromethyl)phenyl]-5-{[(2R)-2-methylpyrrolidin-1-yl]methyl}-1,3-thiazol-2-yl)-6-[(2S)-2-(methoxymethyl)piperazin-1-yl]pyrimidin-4-amine trihydrochloride (159 mg) as a solid.

Preparation Example 11

6 M aqueous sodium hydroxide solution (1.0 mL) was added to a mixture of N-(4-[4-chloro-3-(trifluoromethyl)

phenyl]-5-{[(2R)-2-methylpyrrolidin-1-yl]methyl}-1,3-thiazol-2-yl)acetamide (240 mg) and ethanol (4 mL), and the reaction mixture was stirred at 100° C. for 4 hours under an argon atmosphere. To the reaction mixture was added water, followed by extraction with ethyl acetate. The organic layer was washed with saturated brine, dried over anhydrous magnesium sulfate, and then concentrated under reduced pressure. The obtained residue was purified by basic silica gel column chromatography (hexane-ethyl acetate) to obtain 4-[4-chloro-3-(trifluoromethyl)phenyl]-5-{[(2R)-2-methylpyrrolidin-1-yl]methyl}-1,3-thiazol-2-amine (164 mg) as a solid.

Preparation Example 12

A mixture of N-(4-[3-fluoro-5-(trifluoromethyl)phenyl]-5-{[(2R)-2-methylpyrrolidin-1-yl]methyl}-1,3-thiazol-2-yl)acetamide (1.4 g), ethanol (10 mL), and a 6 M aqueous sodium hydroxide solution (5.0 mL) was stirred at 120° C. for 15 minutes under microwave irradiation. To the reaction mixture was added water, followed by extraction with ethyl acetate. The organic layer was washed with saturated brine, dried over anhydrous magnesium sulfate, and then concentrated under reduced pressure. The residue was purified by silica gel column chromatography (hexane-ethyl acetate) to obtain 4-[3-fluoro-5-(trifluoromethyl)phenyl]-5-{[(2R)-2-methylpyrrolidin-1-yl]methyl}-1,3-thiazol-2-amine (1.0 g) as an oil.

Preparation Example 13

A mixture of N-(5-{[(2R,5R)-2,5-dimethylpyrrolidin-1-yl]methyl}-4-[3-fluoro-5-(trifluoromethyl)phenyl]-1,3-thiazol-2-yl)acetamide (916 mg), and concentrated sulfuric acid (8.0 mL) and water (2.0 mL) was stirred at 100° C. for 1 hour. The reaction mixture was cooled to 5° C. and alkalified by the addition of a 5 M aqueous sodium hydroxide solution and a saturated aqueous sodium hydrogen carbonate solution. The mixture was extracted with chloroform, and the organic layer was dried over anhydrous magnesium sulfate and then concentrated under reduced pressure. The residue was purified by basic silica gel column chromatography (hexane-ethyl acetate) to obtain 5-{[(2R,5R)-2,5-dimethylpyrrolidin-1-yl]methyl}-4-[3-fluoro-5-(trifluoromethyl)phenyl]-1,3-thiazol-2-amine (685 mg) as a solid.

Preparation Example 14

A mixture of N-{4-[3-fluoro-5-(trifluoromethyl)phenyl]-1,3-thiazol-2-yl}acetamide (2.8 g), acetic acid (20 mL), 36% formaldehyde aqueous solution (3.6 mL), and acetic anhydride (4.4 mL) was stirred at 170° C. for 30 minutes under microwave irradiation. The reaction mixture was concentrated under reduced pressure, and then the obtained solid was washed with methanol, and collected by filtration. The obtained solid (1.8 g) and NMP (20 mL), (2R)-2-methylpyrrolidone (608 mg), and N,N-diisopropylethylamine (2.5 mL) were mixed, and the reaction mixture was stirred at 100° C. for 30 minutes. The reaction mixture was cooled to room temperature, and water was added to the reaction mixture and was extracted with ethyl acetate. The organic layer was washed with saturated brine, dried over anhydrous magnesium sulfate, and then concentrated under reduced pressure. The residue was purified by silica gel column chromatography (hexane-ethyl acetate) to obtain N-(4-[3-fluoro-5-(trifluoromethyl)phenyl]-5-{[(2R)-2-methylpyrrolidin-1-yl]methyl}-1,3-thiazol-2-yl)acetamide (1.4 g) as a solid.

Preparation Example 15

A mixture of {2-acetamide-4-[3-fluoro-5-(trifluoromethyl)phenyl]-1,3-thiazole-5-yl}methyl acetate (1.0 g), (−)-(2R,5R)-2,5-dimethylpyrrolidine hydrochloride (600 mg), N,N-diisopropylethylamine (2.0 mL), and NMP (10 mL) was stirred at 100° C. for 3 hours. The reaction mixture was diluted with ethyl acetate, and the organic layer was washed with water and saturated brine. The obtained organic layer was dried over anhydrous magnesium sulfate, and concentrated under reduced pressure. The residue was purified by silica gel column chromatography (chloroform-ethyl acetate) to obtain an oil. To the obtain oil (1.4 g) was added to ethyl acetate and water, followed by extraction with ethyl acetate. The organic layer was washed with water and saturated brine, dried over anhydrous magnesium sulfate, and then concentrated under reduced pressure to obtain N-(5-{[(2R,5R)-2,5-dimethylpyrrolidin-1-yl]methyl}-4-[3-fluoro-5-(trifluoromethyl)phenyl]-1,3-thiazol-2-yl)acetamide (965 mg) as a solid.

Preparation Example 16

N,N-diisopropylethylamine (0.55 mL) was added to a mixture of {2-acetamide-4-[4-chloro-3-(trifluoromethyl)phenyl]-1,3-thiazole-5-yl}methyl acetate (525 mg), (2R)-2-methylpyrrolidine hydrochloride (201 mg), and N,N-dimethylformamide (DMF) (4.2 mL), and the reaction mixture was stirred at 120° C. for 30 minutes under microwave irradiation. To the reaction mixture was added (2R)-2-methylpyrrolidine hydrochloride (244 mg) and N,N-diisopropylethylamine (0.69 mL), and the obtained mixture was stirred at 140° C. for 30 minutes under microwave irradiation. The reaction mixture was concentrated under reduced pressure, and the obtained residue was purified by basic silica gel column chromatography (hexane-ethyl acetate) to obtain N-(4-[4-chloro-3-(trifluoromethyl)phenyl]-5-{[(2R)-2-methylpyrrolidin-1-yl]methyl}-1,3-thiazol-2-yl)acetamide (245 mg) as an oil.

Preparation Example 17

A mixture of N-{4-[3-fluoro-5-(trifluoromethyl)phenyl]-1,3-thiazol-2-yl}acetamide (6.0 g), acetic acid (30 mL), 36% formaldehyde aqueous solution (7.5 mL), and acetic anhydride (9.0 mL) was stirred at 170° C. for 15 minutes under microwave irradiation. The reaction mixture was concentrated under reduced pressure. Ethyl acetate was added to the obtained residue, and the organic layer was washed with saturated aqueous sodium hydrogen carbonate solution, water, and saturated brine, dried over anhydrous magnesium sulfate, and then concentrated under reduced pressure. The obtained residue was purified by silica gel column chromatography (chloroform-methanol). The obtained solid was washed with diisopropyl ether, collected by filtration, and dried to obtain {2-acetamide-4-[3-fluoro-5-(trifluoromethyl)phenyl]-1,3-thiazole-5-yl}methyl acetate (2.6 g) as a solid.

Preparation Example 18

A mixture of N-{4-[3-chloro-5-(trifluoromethoxy)phenyl]-1,3-thiazol-2-yl}acetamide (3.8 g), 37% formaldehyde aqueous solution (5.1 mL), acetic anhydride (11 mL), and acetic acid (19 mL) was heated to reflux overnight. The reaction mixture was concentrated under reduced pressure, and the obtained residue was washed with hexane-diisopropyl ether to obtain {2-acetamide-4-[3-chloro-5-(trifluoromethoxy)phenyl]-1,3-thiazole-5-yl}methyl acetate (2.4 g) as a solid.

Preparation Example 19

A mixture of 4-[3-fluoro-5-(trifluoromethyl)phenyl]-1,3-thiazol-2-amine (2.8 g), pyridine (10 mL), and acetic anhydride (4.0 mL) was stirred at 60° C. for 1 hour. The reaction mixture was cooled to room temperature, water was added to the reaction mixture, and the obtained solid was collected by filtration. The obtained solid was washed with methanol, was collected by filtration, and dried to obtain N-{4-[3-fluoro-5-(trifluoromethyl)phenyl]-1,3-thiazol-2-yl}acetamide (2.9 g) as a solid.

Preparation Example 20

N-bromosuccinimide (190 mg) was added to a mixture of 4-[3-fluoro-5-(trifluoromethyl)phenyl]-1,3-thiazol-2-amine (250 mg), and DMF (6.0 mL) at 0° C., and the reaction mixture was stirred at room temperature for 1 hour. To the reaction mixture was added N-(2-methoxyethyl)propane-2-amine (0.17 mL) and potassium carbonate (420 mg), followed by stirring at 80° C. for 1 hour. To the reaction mixture was added ethyl acetate and water, followed by extraction with ethyl acetate, and the organic layer was dried over anhydrous sodium sulfate, and then concentrated under reduced pressure. The residue was purified by silica gel column chromatography (hexane-ethyl acetate) to obtain 4-[3-fluoro-5-(trifluoromethyl)phenyl]-$N^5$-isopropyl-N-(2-methoxyethyl)-1,3-thiazole-2,5-diamine (241 mg) as an oil.

Preparation Example 21

Phenyltrimethylammonium tribromide (143 g) was added to a mixture of 1-[3-fluoro-5-(trifluoromethyl)phenyl]ethanone (78 g) and tetrahydrofuran (625 mL) was stirred at room temperature for 1 hour. The insoluble materials were separated by filtration, and then the filtrate was concentrated under reduced pressure. The obtained residue was mixed with ethanol (625 mL), and to the mixture was added thiourea (35 g), followed by stirring at 65° C. to 75° C. for 2 hours. The reaction mixture was ice-cooled, and then water (625 mL) was added thereto. To the mixture was added 1 M sodium hydroxide (600 mL), followed by stirring for 30 minutes. The solid was collected by filtration, 70% ethanol water (600 mL) was added thereto, and the mixture was dissolved at 76° C. The obtained solution was cooled to room temperature and was stirred overnight. The mixture was ice-cooled, stirred for 2 hours, and then the precipitated solid was collected by filtration and was dried over under reduced pressure to obtain 4-[3-fluoro-5-(trifluoromethyl)phenyl]-1,3-thiazol-2-amine (57 g) as a solid.

Preparation Example 22

Ethyl 3-[(2S)-2-(methoxymethyl)piperazin-1-yl]propanoate dihydrochloride (400 mg), and N,N-diisopropylethylamine (1.1 mL) were sequentially added to a mixture of 4,6-dichloro-5-fluoropyrimidine (220 mg) and NMP (3.3 mL), and the reaction mixture was stirred at 80° C. for 1 hour. The reaction mixture was diluted with ethyl acetate, and washed with water. The organic layer was dried over anhydrous magnesium sulfate, and then concentrated under reduced pressure. The residue was purified by silica gel column chromatography (hexane-ethyl acetate) to obtain ethyl 3-[(2S)-4-(6-chloro-5-fluoropyrimidin-4-yl)-2-(methoxymethyl)piperazin-1-yl]propanoate (434 mg) as an oil.

Preparation Example 23

A mixture of 2,4-dichloro-3-fluoropyridine (800 mg), tert-butyl piperazine-1-carboxylate (1.8 g), potassium carbonate (2.7 g), and NMP (16 mL) was stirred at 80° C. overnight, and then was stirred at 100° C. for 4 hours. The reaction mixture was diluted with ethyl acetate and water. The organic layer was washed with water and saturated brine, dried over anhydrous sodium sulfate, and then concentrated under reduced pressure. The residue was purified by silica gel column chromatography (hexane-ethyl acetate) to obtain tert-butyl 4-(2-chloro-3-fluoropyridin-4-yl)piperazine-1-carboxylate (612 mg) as a solid.

Preparation Example 24

A mixture of benzyl piperazine-1-carboxylate (15 mL), tert-butyl acrylate (15 mL), and ethanol (50 mL) was stirred at 100° C. for 5 hours. The reaction mixture was diluted with diethyl ether (100 mL), water (50 mL), and 1 M hydrochloric acid (100 mL), and the aqueous layer was separated. Ethyl acetate (500 mL) and 1 M aqueous sodium hydroxide solution (100 mL) were added to the aqueous layer, the organic layer was separated, and the mixture was dried over anhydrous magnesium sulfate, and concentrated under reduced pressure to obtain benzyl 4-(3-tert-butoxy-3-oxopropyl)piperazine-1-carboxylate (29 g) as an oil.

Preparation Example 25

A mixture of tert-butyl (3 S)-3-(methoxymethyl)piperazine-1-carboxylate (633 mg), ethyl acrylate (0.39 mL), and ethanol (1.9 mL) was stirred at 80° C. for 3 hours under microwave irradiation. The reaction mixture was cooled to room temperature, and then was concentrated under reduced pressure, and the residue was purified by silica gel column chromatography (hexane-ethyl acetate) to obtain tert-butyl (3S)-4-(3-ethoxy-3-oxopropyl)-3-(methoxymethyl)piperazine-1-carboxylate (444 mg) as an oil.

Preparation Example 26

N-methylmorpholine (0.65 mL) was added to a mixture of tert-butyl (3R)-3-hydroxypyrrolidine-1-carboxylate (1.0 g), ethyl propiolate (1.9 mL), and methylene chloride (16 mL), and the reaction mixture was stirred at room temperature for 2.5 hours. The reaction mixture was concentrated under reduced pressure, and the residue was purified by silica gel column chromatography (hexane-ethyl acetate) to obtain tert-butyl (3R)-3-{[(1E)-3-ethoxy-3-oxoprop-1-en-1-yl]oxy}pyrrolidine-1-carboxylate (1.1 g) as an oil.

Preparation Example 27

10% palladium on carbon (414 mg, 50% water contained) was added to a mixture of tert-butyl (3R)-3-{[(1E)-3-ethoxy-3-oxoprop-1-en-1-yl]oxy}pyrrolidine-1-carboxylate (1.1 g), and ethanol (22 mL) under an argon atmosphere. The reaction mixture was stirred for 14 hours under a hydrogen atmosphere (1 atm). The reaction mixture was filtered through a celite pad, and the filtrate was concentrated under reduced pressure so as to obtain tert-butyl (3R)-3-(3-ethoxy-3-oxopropoxy)pyrrolidine-1-carboxylate (1.1 g) as an oil.

Preparation Example 28

A mixture of tert-butyl 4-(3-ethoxy-3-oxopropyl)-3-(hydroxymethyl)piperazine-1-carboxylate (1.0 g) and methylene chloride (10 mL) was added dropwise to a mixture of bis(2-methoxyethyl)aminosulfur trifluoride (0.81 mL) and methylene chloride (10 mL) at −70° C. for 20 minutes under a nitrogen atmosphere so that the internal temperature does not exceed −60° C. The reaction mixture was stirred at room temperature for 8 hours. To the reaction mixture was added a saturated aqueous sodium hydrogen carbonate solution, followed by extraction with chloroform. The organic layer was dried over anhydrous magnesium sulfate, and concentrated under reduced pressure. The residue was purified by silica gel column chromatography (chloroform) to obtain tert-butyl 4-(3-ethoxy-3-oxopropyl)-3-(fluoromethyl)piperazine-1-carboxylate (278 mg) as an oil.

Preparation Example 29

N,N-diisopropylethylamine (4.6 mL), and ethyl bromoacetate (2.1 mL) were added to a mixture of tert-butyl (3 S)-3-(methoxymethyl)piperazine-1-carboxylate (2.0 g) and methylene chloride (45 mL), and the reaction mixture was stirred at room temperature for 23 hours. The reaction mixture was added water so as to separate the organic layer, and concentrated under reduced pressure. The residue was purified by silica gel column chromatography (hexane-ethyl acetate) to obtain tert-butyl (3S)-4-(2-ethoxy-2-oxoethyl)-3-(methoxymethyl)piperazine-1-carboxylate (2.3 g) as an oil.

Preparation Example 30

4 M hydrogen chloride ethyl acetate solution (6.0 mL) was added to a mixture of tert-butyl (3S)-4-(3-ethoxy-3-oxopropyl)-3-methylpiperazine-1-carboxylate (1.2 g) and ethanol (6.0 mL), and stirred at 80° C. for 1.5 hours. The reaction liquid was cooled to room temperature and was stirred overnight. The solid was collected by filtration and dried to obtain ethyl 3-[(2S)-2-methylpiperazin-1-yl]propanoate dihydrochloride (995 mg) as a solid.

Preparation Example 31

4 M hydrogen chloride ethyl acetate solution (1.9 mL) was added to a mixture of tert-butyl (3 S)-4-(3-ethoxy-3-oxopropyl)-3-(methoxymethyl)piperazine-1-carboxylate (444 mg) and ethanol (2.2 mL), and the reaction mixture was stirred at room temperature for 2 hours. The reaction mixture was concentrated under reduced pressure to obtain ethyl 3-[(2S)-2-(methoxymethyl)piperazin-1-yl]propanoate dihydrochloride (401 mg) as a solid.

Preparation Example 32

A mixture of benzyl 4-(3-tert-butoxy-3-oxopropyl)piperazine-1-carboxylate (29 g), 10% palladium on carbon (6.0 g, 50% water contained), and ethanol (300 mL) was stirred at room temperature for 3 hours under a hydrogen atmosphere (1 atm). The reaction mixture was filtered through a celite pad, and the filtrate was concentrated under reduced pressure so as to obtain tert-butyl 3-(piperazin-1-yl)propanate (19 g) as an oil.

Preparation Example 33

A mixture of 1-[4-chloro-3-(trifluoromethyl)phenyl]ethanone (1.0 g), cyclopropylboronic acid (780 mg), dicyclohexyl(2',6'-dimethoxybiphenyl-2-yl)phosphine (185 mg), tripotassium phosphate (3.0 g), palladium acetate (II) (51 mg), toluene (10 mL), and water (1.0 mL) was stirred at 100° C. for 3 hours under an argon atmosphere, and then cooled to room temperature. Ethyl acetate and water were added to the reaction mixture, insoluble materials were removed by filtration, and then the filtrate was extracted with ethyl acetate. The organic layer was washed with saturated brine, dried over anhydrous magnesium sulfate, and concentrated under reduced pressure. The obtained residue was purified with silica gel column chromatography (hexane-ethyl acetate) to obtain 1-[4-cyclopropyl-3-(trifluoromethyl)phenyl]ethanone (1.0 g) as an oil.

Preparation Example 34

Trifluoroacetic acid (0.15 mL) was added to a mixture of zinc (2.0 g), cobalt bromide (II) (600 mg), and acetonitrile (30 mL) under an argon atmosphere, and the reaction mixture was stirred at room temperature for 15 minutes. 5-Bromo-1-fluoro-2-methoxy-3-(trifluoromethyl)benzene (5.0 g) and acetic anhydride (2.1 mL) were added to the reaction mixture, and the reaction mixture was stirred at room temperature for 17 hours. 1 M hydrochloric acid (30 mL) was added to the reaction mixture, and the mixture was extracted with diethyl ether. The organic layer was washed with water and saturated brine, and concentrated under reduced pressure. The obtained residue was purified by silica gel column chromatography (hexane-diethyl ether) to obtain 1-[3-fluoro-4-methoxy-5-(trifluoromethyl)phenyl]ethanone (1.6 g) as an oil.

Preparation Example 35

3 M methylmagnesium bromide diethyl ether solution (7.0 mL) was added to a mixture of N,6-dimethoxy-N-methyl-5-(trifluoromethyl)nicotinamide (3.7 g) and tetrahydrofuran (40 mL) under ice-cooling, and the reaction mixture was stirred for one hour. To the reaction mixture was added a saturated aqueous ammonium chloride solution, followed by extraction with ethyl acetate. The organic layer was dried over anhydrous magnesium sulfate, and concentrated under reduced pressure. The residue was purified by silica gel column chromatography (hexane-ethyl acetate) to obtain 1-[6-methoxy-5-(trifluoromethyl)pyridin-3-yl]ethanone (3.0 g) as an oil.

Preparation Example 36

Sodium hydride (90 mg, 60% oil dispersion) was added to a mixture of 5-{[(2R,5R)-2,5-dimethylpyrrolidin-1-yl]methyl}-4-[3-fluoro-5-(trifluoromethyl)phenyl]-1,3-thiazol-2-amine (300 mg), 4,6-dichloro-5-fluoropyrimidine (165 mg), and dehydrated tetrahydrofuran (6.0 mL) in an argon atmosphere under ice-methanol bath cooling, followed by stirring at 0° C. for 30 minutes. The resultant was extracted with ethyl acetate after adding ice water to the reaction mixture. The organic layer was washed with saturated brine, dried over anhydrous magnesium sulfate, and concentrated under reduced pressure. The obtained residue was purified by silica gel column chromatography (hexane-ethyl acetate) to obtain 6-chloro-N-(5-{[(2R,5R)-2,5-dimethylpyrrolidin-1-yl]methyl}-4-[3-fluoro-5-(trifluoromethyl)phenyl]-1,3-thiazol-2-yl)-5-fluoropyrimidin-4-amine (391 mg) as a solid.

Preparation Example 62

N,O-dimethylhydroxylamine hydrochloride (4.3 g), N-[3-(dimethylamino)propyl]-N'-ethylcarbodiimide hydrochloride (9.5 g), and N,N-diisopropylethylamine (30 mL) were added to a mixture of 6-methoxy-5-(trifluoromethyl)nicotinic acid (7.8 g) and methylene chloride (80 mL) under ice-cooling, and then the reaction mixture was stirred at room temperature for 17 hours. The reaction mixture was concentrated under reduced pressure, and to the residue were added ethyl acetate and water, followed by stirring for 30 minutes. The mixture was extracted with ethyl acetate, the organic layer was dried over anhydrous magnesium sulfate, and concentrated under reduced pressure. The obtained residue was purified by silica gel column chromatography (hexane-ethyl acetate) to N,6-dimethoxy-N-methyl-5-(trifluoromethyl)nicotinamide (5.0 g) as an oil.

Preparation Example 104

A mixture of methyl {[1-(6-chloro-5-fluoropyrimidin-4-yl)piperidin-4-yl]oxy}acetate (106 mg), 4-[3-fluoro-5-(trifluoromethyl)phenyl]-5-{[(2R)-2-methylpyrrolidin-1-yl]methyl}-1,3-thiazol-2-amine (125 mg), tris(dibenzylideneacetone) dipalladium (95 mg), 1,1'-binaphthalene-2,2'-diyl bis(diphenylphosphine) (130 mg), cesium carbonate (230 mg), and toluene (2.5 mL) was stirred at 100° C. for 6 hours under an argon atmosphere. The reaction mixture was concentrated under reduced pressure, and the residue was purified by silica gel column chromatography (hexane-ethyl acetate) and basic silica gel column chromatography (hexane-ethyl acetate) to obtain methyl [(1-{5-fluoro-6-[(4-[3-fluoro-5-(trifluoromethyl)phenyl]-5-{[(2R)-2-methylpyrrolidin-1-yl]methyl}-1,3-thiazol-2-yl)amino]pyrimidin-4-yl}piperidin-4-yl)oxy]acetate (57 mg) as a solid.

Preparation Example 135

Tripotassium phosphate (260 mg) was added to a mixture of ethyl 3-(4-{6-[(4-[3-bromo-5-(trifluoromethyl)phenyl]-5-{[(2R)-2-methylpyrrolidin-1-yl]methyl}-1,3-thiazol-2-yl)amino]-5-fluoropyrimidin-4-yl}piperazin-1-yl)propanoate (280 mg), 4,4,5,5-tetramethyl-2-(prop-1-en-2-yl)-1,3,2-dioxaborolane (135 mg), palladium acetate (II) (18 mg), tricyclohexylphosphine (45 mg), and dioxane (5.0 mL), and water (0.50 mL), and the reaction mixture was stirred at 95° C. for 6 hours. The reaction mixture was diluted with water, and then extracted with ethyl acetate. The organic layer was washed with saturated brine, dried over anhydrous magnesium sulfate, and concentrated under reduced pressure. The residue was purified by silica gel column chromatography (hexane-ethyl acetate) to obtain ethyl 3-(4-{5-fluoro-6-[(5-{[(2R)-2-methylpyrrolidin-1-yl]methyl}-4-[3-(prop-1-en-2-yl)-5-(trifluoromethyl)phenyl]-1,3-thiazol-2-yl)amino]pyrimidin-4-yl}piperazin-1-yl)propanoate (170 mg) as a solid.

Preparation Example 152

A mixture of 4-[3-fluoro-5-(trifluoromethyl)phenyl]-5-{[(2R)-2-methylpyrrolidin-1-yl]methyl}-1,3-thiazol-2-amine (500 mg), tert-butyl 4-(2-chloropyridin-4-yl)piperazine-1-carboxylate (500 mg), tris(dibenzylideneacetone) dipalladium (320 mg), di-tert-butyl(2',4',6'-triisopropylbiphenyl-2-yl)phosphine (350 mg), cesium carbonate (1.8 g), toluene (10 mL), and water (1.0 mL) was stirred at 100° C. for 1 hour under an argon atmosphere. The reaction mixture was cooled down to room temperature, and ethyl acetate and water were added. The mixture was extracted with ethyl acetate, the organic layer was dried over anhydrous sodium sulfate, and then concentrated under reduced pressure. The residue was purified by silica gel column chromatography (hexane-ethyl acetate) to obtain an oil (538 mg).

4 M hydrogen chloride dioxane solution (12 mL) was added to a mixture of the obtained oil (538 mg) and tetrahydrofuran (2.0 mL), and the reaction mixture was stirred at room temperature for 1 hour. The reaction mixture was concentrated under reduced pressure, and saturated aqueous sodium hydrogen carbonate solution (15 mL) and water were added to the residue. The mixture was extracted with chloroform-isopropanol, the organic layer was dried over anhydrous sodium sulfate, and concentrated under reduced pressure. The residue was purified by silica gel column chromatography (chloroform-methanol) to obtain N-(4-[3-fluoro-5-(trifluoromethyl)phenyl]-5-{[(2R)-2-methylpyrrolidin-1-yl]methyl}-1,3-thiazol-2-yl)-4-(piperazin-1-yl)pyridin-2-amine (300 mg) as a solid.

Preparation Example 189

A mixture of N-{4-[4-chloro-3-(trifluoromethyl)phenyl]-1,3-thiazol-2-yl}acetamide (5.5 g), acetic acid (55 mL), 36% formaldehyde aqueous solution (6.8 mL) and acetic anhydride (5.0 mL) was stirred at 170° C. for 30 minutes under microwave irradiation. The reaction mixture was concentrated under reduced pressure. Isopropanol was added to the obtained residue, and the precipitated solid was collected by filtration and dried to obtain methyl {2-acetamide-4-[4-chloro-3-(trifluoromethyl)phenyl]-1,3-thiazole-5-yl}acetate (4.1 g) as a solid.

Preparation Example 196

A mixture of 4-[4-chloro-3-(trifluoromethyl)phenyl]-1,3-thiazol-2-amine (6.0 g), pyridine (36 mL), and acetic anhydride (9.0 mL) was stirred at 60° C. for 4 hours. Water was added to the reaction mixture, and the generated solid was collected by filtration and dried under reduced pressure to obtain N-{4-[4-chloro-3-(trifluoromethyl)phenyl]-1,3-thiazol-2-yl}acetamide (5.5 g) as a solid.

Preparation Example 213

Phenyltrimethylammonium tribromide (44 g) was added to a mixture of 1-[4-chloro-3-(trifluoromethyl)phenyl]ethanone (25 g) and tetrahydrofuran (300 mL), and the reaction mixture was stirred at room temperature for 2 hours. The insoluble materials were separated by filtration, and the filtrate was concentrated under reduced pressure. The obtained compound and ethanol (300 mL) were mixed, and thiourea (10 g) was added to the mixture, and then was stirred at 80° C. for 5 hours. The reaction mixture was cooled to room temperature, and the precipitated solid was collected by filtration. The filtrate was concentrated under reduced pressure, and the precipitated solid was washed with ethyl acetate, and was collected by filtration. This solid was combined with the solid which was previously collected by filtration, and the combined solid was dispersed into ethyl acetate and a saturated aqueous sodium hydrogen carbonate solution so as to extract with ethyl acetate. The organic layer was washed with water and saturated brine, dried over anhydrous sodium sulfate, and then concentrated under reduced pressure. The obtained solid was washed with hexane, collected by filtration, and dried to obtain 4-[4-chloro-3-(trifluoromethyl)phenyl]-1,3-thiazol-2-amine (24 g) as a solid.

Preparation Example 228

Methyl (piperidin-4-yl-oxy)acetate hydrochloride (151 mg) and N,N-diisopropylethylamine (0.60 mL) were sequentially added to a mixture of 4,6-dichloro-5-fluoropyrimidine (120 mg) and NMP (1.8 mL), and then the reaction mixture was stirred at 80° C. for 2 hours. The reaction liquid was diluted with ethyl acetate, and washed with water. The organic layer was dried over anhydrous magnesium sulfate, and then concentrated under reduced pressure. The residue was purified by silica gel column chromatography (hexane-ethyl acetate) to obtain methyl {[1-(6-chloro-5-fluoropyrimidin-4-yl)piperidin-4-yl]oxy}acetate (217 mg) as an oil.

Example 1

1 M aqueous sodium hydroxide solution (1.7 mL) was added to a mixture of ethyl 3-[(2S)-4-{6-[(4-[4-chloro-3-(trifluoromethyl)phenyl]-5-{[(2R)-2-methylpyrrolidin-1-yl]methyl}-1,3-thiazol-2-yl)amino]-5-fluoropyrimidin-4-yl}-2-(methoxymethyl)piperazin-1-yl]propanoate (192 mg), ethanol (1.0 mL), and tetrahydrofuran (1.0 mL), and the reaction mixture was stirred at room temperature for 2 hours. To the reaction mixture was added 1 M hydrochloric acid (1.7 mL) for neutralization, followed by extraction with chloroform-isopropanol (4:1). The organic layer was dried over anhydrous magnesium sulfate, and then concentrated under reduced pressure. Tetrahydrofuran (5.0 mL) and 4 M hydrogen chloride dioxane solution (0.28 mL) were added to the residue. The mixture was concentrated under reduced pressure to obtain 3-[(2S)-4-{6-[(4-[4-chloro-3-(trifluoromethyl)phenyl]-5-{[(2R)-2-methylpyrrolidin-1-yl]methyl}-1,3-thiazol-2-yl)amino]-5-fluoropyrimidin-4-yl}-2-(methoxymethyl)piperazin-1-yl]propanoic acid trihydrochloride (160 mg) as a solid.

Example 2

A mixture of ethyl 3-(4-{2-[(4-[4-chloro-3-(trifluoromethyl)phenyl]-5-{[(2R)-2-methylpyrrolidin-1-yl]methyl}-1,3-thiazol-2-yl)amino]-3-fluoropyridin-4-yl}piperazin-1-yl) propanoate (137 mg), tetrahydrofuran (3.0 mL), ethanol (3.0 mL), and 1 M aqueous sodium hydroxide solution (1.2 mL) was stirred at 60° C. for 2.5 hours. The reaction mixture was concentrated under reduced pressure, and the obtained residue was purified by ODS column chromatography (acetonitrile-water) to obtain sodium 3-(4-{2-[(4-[4-chloro-3-(trifluoromethyl)phenyl]-5-{[(2R)-2-methylpyrrolidin-1-yl]methyl}-1,3-thiazol-2-yl)amino]-3-fluoropyridin-4-yl}piperazin-1-yl)propanoate (103 mg) as a solid.

Example 3

A mixture of 6-chloro-N-(4-[3-fluoro-5-(trifluoromethyl)phenyl]-5-{[(2R)-2-methylpyrrolidin-1-yl]methyl}-1,3-thiazol-2-yl)-2-methylpyrimidin-4-amine (453 mg), N,N-diisopropylethylamine (2.0 mL), ethyl 3-(piperazin-1-yl)propanoate dihydrochloride (750 mg), and NMP (10 mL) was stirred at 80° C. for 1 hour. N,N-diisopropylethylamine (2.0 mL) and ethyl 3-(piperazin-1-yl)propanoate dihydrochloride (750 mg) were added to the reaction mixture, and the reaction mixture was stirred at 80° C. overnight. Water and ethyl acetate were added to the reaction liquid so as to separate the organic layer. The organic layer was washed with water, dried over anhydrous magnesium sulfate, and then concentrated under reduced pressure. The residue was purified by silica gel column chromatography (hexane-ethyl acetate) to obtain ethyl 3-(4-{6-[(4-[3-fluoro-5-(trifluoromethyl)phenyl]-5-{[(2R)-2-methylpyrrolidin-1-yl]methyl}-1,3-thiazol-2-yl)amino]-2-methylpyrimidin-4-yl}piperazin-1-yl)propanoate as a solid.

1 M aqueous sodium hydroxide solution (5.0 mL) was added to a mixture of the obtained solid, tetrahydrofuran (5.0 mL), and ethanol (5.0 mL), and the reaction mixture was stirred at 60° C. for 1 hour. 1 M hydrochloric acid (5.0 mL), chloroform, and methanol were added to the reaction mixture so as to separate the organic layer. The organic layer was washed with water, dried over anhydrous magnesium sulfate, and then concentrated under reduced pressure. The residue was purified by silica gel column chromatography (chloroform-methanol) twice to obtain a solid. 4 M hydrogen chloride dioxane solution (0.70 mL) was added to a mixture of the obtained solid and ethyl acetate, and the mixture was concentrated under reduced pressure. The residue was washed with ethyl acetate, and dried over under the reduced pressure to obtain 3-(4-{6-[(4-[3-fluoro-5-(trifluoromethyl)phenyl]-5-{[(2R)-2-methyl pyrrolidin-1-yl]methyl}-1,3-thiazol-2-yl)amino]-2-methylpyrimidin-4-yl}piperazin-1-yl)propanoic acid trihydrochloride (525 mg) as a solid.

Example 4

A mixture of 6-chloro-N-(5-{[(2R,5R)-2,5-dimethyl pyrrolidin-1-yl]methyl}-4-[3-fluoro-5-(trifluoromethyl)phenyl]-1,3-thiazol-2-yl)-5-fluoro-2-methylpyrimidin-4-amine (392 mg), ethyl 3-(piperazin-1-yl)propanoate dihydrochloride (590 mg), N,N-diisopropylethylamine (1.3 mL), and NMP (6.0 mL) was stirred at 80° C. for 2 hours. The reaction mixture was cooled to room temperature, and then water and ethyl acetate were added thereto. The organic layer was washed with water, dried over anhydrous magnesium sulfate, and then concentrated under reduced pressure. The residue was purified by silica gel column chromatography (hexane-ethyl acetate) twice to obtain ethyl 3-(4-{6-[(5-{[(2R,5R)-2,5-dimethylpyrrolidin-1-yl]methyl}-4-[3-fluoro-5-(trifluoromethyl)phenyl]-1,3-thiazol-2-yl)amino]-5-fluoro-2-methylpyrimidin-4-yl}piperazin-1-yl)propanoate as an oil (243 mg).

1 M aqueous sodium hydroxide solution (2.0 mL) was added to a mixture of the obtained oil (243 mg) and ethanol (4.0 mL) and tetrahydrofuran (4.0 mL), and the reaction mixture was stirred at 50° C. for 30 minutes. The reaction mixture was cooled to room temperature, and then concentrated under reduced pressure. The residue was purified by ODS column chromatography (acetonitrile-water) to obtain sodium 3-(4-{6-[(5-{[(2R,5R)-2,5-dimethylpyrrolidin-1-yl]methyl}-4-[3-fluoro-5-(trifluoromethyl)phenyl]-1,3-thiazol-2-yl)amino]-5-fluoro-2-methylpyrimidin-4-yl}piperazin-1-yl)propanoate (149 mg) as a solid.

Example 5

A mixture of tert-butyl 3-(4-{3-fluoro-2-[(4-[3-fluoro-5-(trifluoromethyl)phenyl]-5-{[(2R)-2-methylpyrrolidin-1-yl]

methyl}-1,3-thiazol-2-yl)amino]pyridin-4-yl}piperazin-1-yl)propanoate (387 mg), and 4 M hydrogen chloride dioxane solution (18 mL) was stirred at room temperature overnight. The reaction mixture was concentrated under reduced pressure. The obtained residue was washed with ethyl acetate, and was dried over under reduced pressure to obtain 3-(4-{3-fluoro-2-[(4-[3-fluoro-5-(trifluoromethyl)phenyl]-5-{[(2R)-2-methylpyrrolidin-1-yl]methyl}-1,3-thiazol-2-yl)amino]pyridin-4-yl}piperazin-1-yl)propanoic acid trihydrochloride (394 mg) as a solid.

Example 6

A mixture of tert-butyl 4-(2-chloropyridin-4-yl)piperazine-1-carboxylate (300 mg), 4-[4-chloro-3-(trifluoromethyl)phenyl]-5-{[(2R)-2-methylpyrrolidin-1-yl]methyl}-1,3-thiazol-2-amine (322 mg), (9,9-dimethyl-9H-xanthene-4,5-diyl) bis(diphenylphosphine) (500 mg), cesium carbonate (1.2 g), tris(dibenzylideneacetone) dipalladium (400 mg), toluene (7.0 mL), and water (0.70 mL) was stirred at 100° C. for 4 hours under argon atmosphere. The reaction mixture was cooled to room temperature, and then to the reaction mixture was added water and ethyl acetate, followed by extraction with ethyl acetate. The organic layer was washed with saturated brine, dried over anhydrous sodium sulfate, and then concentrated under reduced pressure. The residue was purified by silica gel column chromatography (hexane-ethyl acetate) to obtain an oil (412 mg).

4 M hydrogen chloride dioxane solution (6.0 mL) was added to a mixture of the obtained oil (412 mg) and tetrahydrofuran (1.0 mL), and then was stirred at room temperature for 3 hours. The reaction mixture was concentrated under reduced pressure, and to the obtained residue was added a saturated aqueous sodium hydrogen carbonate solution, followed by extraction with chloroform-isopropanol. The organic layer was dried over anhydrous sodium sulfate, and then concentrated under reduced pressure. The residue was purified by silica gel column chromatography (chloroform-methanol) to obtain an oil (323 mg).

Ethyl acrylate (0.13 mL) was added to a mixture of the obtained oil (323 mg) and ethanol (5.0 mL), and then was stirred at 100° C. for 30 minutes in a sealed tube under microwave irradiation. The reaction mixture was concentrated under reduced pressure, and the obtained residue was purified by basic silica gel column chromatography (hexane-ethyl acetate) to obtain ethyl 3-(4-{2-[(4-[4-chloro-3-(trifluoromethyl)phenyl]-5-{[(2R)-2-methylpyrrolidin-1-yl]methyl}-1,3-thiazol-2-yl)amino]pyridin-4-yl}piperazin-1-yl)propanoate as an oil (168 mg).

1 M aqueous sodium hydroxide solution (1.5 mL) was added to a mixture of the obtained oil (168 mg) and ethanol (2.0 mL) and tetrahydrofuran (2.0 mL), and then was stirred at 50° C. for 30 minutes. The reaction mixture was cooled to room temperature, and then to the reaction mixture was added 1 M hydrochloric acid (1.5 mL) and water (20 mL), followed by extraction with chloroform-isopropanol. The organic layer was dried over anhydrous magnesium sulfate, and then concentrated under reduced pressure. 4 M hydrogen chloride dioxane solution (2.0 mL) was added to a mixture of the obtained residue and tetrahydrofuran (20 mL), and then concentrated under reduced pressure. Acetonitrile and water were added to the residue, and the obtained solid was collected by filtration, was washed with acetonitrile, and then dried at 50° C. under the reduced pressure to obtain 3-(4-{2-[(4-[4-chloro-3-(trifluoromethyl)phenyl]-5-{[(2R)-2-methylpyrrolidin-1-yl]methyl}-1,3-thiazol-2-yl)amino]pyridin-4-yl}piperazin-1-yl)propanoic acid trihydrochloride (118 mg) as a solid.

Example 7

1 M aqueous sodium hydroxide solution (1.5 mL) was added to a mixture of ethyl 3-(4-{5-fluoro-6-[(4-[6-methoxy-5-(trifluoromethyl)pyridin-3-yl]-5-{[(2R)-2-methylpyrrolidin-1-yl]methyl}-1,3-thiazol-2-yl)amino]pyrimidin-4-yl}piperazin-1-yl)propanoate (325 mg) and methanol (3.0 mL), and the reaction mixture was stirred at room temperature for 3 hours. Acetic acid (0.086 mL) was added to the reaction mixture. To the obtained mixture was added water and chloroform-isopropanol (3:1), followed by stirring. The organic layer was separated, and the aqueous layer was extracted with chloroform-isopropanol (3:1). The organic layers were combined, dried over anhydrous sodium sulfate, and then concentrated under reduced pressure. To the residue was added acetonitrile (5.0 mL), followed by stirring at room temperature for 1 hour. The solid was collected by filtration, and then was dried over under reduced pressure to obtain 3-(4-{5-fluoro-6-[(4-[6-methoxy-5-(trifluoromethyl)pyridin-3-yl]-5-{[(2R)-2-methylpyrrolidin-1-yl]methyl}-1,3-thiazol-2-yl)amino]pyrimidin-4-yl}piperazin-1-yl)propanoic acid (270 mg) as a solid.

Example 8

A mixture of 6-chloro-N-(5-{[(2R,5R)-2,5-dimethylpyrrolidin-1-yl]methyl}-4-[3-fluoro-5-(trifluoromethyl)phenyl]-1,3-thiazol-2-yl)-5-fluoropyrimidin-4-amine (373 mg), ethyl 3-(piperazin-1-yl)propanoate dihydrochloride (580 mg), N,N-diisopropylethylamine (1.3 mL), and NMP (6.0 mL) was stirred at 80° C. for two hours. The reaction mixture was cooled to room temperature, and then water and ethyl acetate were added thereto. The organic layer was washed with water, dried over anhydrous magnesium sulfate, and then concentrated under reduced pressure. The residue was purified by silica gel column chromatography (hexane-ethyl acetate) twice to obtain ethyl 3-(4-{6-[(5-{[(2R,5R)-2,5-dimethylpyrrolidin-1-yl]methyl}-4-[3-fluoro-5-(trifluoromethyl)phenyl]-1,3-thiazol-2-yl)amino]-5-fluoropyrimidin-4-yl}piperazin-1-yl)propanoate (257 mg) as an oil.

1 M aqueous sodium hydroxide solution (2.0 mL) was added to a mixture of the obtained oil (257 mg), ethanol (4.0 mL), and tetrahydrofuran (4.0 mL) was stirred at 50° C. for 30 minutes. The reaction mixture was cooled to room temperature, and then concentrated under reduced pressure.

The residue was purified by ODS column chromatography (acetonitrile-water) to obtain sodium 3-(4-{6-[(5-{[(2R,5R)-2,5-dimethylpyrrolidin-1-yl]methyl}-4-[3-fluoro-5-(trifluoromethyl)phenyl]-1,3-thiazol-2-yl)amino]-5-fluoropyrimidin-4-yl}piperazin-1-yl)propanoate (189 mg) as a solid.

Example 9

1 M aqueous sodium hydroxide solution (1.0 mL) was added to a mixture of ethyl 3-(4-{6-[(4-[4-chloro-3-(trifluoromethyl)phenyl]-5-{[(2R)-2-methylpyrrolidin-1-yl]methyl}-1,3-thiazol-2-yl)amino]-5-fluoropyrimidin-4-yl}piperazin-1-yl)propanoate (195 mg), ethanol (1.0 mL), and tetrahydrofuran (2.0 mL), and the reaction mixture was stirred at room temperature for 3.5 hours. The reaction mixture was diluted with ice-water containing 1 M hydrochloric acid (1.1 mL) and a saturated aqueous ammonium chloride solution and was extracted with ethyl acetate-isopropanol (4:1). The organic layer was washed with saturated brine, dried over anhydrous magnesium sulfate, and concentrated under reduced pressure. To the residue was added to tetrahydrofuran (8.0 mL) and 4 M hydrogen chloride dioxane solution (1.0 mL), followed by stirring at room temperature for 30 minutes. The reaction mixture was concentrated under reduced pressure, and the obtained residue was washed with diethyl ether, and dried over under reduced pressure to obtain 3-(4-{6-[(4-[4-chloro-3-(trifluoromethyl)phenyl]-5-{[(2R)-2-methylpyrrolidin-1-yl]methyl}-1,3-thiazol-2-yl)amino]-5-fluoropyrimidin-4-yl}piperazin-1-yl)propanoic acid trihydrochloride (193 mg) as a solid.

Example 10

1 M aqueous sodium hydroxide solution (1.6 mL) was added to a mixture of ethyl 3-[(2S)-4-{5-fluoro-6-[(4-[3-fluoro-5-(trifluoromethyl)phenyl]-5-{[(2R)-2-methylpyrrolidin-1-yl]methyl}-1,3-thiazol-2-yl)amino]pyrimidin-4-yl}-2-(methoxymethyl)piperazin-1-yl]propanoate (172 mg), ethanol (1.4 mL), and tetrahydrofuran (1.4 mL), and the reaction mixture was stirred at 60° C. for one hour. To the reaction mixture was added 1 M hydrochloric acid (1.6 mL) for neutralization, followed by extraction with chloroform-isopropanol (4:1). The organic layer was dried over anhydrous magnesium sulfate, and then concentrated under reduced pressure. Tetrahydrofuran (5.0 mL) and 4 M hydrogen chloride dioxane solution (0.25 mL) were added to the residue. The mixture was concentrated under reduced pressure to obtain 3-[(2S)-4-{5-fluoro-6-[(4-[3-fluoro-5-(trifluoromethyl)phenyl]-5-{[(2R)-2-methylpyrrolidin-1-yl]methyl}-1,3-thiazol-2-yl)amino]pyrimidin-4-yl}-2-(methoxymethyl)piperazin-1-yl]propanoic acid trihydrochloride (180 mg) as a solid.

Example 11

1 M aqueous sodium hydroxide solution (0.75 mL) was added to a mixture of ethyl 3-(4-{6-[(4-[3-chloro-5-(trifluoromethyl)phenyl]-5-{[(2R)-2-methylpyrrolidin-1-yl]methyl}-1,3-thiazol-2-yl)amino]-5-fluoropyrimidin-4-yl}piperazin-1-yl)propanoate (150 mg), ethanol (0.75 mL), and tetrahydrofuran (1.5 mL), and the reaction mixture was stirred at room temperature for 3.5 hours. The reaction mixture was diluted with ice-water containing 1 M hydrochloric acid (0.75 mL) and a saturated aqueous ammonium chloride solution and was extracted with chloroform-isopropanol (4:1). The organic layer was washed with saturated brine, dried over anhydrous magnesium sulfate, and then concentrated under reduced pressure. Tetrahydrofuran (4.0 mL) and 4 M hydrogen chloride dioxane solution (0.75 mL) were added to the residue under an argon atmosphere, and the reaction mixture was stirred at room temperature for 30 minutes. The reaction mixture was concentrated under reduced pressure to obtain 3-(4-{6-[(4-[3-chloro-5-(trifluoromethyl)phenyl]-5-{[(2R)-2-methylpyrrolidin-1-yl]methyl}-1,3-thiazol-2-yl)amino]-5-fluoropyrimidin-4-yl}piperazin-1-yl)propanoic acid trihydrochloride (152 mg) as a solid.

Example 12

1 M aqueous sodium hydroxide solution (0.58 mL) was added to a mixture of methyl [(1-{5-fluoro-6-[(4-[3-fluoro-5-(trifluoromethyl)phenyl]-5-{[(2R)-2-methylpyrrolidin-1-yl]methyl}-1,3-thiazol-2-yl)amino]pyrimidin-4-yl}piperidin-4-yl)oxy]acetate (57 mg), ethanol (0.42 mL), and tetrahydrofuran (0.42 mL), and the reaction mixture was stirred at 60° C. for 1 hour. To the reaction mixture was added 1 M hydrochloric acid (0.58 mL) for neutralization, followed by extraction with chloroform-isopropanol (4:1). The organic layer was dried over anhydrous magnesium sulfate, and then concentrated under reduced pressure. Tetrahydrofuran (5.0 mL) and 4 M hydrogen chloride dioxane solution (0.090 mL) were added to the residue. The mixture was concentrated under reduced pressure to obtain [(1-{5-fluoro-6-[(4-[3-fluoro-5-(trifluoromethyl)phenyl]-5-{[(2R)-2-methylpyrrolidin-1-yl]methyl}-1,3-thiazol-2-yl)amino]pyrimidin-4-yl}piperidin-4-yl)oxy]acetic acid dihydrochloride (60 mg) as a solid.

Example 13

1 M aqueous sodium hydroxide solution (1.3 mL) was added to a mixture of ethyl [(1-{6-[(4-[3-chloro-5-(trifluoromethyl)phenyl]-5-{[(2R)-2-ethylpyrrolidin-1-yl]methyl}-1,3-thiazol-2-yl)amino]-5-fluoropyrimidin-4-yl}piperidin-4-yl)oxy]acetate (172 mg), ethanol (2.0 mL), and tetrahydrofuran (2.0 mL), and the reaction mixture was stirred at room temperature for 2 hours. The reaction mixture was purified by ODS column chromatography (0.1% formic acid-acetonitrile). Tetrahydrofuran (4.0 ml) and 4 M hydrogen chloride dioxane solution (0.70 ml) were added to the obtained residue. The reaction mixture was concentrated under reduced pressure, and the obtained residue was washed with diethyl ether, and then was dried over under reduced pressure to obtain [(1-{6-[(4-[3-chloro-5-(trifluoromethyl)phenyl]-5-{[(2R)-2-ethylpyrrolidin-1-yl]methyl}-1,3-thiazol-2-yl)amino]-5-fluoropyrimidin-4-yl}piperidin-4-yl)oxy]acetic acid dihydrochloride (34 mg) as a solid.

Compounds of Preparation Examples and Examples, which were indicated in the following tables, were produced by using the same method as that of the Preparation Examples or Examples.

TABLE 5
| PEx | PSyn | Str | DAT |
|---|---|---|---|
| 1 | 1 | 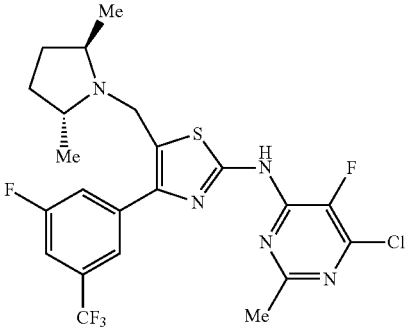 [SMILES: Cc1nc(Cl)c(F)c(Nc2nc(-c3cc(F)cc(C(F)(F)F)c3)c(CN3[C@H](C)CC[C@H]3C)s2)n1] | ESI+: 518, 520 |
| 2 | 2 | 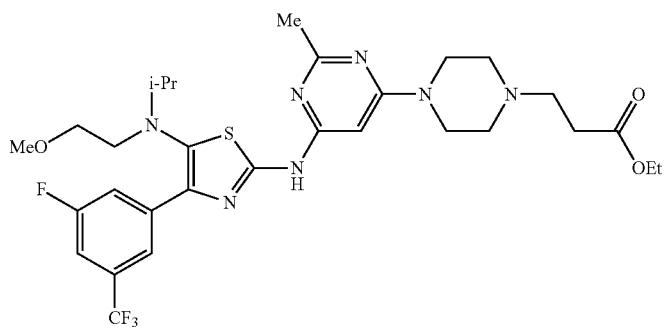 [SMILES: CCOC(=O)CCN1CCN(c2cc(Nc3nc(-c4cc(F)cc(C(F)(F)F)c4)c(N(CCOC)C(C)C)s3)nc(C)n2)CC1] | APCI/ESI+: 654 |
| 3 | 3 | 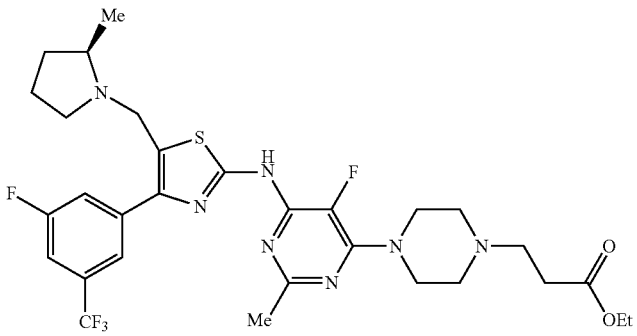 [SMILES: CCOC(=O)CCN1CCN(c2nc(C)nc(Nc3nc(-c4cc(F)cc(C(F)(F)F)c4)c(CN4CCC[C@H]4C)s3)c2F)CC1] | APCI/ESI+: 654 |
TABLE 6
| PEx | PSyn | Str | DAT |
|---|---|---|---|
| 4 | 4 | 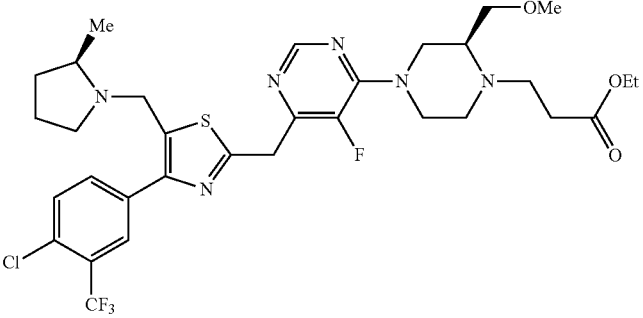 [SMILES: CCOC(=O)CCN1CCN(c2ncnc(Cc3nc(-c4ccc(Cl)c(C(F)(F)F)c4)c(CN4CCC[C@H]4C)s3)c2F)C[C@H]1COC] | ESI−: 698, 700 |

TABLE 6-continued
| PEx | PSyn | Str | DAT |
|---|---|---|---|
| 5 | 5 | 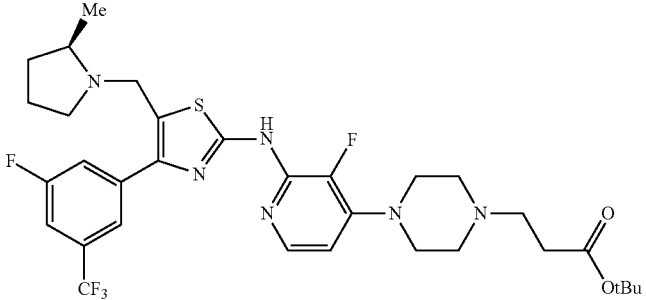 [SMILES: C[C@@H]1CCCN1Cc1sc(Nc2nccc(N3CCN(CCC(=O)OC(C)(C)C)CC3)c2F)nc1-c1cc(F)cc(C(F)(F)F)c1] | APCI/ESI+: 667 |
| 6 | 6 | 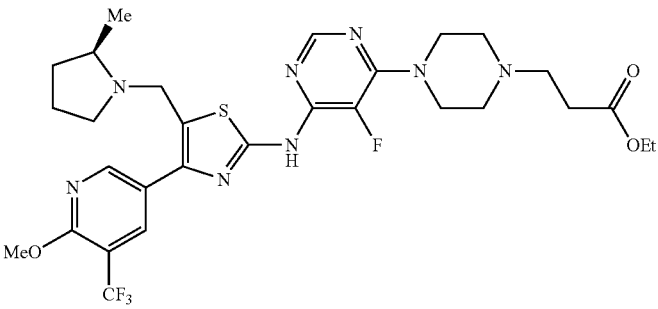 | ESI+: 653 |
| 7 | 7 | 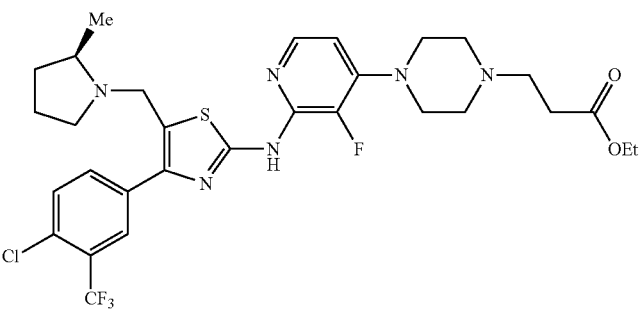 [SMILES: CCOC(=O)CCN1CCN(c2ccnc(Nc3nc(-c4ccc(Cl)c(C(F)(F)F)c4)c(CN4CCC[C@H]4C)s3)c2F)CC1] | APCI/ESI+: 656 |
TABLE 7
| PEx | PSyn | Str | DAT |
|---|---|---|---|
| 8 | 8 | 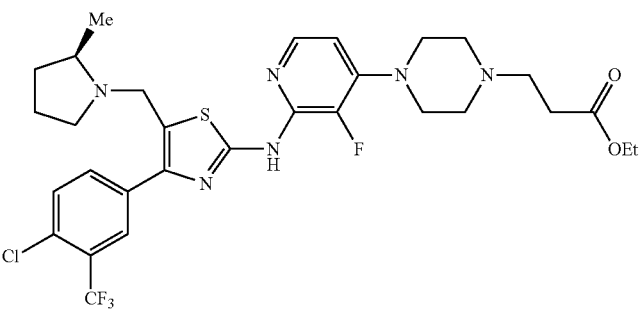 [SMILES: CCOC(=O)CCN1CCN(c2ccnc(Nc3nc(-c4ccc(Cl)c(C(F)(F)F)c4)c(CN4CCC[C@H]4C)s3)c2F)CC1] | APCI/ESI+: 655 |

TABLE 7-continued

| PEx | PSyn | Str | DAT |
|---|---|---|---|
| 9 | 9 | | APCI/ESI+: 555 |
| 10 | 10 | | ESI+: 584 3HCl |
| 11 | 11 | | ESI+: 376, 378 |

| TABLE 8 | | | | | TABLE 8-continued | | | |
|---|---|---|---|---|---|---|---|---|
| PEx | PSyn | Str | DAT | | PEx | PSyn | Str | DAT |
| 12 | 12 | | ESI+: 360 | | 13 | 13 | | ESI+: 374 |

TABLE 8-continued

| PEx | PSyn | Str | DAT |
|---|---|---|---|
| 14 | 14 | (structure) | ESI+: 402 |

TABLE 9

| PEx | PSyn | Str | DAT |
|---|---|---|---|
| 15 | 15 | (structure) | ESI+: 416 |

TABLE 9-continued

| PEx | PSyn | Str | DAT |
|---|---|---|---|
| 16 | 16 | (structure) | ESI+: 418, 420 |
| 17 | 17 | (structure) | ESI+: 377 |
| 18 | 18 | (structure) | APCI/ESI+: 409 |

TABLE 10

| PEx | PSyn | Str | DAT |
|---|---|---|---|
| 19 | 19 | (structure) | ESI+: 305 |
| 20 | 20 | (structure) | APCI/ESI+: 378 |
| 21 | 21 | (structure) | ESI+: 263 |

TABLE 10-continued

| PEx | PSyn | Str | DAT |
|---|---|---|---|
| 22 | 22 | | ESI+: 361, 363 |
| 23 | 23 | | ESI+: 316, 318 |
| 24 | 24 | | APCI/ESI+: 349 |

TABLE 11

| PEx | PSyn | Str | DAT |
|---|---|---|---|
| 25 | 25 | | ESI+: 331 |
| 26 | 26 | | ESI+: 308[(M + Na)+] |
| 27 | 27 | | NMR-CDCl3: 1.26 (3 H, t, J = 7.2 Hz), 1.46 (9 H, s), 1.83-2.04 (2 H, m), 2.55 (2 H, t, J = 6.5 Hz), 3.30-3.47 (4 H, m), 3.65-3.75 (2 H, m), 3.99-4.07 (1 H, m), 4.15 (2 H, q, J = 7.2 Hz) |
| 28 | 28 | | ESI+: 319 |
| 29 | 29 | | ESI+: 317 |

TABLE 11-continued
| PEx | PSyn | Str | DAT |
|---|---|---|---|
| 30 | 30 | 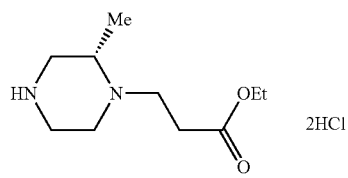 [SMILES: CCOC(=O)CCN1CCNC[C@@H]1C] 2HCl | ESI+: 201 |
TABLE 12
| PEx | PSyn | Str | DAT |
|---|---|---|---|
| 31 | 31 | 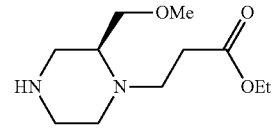 2HCl | ESI+: 231 |
| 32 | 32 | 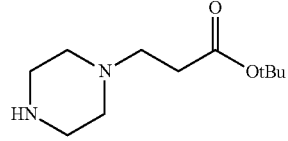 [SMILES: CC(C)(C)OC(=O)CCN1CCNCC1] | ESI+: 215 |
| 33 | 33 | 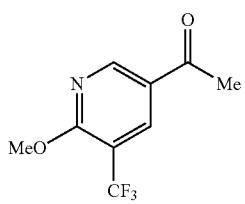 [SMILES: COc1ncc(C(C)=O)cc1C(F)(F)F] | EI+: 228[M+] |
| 34 | 34 | 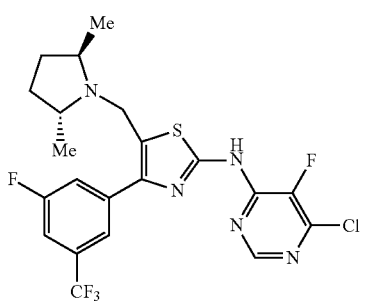 [SMILES: C[C@@H]1CC[C@@H](C)N1Cc1sc(Nc2ncnc(Cl)c2F)nc1-c1cc(F)cc(C(F)(F)F)c1] | ESI+: 237 |
| 35 | 35 | 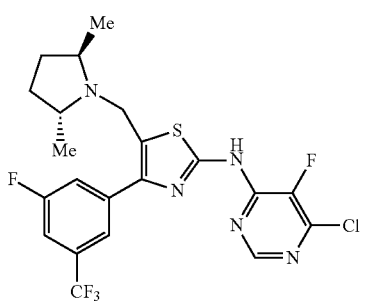 [SMILES: C[C@@H]1CC[C@@H](C)N1Cc1sc(Nc2ncnc(Cl)c2F)nc1-c1cc(F)cc(C(F)(F)F)c1] | ESI+: 220 |
| 36 | 36 | 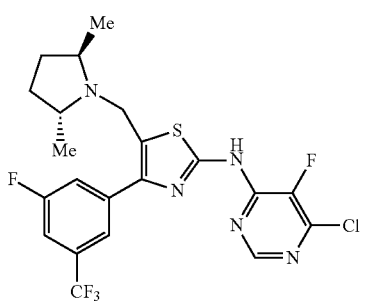 [SMILES: C[C@@H]1CC[C@@H](C)N1Cc1sc(Nc2ncnc(Cl)c2F)nc1-c1cc(F)cc(C(F)(F)F)c1] | ESI+: 504, 506 |
TABLE 13
| PEx | PSyn | Str | DAT |
|---|---|---|---|
| 37 | 1 | 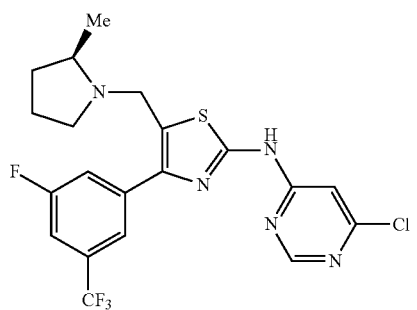 [SMILES: C[C@@H]1CCCN1Cc1sc(Nc2cc(Cl)ncn2)nc1-c1cc(F)cc(C(F)(F)F)c1] | ESI+: 472, 474 |

TABLE 13-continued
| PEx | PSyn | Str | DAT |
|---|---|---|---|
| 38 | 1 | | ESI+: 486, 488 |
| 39 | 1 | | APCI/ESI+: 502, 504 |
TABLE 14
| PEx | PSyn | Str | DAT |
|---|---|---|---|
| 40 | 1 | | APCI/ESI+: 504 |
| 41 | 1 | | APCI/ESI+: 490 |
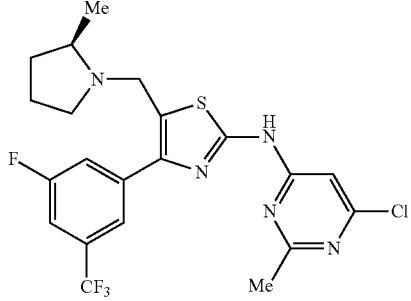 [SMILES: Cc1nc(Cl)cc(Nc2nc(-c3cc(F)cc(C(F)(F)F)c3)c(CN3CCC[C@H]3C)s2)n1]

TABLE 14-continued
| PEx | PSyn | Str | DAT |
|---|---|---|---|
| 42 | 1 | 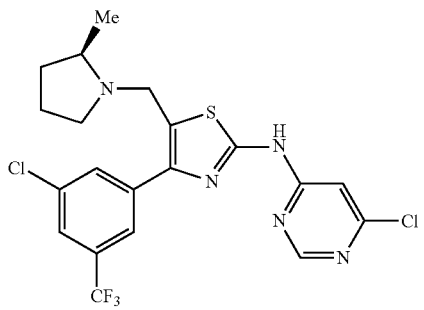 [SMILES: C[C@@H]1CCCN1Cc1sc(Nc2cc(Cl)ncn2)nc1-c1cc(Cl)cc(C(F)(F)F)c1] | ESI+: 488, 490 |
TABLE 15
| PEx | PSyn | Str | DAT |
|---|---|---|---|
| 43 | 1 | 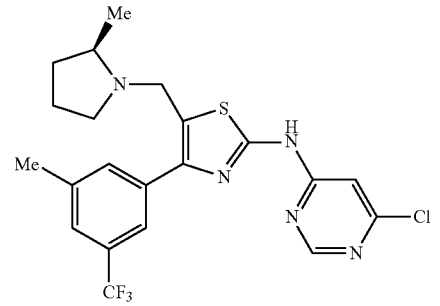 [SMILES: Cc1cc(-c2nc(Nc3cc(Cl)ncn3)sc2CN2CCC[C@H]2C)cc(C(F)(F)F)c1] | ESI+: 468, 470 |
| 44 | 1 | 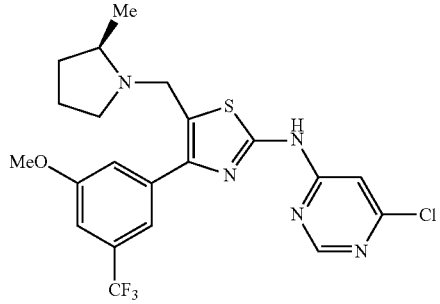 [SMILES: COc1cc(-c2nc(Nc3cc(Cl)ncn3)sc2CN2CCC[C@H]2C)cc(C(F)(F)F)c1] | ESI+: 484, 486 |
| 45 | 1 | 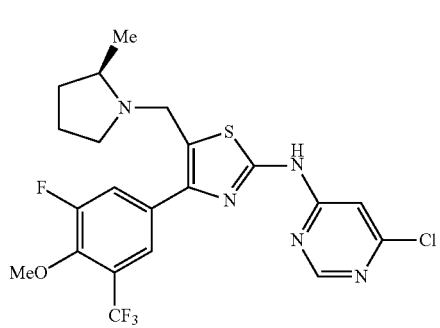 [SMILES: COc1c(F)cc(-c2nc(Nc3cc(Cl)ncn3)sc2CN2CCC[C@H]2C)cc1C(F)(F)F] | ESI+: 502, 504 |

TABLE 15-continued
| PEx | PSyn | Str | DAT |
|---|---|---|---|
| 46 | 1 | 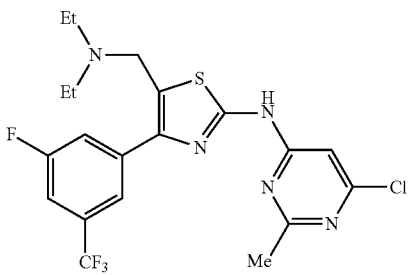 [SMILES: CCN(CC)Cc1sc(Nc2cc(Cl)nc(C)n2)nc1-c1cc(F)cc(C(F)(F)F)c1] | ESI+: 474, 476 |
TABLE 16
| PEx | PSyn | Str | DAT |
|---|---|---|---|
| 47 | 1 | 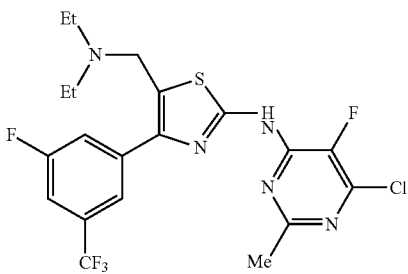 [SMILES: CCN(CC)Cc1sc(Nc2nc(C)nc(Cl)c2F)nc1-c1cc(F)cc(C(F)(F)F)c1] | ESI+: 492, 494 |
| 48 | 1 | 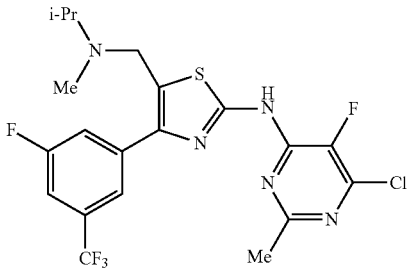 [SMILES: Cc1nc(Cl)c(F)c(Nc2nc(-c3cc(F)cc(C(F)(F)F)c3)c(CN(C)C(C)C)s2)n1] | ESI+: 492, 494 |
| 49 | 1 | 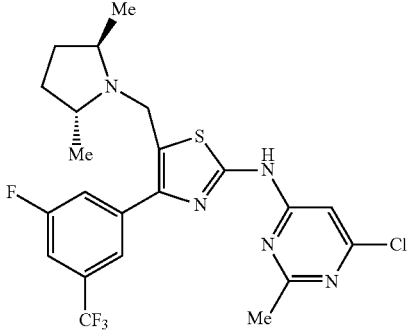 [SMILES: Cc1nc(Cl)cc(Nc2nc(-c3cc(F)cc(C(F)(F)F)c3)c(CN3[C@H](C)CC[C@H]3C)s2)n1] | ESI+: 500, 502 |

TABLE 16-continued
| PEx | PSyn | Str | DAT |
|-----|------|-----|-----|
| 50 | 1 | 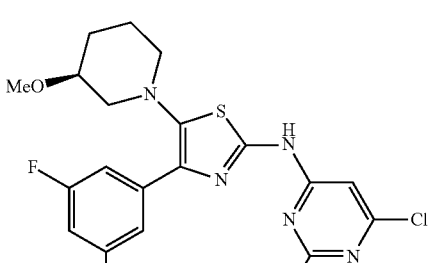 | APCI/ESI+: 502 |
TABLE 17
| PEx | PSyn | Str | DAT |
|-----|------|-----|-----|
| 51 | 1 | | APCI/ESI+: 515 |
| 52 | 1 | | APCI/ESI+: 504 |
| 53 | 1 | | ESI+: 502, 504 |

TABLE 18
| PEx | PSyn | Str | DAT |
|---|---|---|---|
| 54 | 1 | 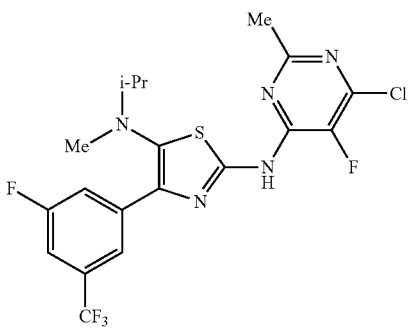 [SMILES: Cc1nc(Cl)c(F)c(Nc2nc(-c3cc(F)cc(C(F)(F)F)c3)c(N(C)C(C)C)s2)n1] | APCI/ESI+: 478 |
| 55 | 1 | 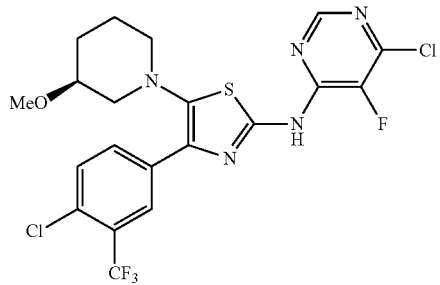 [SMILES: CO[C@H]1CCCN(c2sc(Nc3ncnc(Cl)c3F)nc2-c2ccc(Cl)c(C(F)(F)F)c2)C1] | ESI+: 522, 524 |
| 56 | 1 | 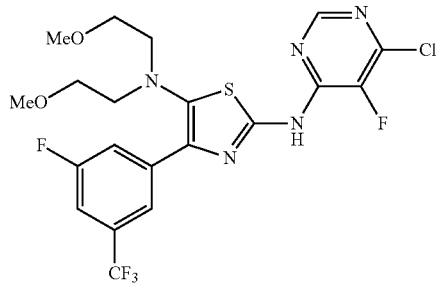 [SMILES: COCCN(CCOC)c1sc(Nc2ncnc(Cl)c2F)nc1-c1cc(F)cc(C(F)(F)F)c1] | APCI/ESI+: 524 |
| 57 | 1 | 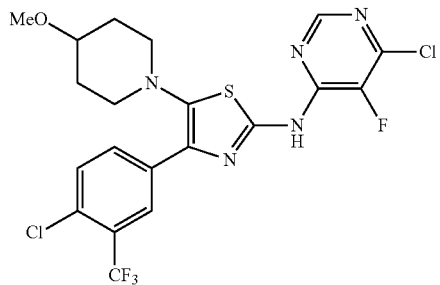 [SMILES: COC1CCN(c2sc(Nc3ncnc(Cl)c3F)nc2-c2ccc(Cl)c(C(F)(F)F)c2)CC1] | ESI+: 522, 524 |

TABLE 19
| PEx | PSyn | Str | DAT |
|---|---|---|---|
| 58 | 1 | 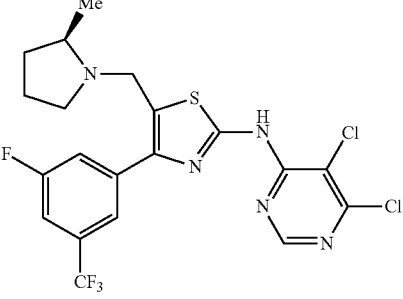 [SMILES: C[C@@H]1CCCN1Cc1sc(Nc2ncnc(Cl)c2Cl)nc1-c1cc(F)cc(C(F)(F)F)c1] | APCI/ESI+: 506, 508 |
| 59 | 1 | 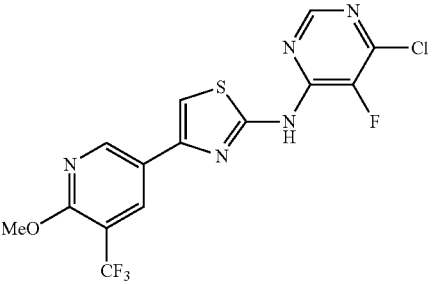 [SMILES: COc1ncc(-c2csc(Nc3ncnc(Cl)c3F)n2)cc1C(F)(F)F] | ESI+: 406, 408 |
| 60 | 1 | 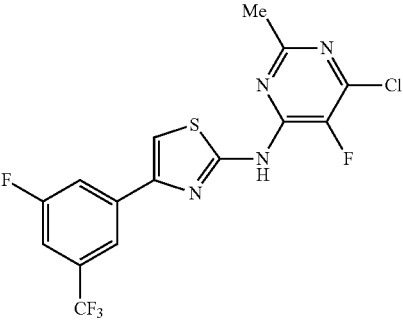 [SMILES: Cc1nc(Cl)c(F)c(Nc2nc(-c3cc(F)cc(C(F)(F)F)c3)cs2)n1] | ESI+: 407, 409 |
| 61 | 1 | 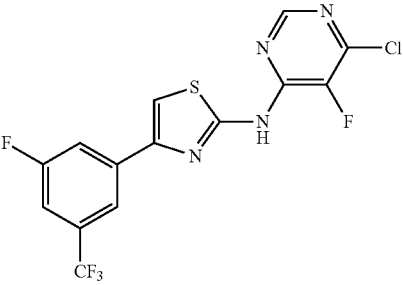 [SMILES: Fc1cc(-c2csc(Nc3ncnc(Cl)c3F)n2)cc(C(F)(F)F)c1] | APCI/ESI+: 393 |
TABLE 20
| PEx | PSyn | Str | DAT |
|---|---|---|---|
| 62 | 62 | 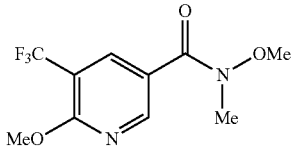 [SMILES: COc1ncc(C(=O)N(C)OC)cc1C(F)(F)F] | ESI+: 265 |

TABLE 20-continued
| PEx | PSyn | Str | DAT |
|---|---|---|---|
| 63 | 2 | | APCI/ESI+: 652 |
| 64 | 2 | | ESI+: 641 |
| 65 | 2 | | ESI+: 628 |
TABLE 21
| PEx | PSyn | Str | DAT |
|---|---|---|---|
| 66 | 2 | | ESI+: 672, 674 |
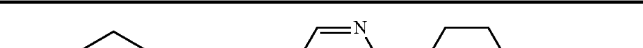

TABLE 21-continued
| PEx | PSyn | Str | DAT |
|---|---|---|---|
| 67 | 2 | 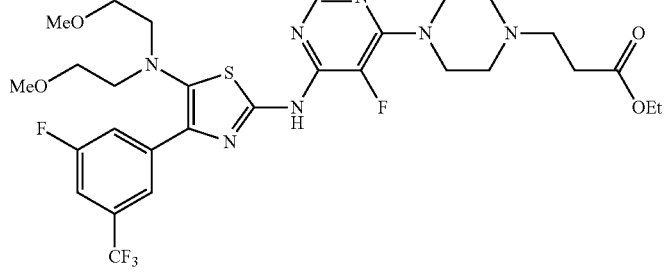 | APCI/ESI+: 674 |
| 68 | 2 | 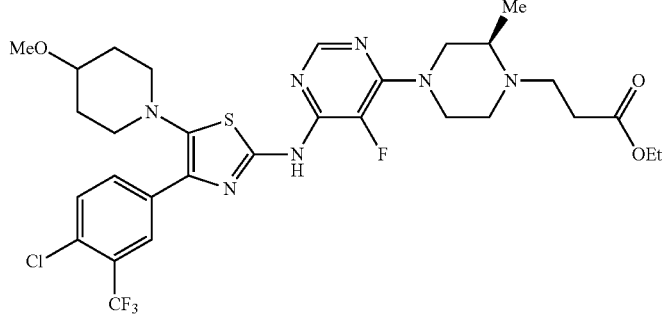 [SMILES: CCOC(=O)CCN1CCN(c2ncnc(Nc3nc(-c4ccc(Cl)c(C(F)(F)F)c4)c(N4CCC(OC)CC4)s3)c2F)C[C@H]1C] | ESI+: 686, 688 |
| 69 | 2 | 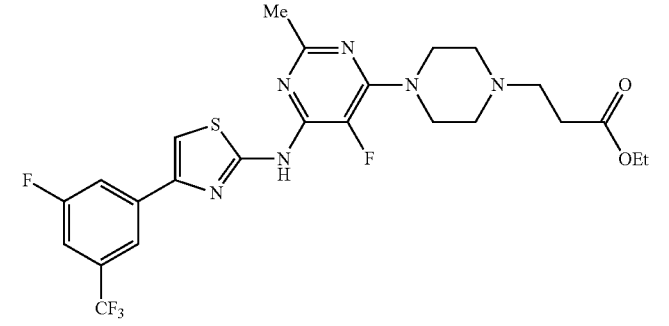 [SMILES: CCOC(=O)CCN1CCN(c2nc(C)nc(Nc3nc(-c4cc(F)cc(C(F)(F)F)c4)cs3)c2F)CC1] | APCI/ESI+: 557 |
TABLE 22
| PEx | PSyn | Str | DAT |
|---|---|---|---|
| 70 | 2 | 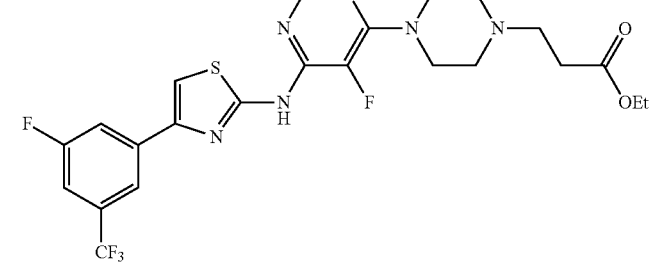 | APCI/ESI+: 543 |

TABLE 22-continued
| PEx | PSyn | Str | DAT |
|---|---|---|---|
| 71 | 2 | 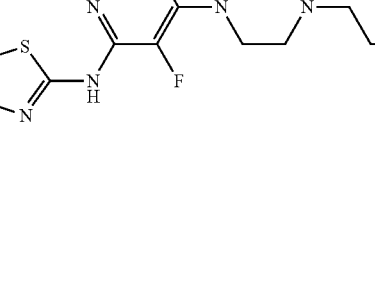 | ESI+: 556 |
| 72 | 3 | 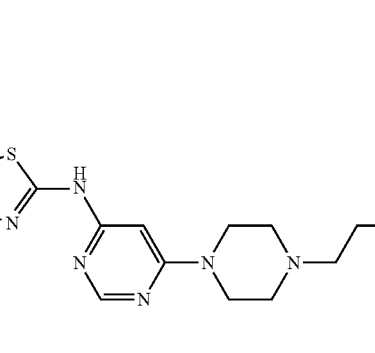 | ESI+: 622 |
| 73 | 3 | 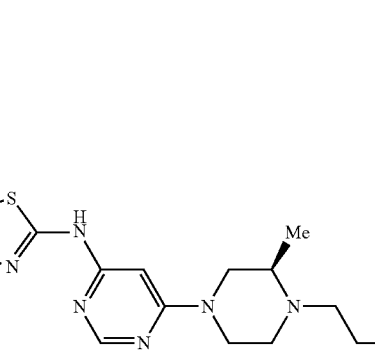 | ESI+: 636 |
TABLE 23
| PEx | PSyn | Str | DAT |
|---|---|---|---|
| 74 | 3 | | ESI+: 650 |

TABLE 23-continued
| PEx | PSyn | Str | DAT |
|---|---|---|---|
| 75 | 3 | 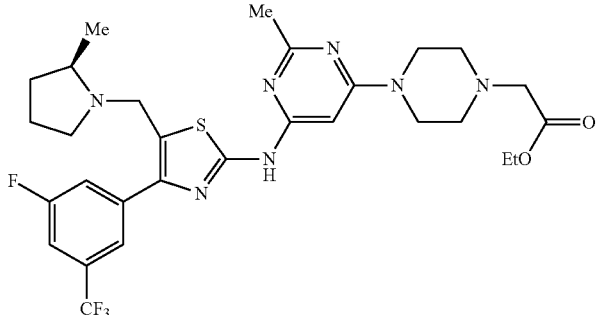 | ESI+: 622 |
| 76 | 3 | 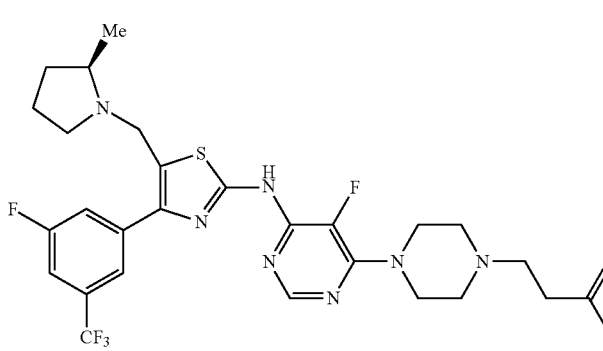 | APCI/ESI−: 638 |
TABLE 24
| PEx | PSyn | Str | DAT |
|---|---|---|---|
| 77 | 3 | 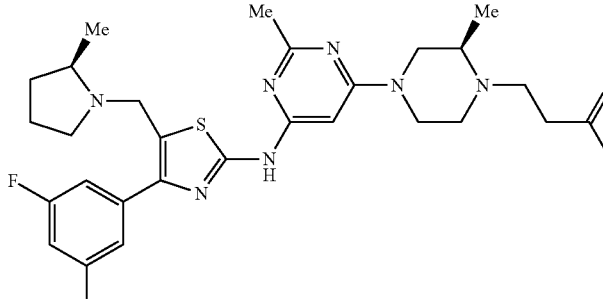 | ESI+: 650 |
| 78 | 3 | 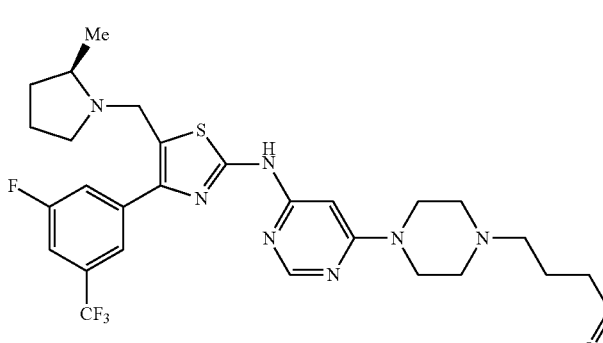 | ESI+: 636 |

TABLE 24-continued
| PEx | PSyn | Str | DAT |
|---|---|---|---|
| 79 | 5 | 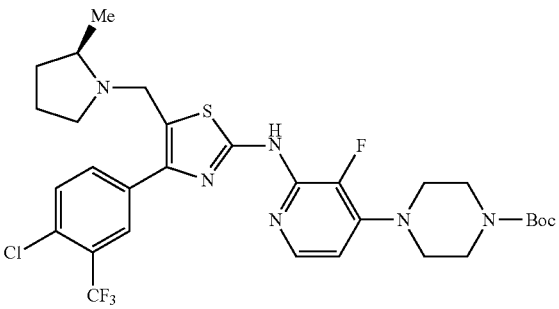 [SMILES: C[C@@H]1CCCN1Cc1sc(Nc2nccc(N3CCN(C(=O)OC(C)(C)C)CC3)c2F)nc1-c1ccc(Cl)c(C(F)(F)F)c1] | APCI/ESI+: 655 |
TABLE 25
| PEx | PSyn | Str | DAT |
|---|---|---|---|
| 80 | 3 | 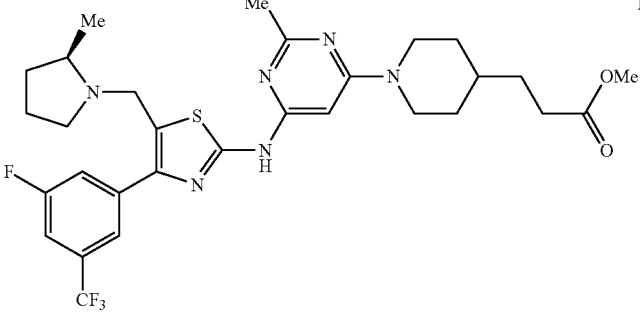 | ESI+: 621 |
| 81 | 3 | 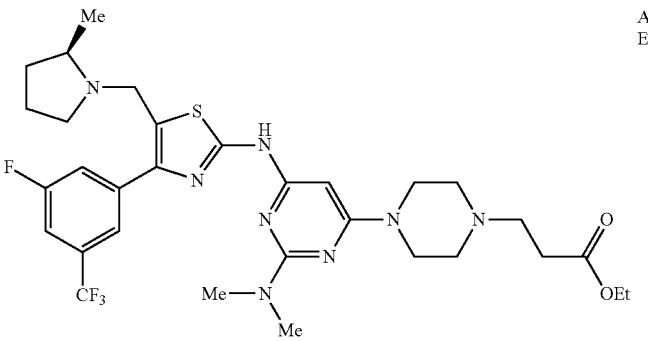 | APCI/ESI+: 665 |
| 82 | 3 | 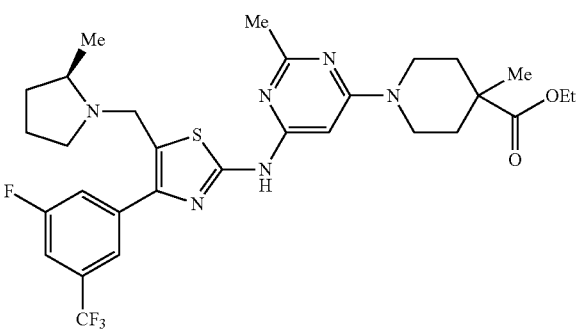 | ESI+: 621 |

TABLE 26
| PEx | PSyn | Str | DAT |
|---|---|---|---|
| 83 | 3 | 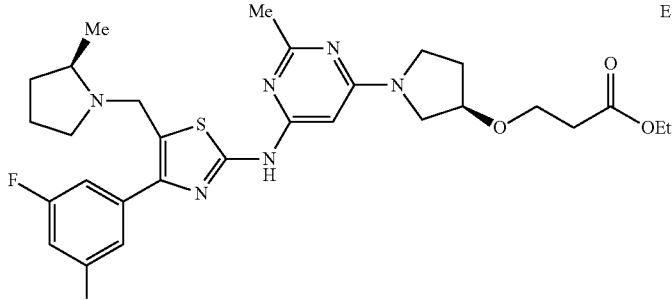 | ESI+: 637 |
| 84 | 3 | 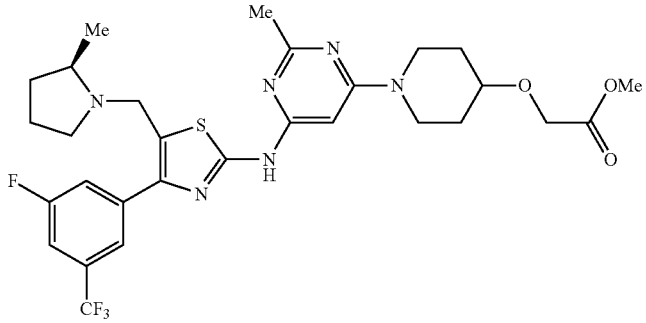 [SMILES: COC(=O)CCC1CCN(c2cc(Nc3nc(-c4cc(F)cc(C(F)(F)F)c4)c(CN4CCC[C@H]4C)s3)nc(C)n2)CC1] | ESI+: 623 |
| 85 | 3 | 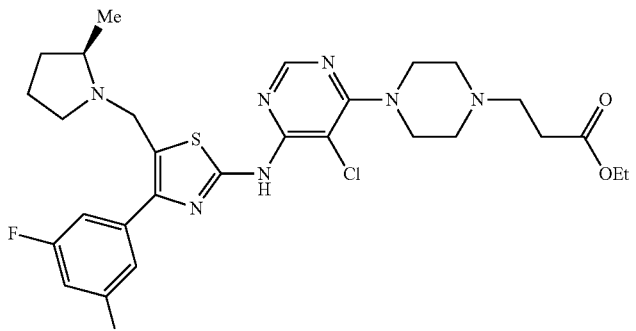 | APCI/ESI+: 656 |
TABLE 27
| PEx | PSyn | Str | DAT |
|---|---|---|---|
| 86 | 4 | 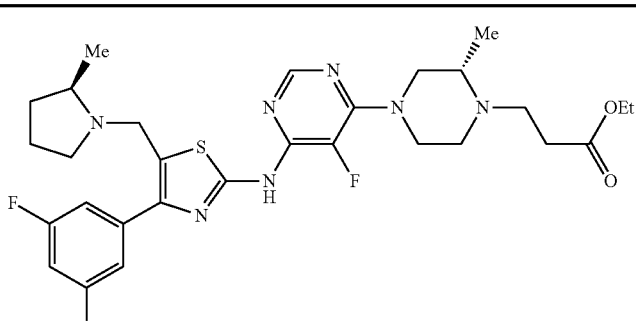 | ESI+: 654 |

TABLE 27-continued

| PEx | PSyn | Str | DAT |
|---|---|---|---|
| 87 | 4 | | ESI+: 654 |
| 88 | 4 | | ESI−: 654 |

TABLE 28

| PEx | PSyn | Str | DAT |
|---|---|---|---|
| 89 | 4 | | ESI+: 670, 672 |
| 90 | 4 | | ESI+: 670 |

TABLE 28-continued

| PEx | PSyn | Str | DAT |
|---|---|---|---|
| 91 | 4 | | ESI+: 627 |
| 92 | 4 | | APCI/ESI+: 628 |

TABLE 29

| PEx | PSyn | Str | DAT |
|---|---|---|---|
| 93 | 4 | | ESI+: 670 |
| 94 | 4 | | ESI+: 684 |

TABLE 29-continued
| PEx | PSyn | Str | DAT |
|---|---|---|---|
| 95 | 4 | 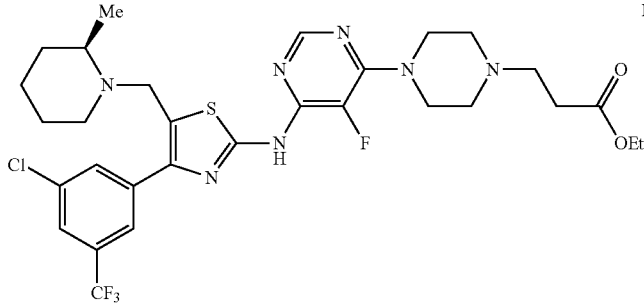 [SMILES: CCOC(=O)CCN1CCN(c2ncnc(Nc3nc(-c4cc(Cl)cc(C(F)(F)F)c4)c(CN4CCCC[C@H]4C)s3)c2F)CC1] | ESI+: 670 |
TABLE 30
| PEx | PSyn | Str | DAT |
|---|---|---|---|
| 96 | 4 | 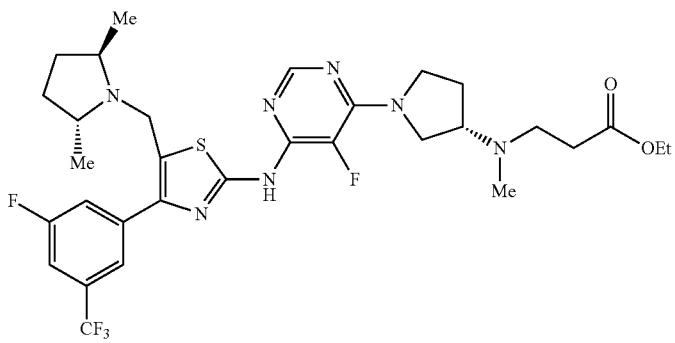 [SMILES: CCOC(=O)CCN(C)[C@H]1CCN(c2ncnc(Nc3nc(-c4cc(F)cc(C(F)(F)F)c4)c(CN4[C@H](C)CC[C@H]4C)s3)c2F)C1] | ESI+: 668 |
| 97 | 4 | 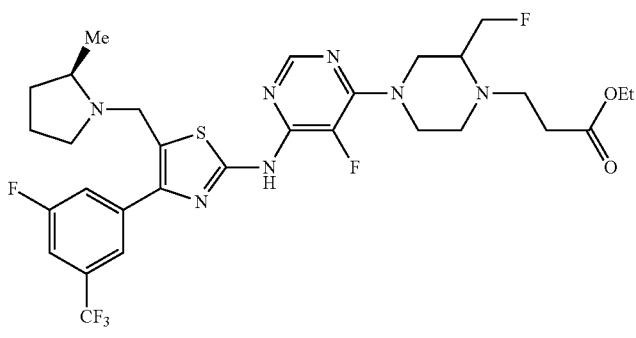 [SMILES: CCOC(=O)CCN1CCN(c2ncnc(Nc3nc(-c4cc(F)cc(C(F)(F)F)c4)c(CN4CCC[C@H]4C)s3)c2F)CC1CF] | ESI+: 672 |
| 98 | 4 | 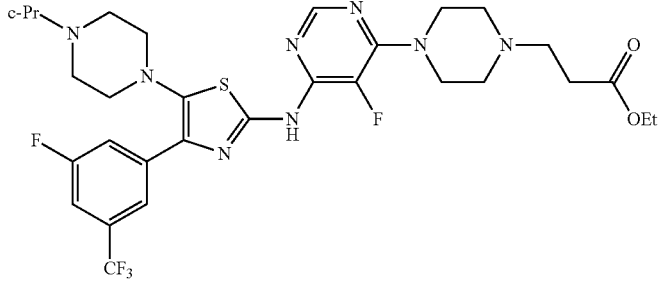 | APCI/ESI+: 667 |

TABLE 30-continued
| PEx | PSyn | Str | DAT |
|---|---|---|---|
| 99 | 4 | | ESI+: 656 |
TABLE 31
| PEx | PSyn | Str | DAT |
|---|---|---|---|
| 100 | 4 | | APCI/ESI+: 669 |
| 101 | 4 | | ESI−: 682 |
| 102 | 5 | | APCI/ESI−: 660 |
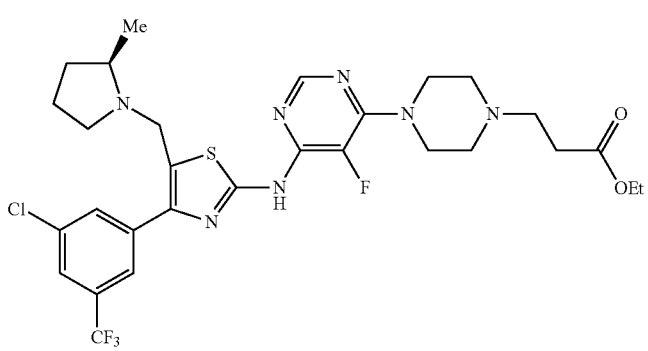 [SMILES: CCOC(=O)CCN1CCN(c2ncnc(Nc3nc(-c4cc(Cl)cc(C(F)(F)F)c4)c(CN4CCC[C@H]4C)s3)c2F)CC1]

TABLE 31-continued
| PEx | PSyn | Str | DAT |
|---|---|---|---|
| 103 | 5 | 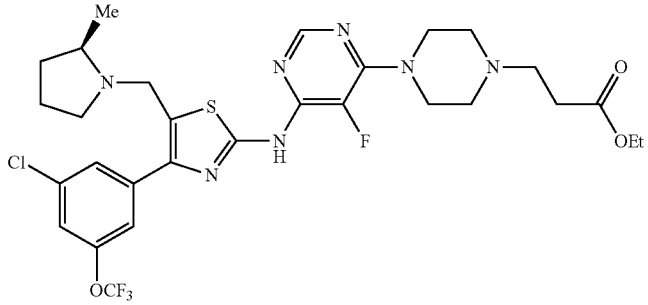 [SMILES: CCOC(=O)CCN1CCN(c2ncnc(Nc3nc(-c4cc(Cl)cc(OC(F)(F)F)c4)c(CN4CCC[C@H]4C)s3)c2F)CC1] | APCI/ESI+: 672 |
TABLE 32
| PEx | PSyn | Str | DAT |
|---|---|---|---|
| 104 | 104 | 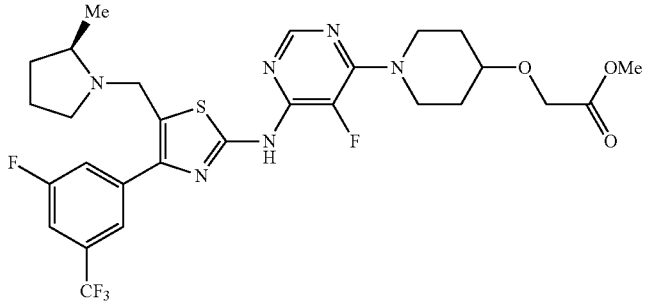 [SMILES: COC(=O)COC1CCN(c2ncnc(Nc3nc(-c4cc(F)cc(C(F)(F)F)c4)c(CN4CCC[C@H]4C)s3)c2F)CC1] | ESI+: 627 |
| 105 | 4 | 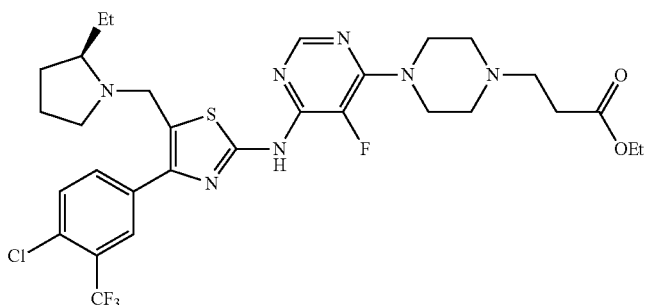 | ESI+: 670, 672 |
| 106 | 4 | 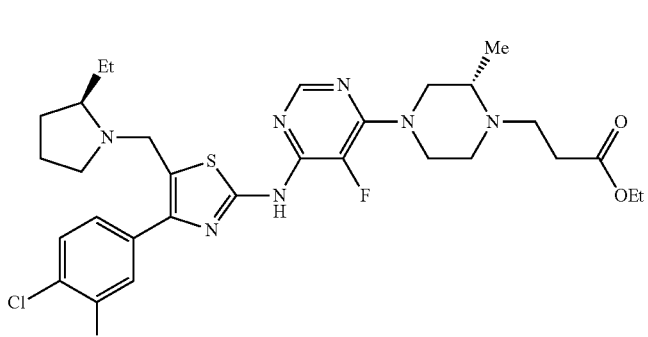 | ESI+: 684, 686 |

TABLE 33

| PEx | PSyn | Str | DAT |
|---|---|---|---|
| 107 | 4 | | ESI+: 684 |
| 108 | 4 | | ESI+: 641 |
| 109 | 4 | | ESI−: 668, 670 |

TABLE 34

| PEx | PSyn | Str | DAT |
|---|---|---|---|
| 110 | 4 | | ESI+: 700 |

TABLE 34-continued

| PEx | PSyn | Str | DAT |
|---|---|---|---|
| 111 | 4 | | APCI/ESI+: 668 |
| 112 | 4 | | APCI/ESI+: 668 |
| 113 | 4 | | ESI+: 672 |

TABLE 35

| PEx | PSyn | Str | DAT |
|---|---|---|---|
| 114 | 4 | | ESI+: 688, 690 |

TABLE 35-continued

| PEx | PSyn | Str | DAT |
|-----|------|-----|-----|
| 115 | 4 | | ESI+: 670, 672 |
| 116 | 4 | | ESI+: 684, 686 |
| 117 | 4 | | ESI+: 672 |

TABLE 36

| PEx | PSyn | Str | DAT |
|-----|------|-----|-----|
| 118 | 4 | | ESI+: 684, 686 |

TABLE 36-continued

| PEx | PSyn | Str | DAT |
|---|---|---|---|
| 119 | 4 | | ESI−: 682, 684 |
| 120 | 4 | | ESI+: 670, 672 |
| 121 | 4 | | ESI+: 657, 659 |

TABLE 37

| PEx | PSyn | Str | DAT |
|---|---|---|---|
| 122 | 4 | | ESI+: 671, 673 |

TABLE 37-continued
| PEx | PSyn | Str | DAT |
|---|---|---|---|
| 123 | 4 | 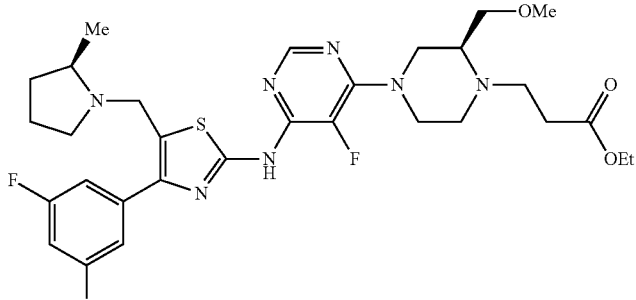 | ESI+: 698 |
| 124 | 4 | 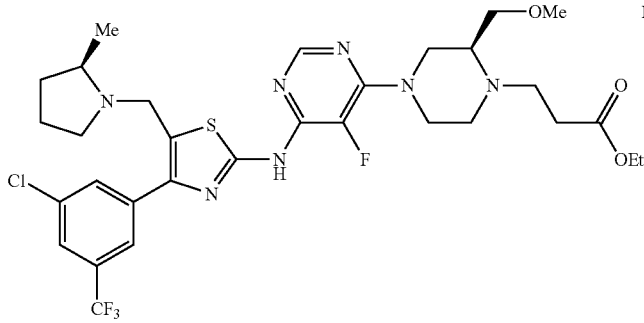 [SMILES: CCOC(=O)CCN1CCN(c2ncnc(Nc3nc(-c4cc(Cl)cc(C(F)(F)F)c4)c(CN4CCC[C@H]4C)s3)c2F)C[C@H]1COC] | ESI+: 714, 716 |
| 125 | 4 | 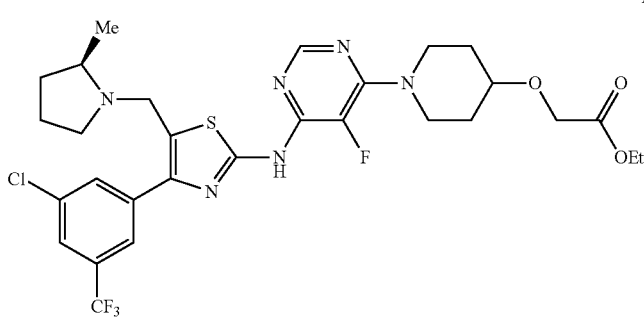 | ESI+: 671, 673 |
TABLE 38
| PEx | PSyn | Str | DAT |
|---|---|---|---|
| 126 | 4 | 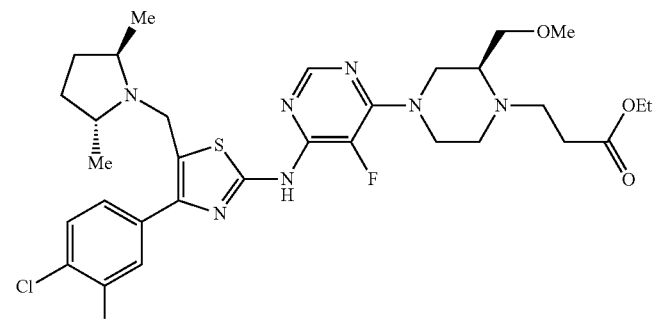 | ESI−: 712, 714 |

TABLE 38-continued
| PEx | PSyn | Str | DAT |
|---|---|---|---|
| 127 | 4 | 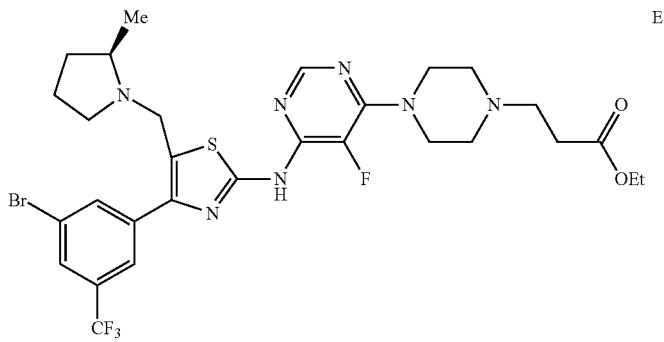 | ESI-: 698 |
| 128 | 4 | 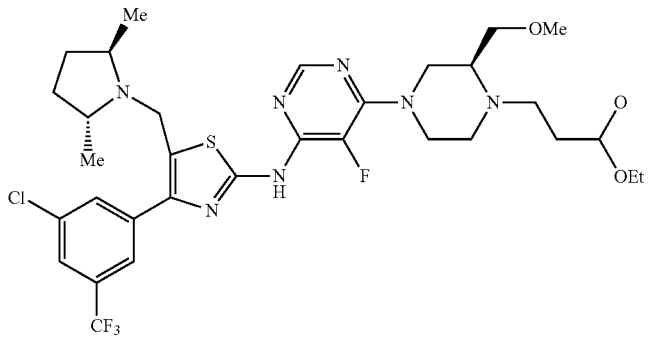 [SMILES: CCOC(O)CCN1CCN(c2ncnc(Nc3nc(-c4cc(Cl)cc(C(F)(F)F)c4)c(CN4[C@H](C)CC[C@H]4C)s3)c2F)C[C@H]1COC] | ESI+: 714 |
TABLE 39
| PEx | PSyn | Str | DAT |
|---|---|---|---|
| 129 | 4 | 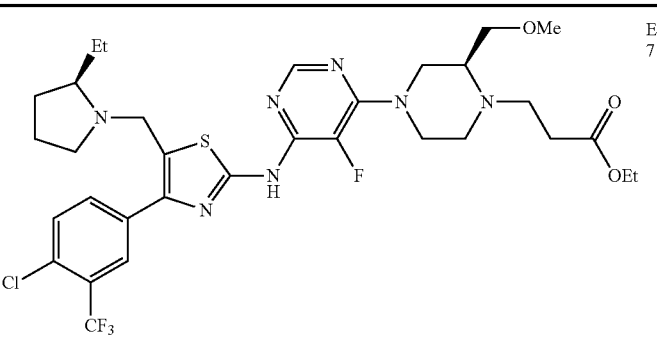 | ESI+: 714, 716 |
| 130 | 5 | 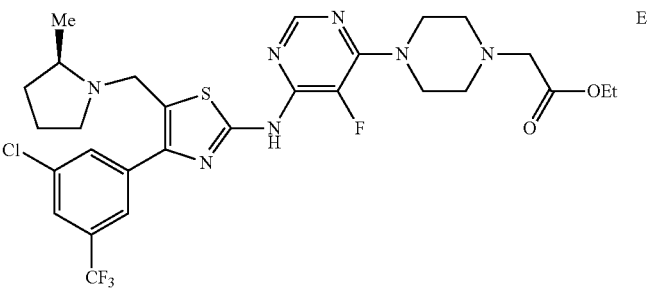 | ESI+: 642 |

TABLE 39-continued
| PEx | PSyn | Str | DAT |
|---|---|---|---|
| 131 | 4 | 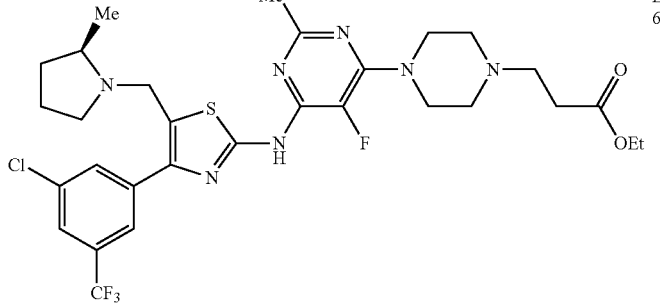 | ESI+: 670, 672 |
| 132 | 4 | 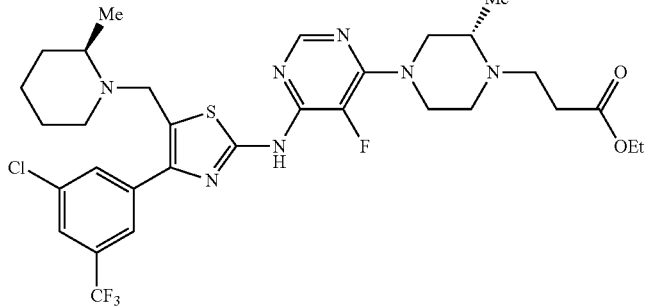 | ESI+: 684, 686 |
TABLE 40
| PEx | PSyn | Str | DAT |
|---|---|---|---|
| 133 | 4 | 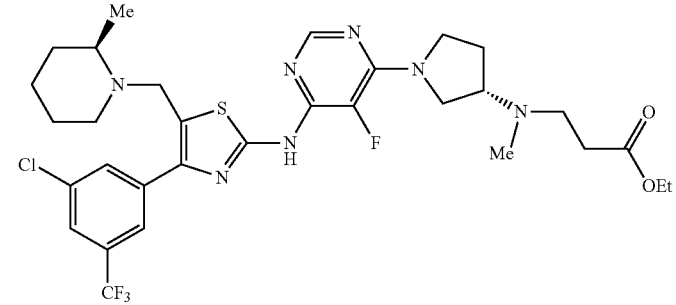 [SMILES: CCOC(=O)CCN(C)[C@H]1CCN(c2ncnc(Nc3nc(-c4cc(Cl)cc(C(F)(F)F)c4)c(CN4CCCC[C@H]4C)s3)c2F)C1] | ESI−: 682, 684 |
| 134 | 4 | 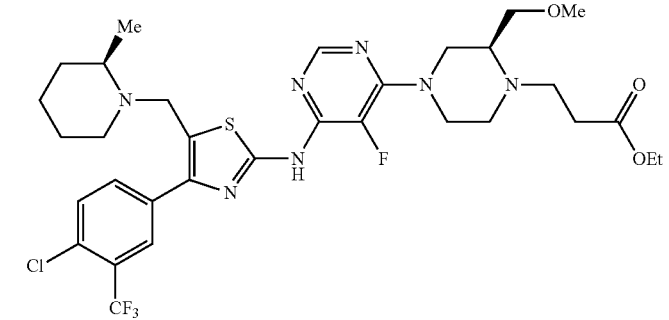 [SMILES: CCOC(=O)CCN1CCN(c2ncnc(Nc3nc(-c4ccc(Cl)c(C(F)(F)F)c4)c(CN4CCCC[C@H]4C)s3)c2F)C[C@H]1COC] | APCI/ESI+: 714 |

TABLE 40-continued

| PEx | PSyn | Str | DAT |
|---|---|---|---|
| 135 | 135 | | ESI+: 662 |
| 136 | 4 | | ESI+: 670 |

TABLE 41

| PEx | PSyn | Str | DAT |
|---|---|---|---|
| 137 | 4 | | ESI+: 686 |
| 138 | 5 | | ESI−: 638 |

TABLE 41-continued

| PEx | PSyn | Str | DAT |
|---|---|---|---|
| 139 | 5 | | APCI/ESI+: 681 |
| 140 | 5 | | ESI+: 624 |

TABLE 42

| PEx | PSyn | Str | DAT |
|---|---|---|---|
| 141 | 5 | | APCI/ESI+: 653 |
| 142 | 5 | | APCI/ESI+: 653 |

TABLE 42-continued
| PEx | PSyn | Str | DAT |
|---|---|---|---|
| 143 | 6 | 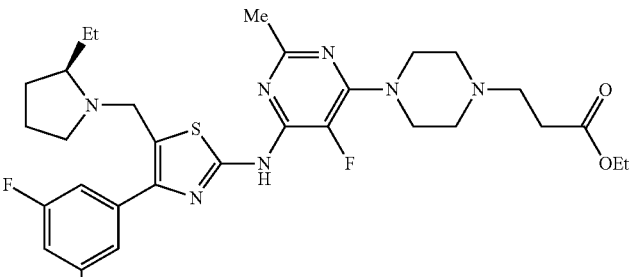 | APCI/ESI+: 668 |
TABLE 43
| PEx | PSyn | Str | DAT |
|---|---|---|---|
| 144 | 6 | | APCI/ESI+: 668 |
| 145 | 6 | | APCI/ESI+: 668 |
| 146 | 6 | | ESI+: 667 |

TABLE 44
| PEx | PSyn | Str | DAT |
|---|---|---|---|
| 147 | 6 | 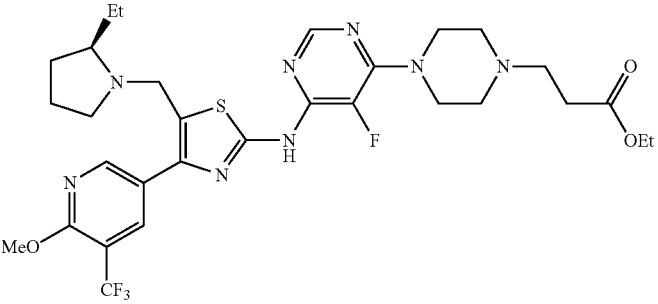 [SMILES: CCOC(=O)CCN1CCN(c2ncnc(Nc3nc(-c4cnc(OC)c(C(F)(F)F)c4)c(CN4CCC[C@H]4CC)s3)c2F)CC1] | ESI+: 667 |
| 148 | 8 | 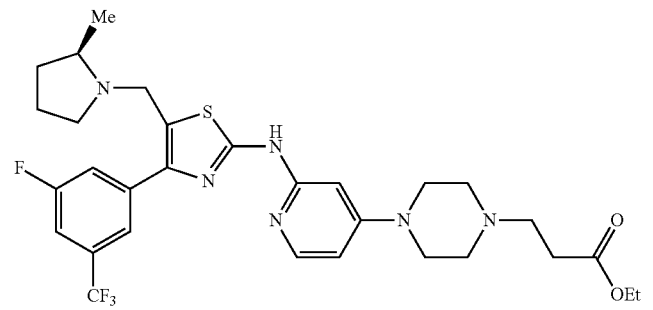 [SMILES: CCOC(=O)CCN1CCN(c2ccnc(Nc3nc(-c4cc(F)cc(C(F)(F)F)c4)c(CN4CCC[C@H]4C)s3)c2)CC1] | ESI+: 621 |
| 149 | 8 | 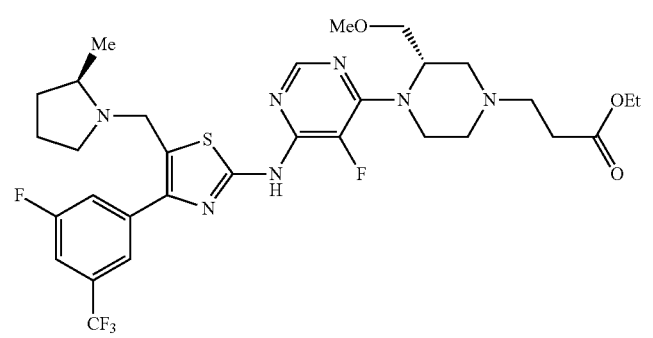 [SMILES: CCOC(=O)CCN1CCN(c2ncnc(Nc3nc(-c4cc(F)cc(C(F)(F)F)c4)c(CN4CCC[C@H]4C)s3)c2F)[C@H](COC)C1] | ESI+: 685 |
TABLE 45
| PEx | PSyn | Str | DAT |
|---|---|---|---|
| 150 | 8 | 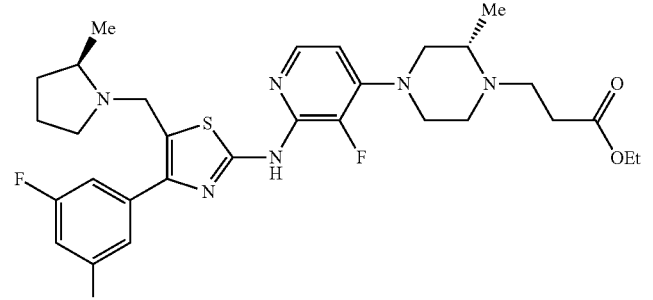 | APCI/ESI+: 653 |

TABLE 45-continued
| PEx | PSyn | Str | DAT |
|---|---|---|---|
| 151 | 8 | 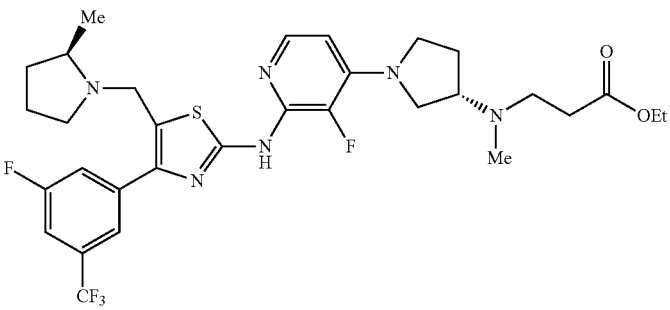 [SMILES: CCOC(=O)CCN(C)[C@H]1CCN(c2ccnc(Nc3nc(-c4cc(F)cc(C(F)(F)F)c4)c(CN4CCC[C@H]4C)s3)c2F)C1] | APCI/ESI+: 653 |
| 152 | 152 | 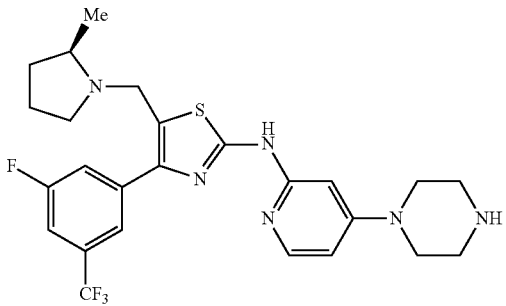 [SMILES: C[C@@H]1CCCN1Cc1sc(Nc2cc(N3CCNCC3)ccn2)nc1-c1cc(F)cc(C(F)(F)F)c1] | ESI+: 521 |
TABLE 46
| PEx | PSyn | Str | DAT |
|---|---|---|---|
| 153 | 9 | 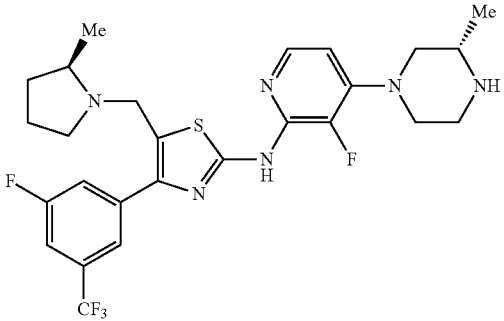 [SMILES: C[C@@H]1CCCN1Cc1sc(Nc2nccc(N3CCN[C@@H](C)C3)c2F)nc1-c1cc(F)cc(C(F)(F)F)c1] | APCI/ESI+: 553 |
| 154 | 9 | 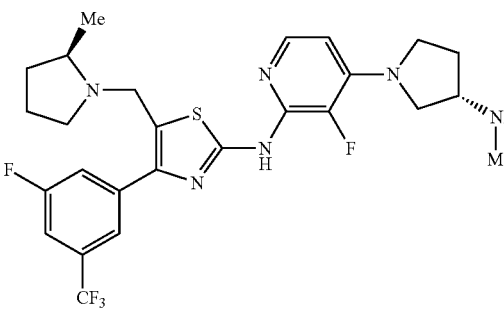 | APCI/ESI+: 553 |

TABLE 46-continued

| PEx | PSyn | Str | DAT |
|---|---|---|---|
| 155 | 11 | (structure) | ESI+: 390, 392 |
| 156 | 11 | (structure) | APCI/ESI+: 390 |

TABLE 47

| PEx | PSyn | Str | DAT |
|---|---|---|---|
| 157 | 11 | (structure) | APCI/ESI+: 382 |
| 158 | 11 | (structure) | ESI+: 348 |
| 159 | 11 | (structure) | ESI+: 360 |
| 160 | 11 | (structure) | ESI+: 348 |

TABLE 48

| PEx | PSyn | Str | DAT |
|---|---|---|---|
| 161 | 11 | (structure) | ESI+: 390, 392 |

TABLE 48-continued

| PEx | PSyn | Str | DAT |
|---|---|---|---|
| 162 | 11 | (structure) | ESI+: 390, 392 |
| 163 | 11 | (structure) | ESI+: 390, 392 |
| 164 | 11 | (structure) | APCI/ESI+: 392, 394 |

TABLE 49

| PEx | PSyn | Str | DAT |
|---|---|---|---|
| 165 | 11 | (structure) | ESI+: 390, 392 |
| 166 | 12 | (structure) | ESI+: 372 |
| 167 | 12 | (structure) | ESI+: 376, 378 |
| 168 | 12 | (structure) | ESI+: 374 |

TABLE 50

| PEx | PSyn | Str | DAT |
|---|---|---|---|
| 169 | 12 | (structure) | ESI+: 356 |

TABLE 50-continued
| PEx | PSyn | Str | DAT |
|---|---|---|---|
| 170 | 12 | 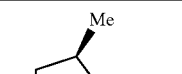 | NMR-DMSO-d6: 1.11 (3H, d, J = 6 Hz), 1.30-1.41 (1H, m), 1.59-1.69 (2H, m), 1.87-1.98 (1H, m), 2.05-2.15 (1H, m), 2.35-2.45 (1H, m), 2.94-3.02 (1H, m), 3.18 (1H, d, J = 14 Hz), 3.97 (3H, d, J = 2 Hz), 3.98 (1H, d, J = 14 Hz), 6.98 (2H, brs), 7.85-7.89 (1H, m), 8.02 (1H, dd, J = 13, 2 Hz) |
TABLE 51
| PEx | PSyn | Str | DAT |
|---|---|---|---|
| 171 | 12 | | ESI+: 420, 422 |
| 172 | 15 | | ESI+: 432 |
| 173 | 15 | | ESI+: 414 |
| 174 | 15 | | ESI+: 416 |
TABLE 52
| PEx | PSyn | Str | DAT |
|---|---|---|---|
| 175 | 15 | | ESI+: 424 |
| 176 | 15 | | ESI+: 398 |

TABLE 52-continued
| PEx | PSyn | Str | DAT |
|---|---|---|---|
| 177 | 15 | 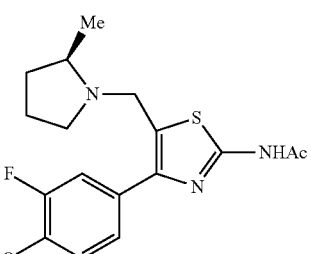 | APCI/ESI+: 432 |
TABLE 53
| PEx | PSyn | Str | DAT |
|---|---|---|---|
| 178 | 15 | | ESI+: 462, 464 |
| 179 | 15 | | ESI+: 432, 434 |
| 180 | 15 | | ESI+: 390 |
TABLE 53-continued
| PEx | PSyn | Str | DAT |
|---|---|---|---|
| 181 | 15 | 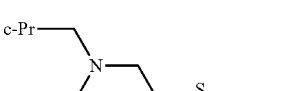 | ESI+: 402 |
TABLE 54
| PEx | PSyn | Str | DAT |
|---|---|---|---|
| 182 | 15 | | ESI+: 390 |
| 183 | 15 | | ESI+: 432, 434 |
| 184 | 15 | | ESI+: 432, 434 |

TABLE 54-continued

| PEx | PSyn | Str | DAT |
|---|---|---|---|
| 185 | 15 | (2-Me-piperidinylmethyl)-4-(3-Cl-5-CF3-phenyl)-thiazol-2-yl-NHAc | ESI+: 432, 434 |

TABLE 55

| PEx | PSyn | Str | DAT |
|---|---|---|---|
| 186 | 15 | (2-Me-pyrrolidinylmethyl)-4-(3-Cl-5-OCF3-phenyl)-thiazol-2-yl-NHAc | APCI/ESI+: 434 |
| 187 | 15 | (2-Et-pyrrolidinylmethyl)-4-(3-CF3-4-Cl-phenyl)-thiazol-2-yl-NHAc | ESI+: 432, 434 |
| 188 | 16 | (2-Me-pyrrolidinylmethyl)-4-(3-Cl-5-CF3-phenyl)-thiazol-2-yl-NHAc | ESI+: 418, 420 |
| 189 | 189 | AcOCH2-4-(3-Cl-4-CF3-phenyl)-thiazol-2-yl-NHAc | ESI+: 393, 395 |

TABLE 56

| PEx | PSyn | Str | DAT |
|---|---|---|---|
| 190 | 17 | AcOCH2-4-(3-MeO-5-CF3-phenyl)-thiazol-2-yl-NHAc | ESI+: 389 |
| 191 | 17 | AcOCH2-4-(3-Cl-5-CF3-phenyl)-thiazol-2-yl-NHAc | ESI+: 393, 395 |
| 192 | 17 | AcOCH2-4-(3-Me-5-CF3-phenyl)-thiazol-2-yl-NHAc | ESI+: 373 |
| 193 | 17 | AcOCH2-4-(4-c-Pr-3-CF3-phenyl)-thiazol-2-yl-NHAc | ESI+: 399 |
| 194 | 17 | AcOCH2-4-(3-F-4-MeO-5-CF3-phenyl)-thiazol-2-yl-NHAc | APCI/ESI+: 407 |

TABLE 57

| PEx | PSyn | Str | DAT |
|---|---|---|---|
| 195 | 17 | AcOCH2-4-(3-Br-5-CF3-phenyl)-thiazol-2-yl-NHAc | ESI+: 437, 439 |

TABLE 57-continued

| PEx | PSyn | Str | DAT |
|---|---|---|---|
| 196 | 196 | 4-(4-chloro-3-(trifluoromethyl)phenyl)-N-acetylthiazol-2-amine | ESI+: 321, 323 |
| 197 | 19 | 4-(3-methoxy-5-(trifluoromethyl)phenyl)-N-acetylthiazol-2-amine | ESI+: 317 |
| 198 | 19 | 4-(3-chloro-5-(trifluoromethyl)phenyl)-N-acetylthiazol-2-amine | ESI+: 321 |
| 199 | 19 | 4-(3-methyl-5-(trifluoromethyl)phenyl)-N-acetylthiazol-2-amine | ESI+: 301 |

TABLE 58

| PEx | PSyn | Str | DAT |
|---|---|---|---|
| 200 | 19 | 4-(4-cyclopropyl-3-(trifluoromethyl)phenyl)-N-acetylthiazol-2-amine | ESI+: 327 |
| 201 | 19 | 4-(3-fluoro-4-methoxy-5-(trifluoromethyl)phenyl)-N-acetylthiazol-2-amine | ESI+: 335 |

TABLE 58-continued

| PEx | PSyn | Str | DAT |
|---|---|---|---|
| 202 | 19 | 4-(3-bromo-5-(trifluoromethyl)phenyl)-N-acetylthiazol-2-amine | ESI+: 365, 367 |
| 203 | 19 | 4-(3-chloro-5-(trifluoromethoxy)phenyl)-N-acetylthiazol-2-amine | APCI/ESI+: 337 |
| 204 | 20 | 5-((3R)-3-methoxypiperidin-1-yl)-4-(3-fluoro-5-(trifluoromethyl)phenyl)thiazol-2-amine | APCI/ESI+: 376 |

TABLE 59

| PEx | PSyn | Str | DAT |
|---|---|---|---|
| 205 | 20 | 5-((3R)-3-methoxypiperidin-1-yl)-4-(4-chloro-3-(trifluoromethyl)phenyl)thiazol-2-amine | ESI+: 392, 394 |
| 206 | 20 | 5-(4-methoxypiperidin-1-yl)-4-(4-chloro-3-(trifluoromethyl)phenyl)thiazol-2-amine | ESI+: 392, 394 |

TABLE 59-continued
| PEx | PSyn | Str | DAT |
|---|---|---|---|
| 207 | 20 | 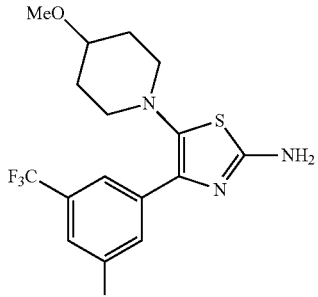 | APCI/ESI+: 376 |
| 208 | 20 | 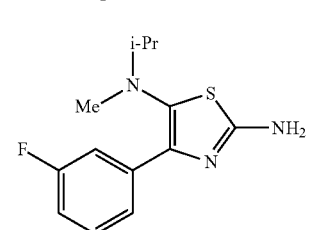 | APCI/ESI+: 334 |
TABLE 60
| PEx | PSyn | Str | DAT |
|---|---|---|---|
| 209 | 20 | 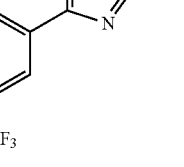 | APCI/ESI+: 394 |
| 210 | 20 | | APCI/ESI+: 348 |
| 211 | 20 | | ESI+: 387 |
TABLE 60-continued
| PEx | PSyn | Str | DAT |
|---|---|---|---|
| 212 | 20 | 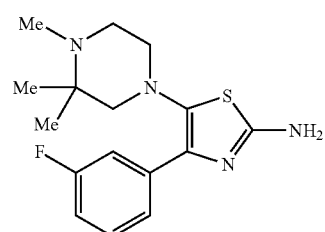 | APCI/ESI+: 389 |
TABLE 61
| PEx | PSyn | Str | DAT |
|---|---|---|---|
| 213 | 213 | | ESI+: 279, 281 |
| 214 | 21 | | ESI+: 279, 281 |
| 215 | 21 | | ESI+: 295, 297 |
| 216 | 21 | | ESI+: 275 |
| 217 | 21 | | ESI+: 285 |

TABLE 61-continued

| PEx | PSyn | Str | DAT |
|---|---|---|---|
| 218 | 21 | 4-(3-fluoro-4-methoxy-5-(trifluoromethyl)phenyl)thiazol-2-amine | ESI+: 293 |

TABLE 62

| PEx | PSyn | Str | DAT |
|---|---|---|---|
| 219 | 21 | 4-(3-methyl-5-(trifluoromethyl)phenyl)thiazol-2-amine | ESI+: 259 |
| 220 | 21 | 4-(3-bromo-5-(trifluoromethyl)phenyl)thiazol-2-amine | ESI+: 323, 325 |
| 221 | 21 | 4-(6-methoxy-5-(trifluoromethyl)pyridin-3-yl)thiazol-2-amine | ESI+: 276 |
| 222 | 22 | ethyl 3-(4-(6-chloro-5-fluoropyrimidin-4-yl)piperazin-1-yl)propanoate | ESI+: 317, 319 |
| 223 | 22 | ethyl 3-(4-(6-chloro-5-fluoro-2-methylpyrimidin-4-yl)piperazin-1-yl)propanoate | ESI+: 331, 333 |

TABLE 63

| PEx | PSyn | Str | DAT |
|---|---|---|---|
| 224 | 22 | | ESI+: 347, 349 |
| 225 | 22 | | ESI+: 304, 306 |
| 226 | 22 | | ESI+: 331, 333 |
| 227 | 22 | | ESI+: 331, 333 |
| 228 | 228 | | ESI+: 304, 306 |
| 229 | 22 | | ESI+: 349, 351 |
| 230 | 22 | | ESI+: 361 |

TABLE 64

| PEx | PSyn | Str | DAT |
|---|---|---|---|
| 231 | 22 | | ESI+: 361, 363 |
| 232 | 22 | | ESI+: 349, 351 |

TABLE 64-continued
| PEx | PSyn | Str | DAT |
|---|---|---|---|
| 233 | 22 | 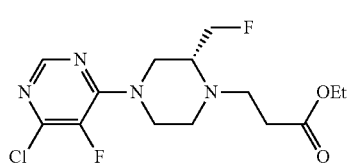 [SMILES: CCOC(=O)CCN1CCN(c2ncnc(Cl)c2F)C[C@@H]1CF] | ESI+: 349, 351 |
| 234 | 22 | 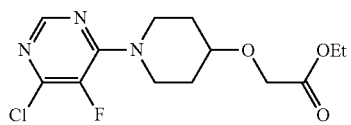 | ESI+: 318, 320 |
| 235 | 22 | 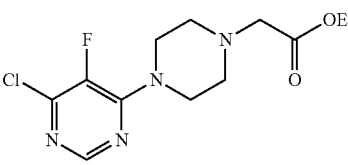 | APCI/ESI+: 303 |
| 236 | 22 | 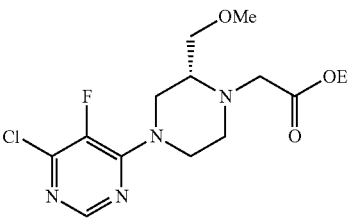 | ESI+: 347, 349 |
TABLE 65
| PEx | PSyn | Str | DAT |
|---|---|---|---|
| 237 | 22 | 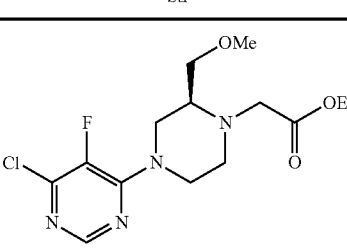 | ESI+: 347, 349 |
| 238 | 23 | 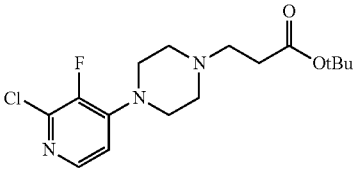 [SMILES: CC(C)(C)OC(=O)CCN1CCN(c2ccnc(Cl)c2F)CC1] | ESI+: 344, 346 |
| 239 | 23 | 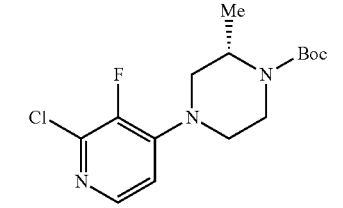 [SMILES: C[C@H]1CN(c2ccnc(Cl)c2F)CCN1C(=O)OC(C)(C)C] | ESI+: 330, 332 |
TABLE 65-continued
| PEx | PSyn | Str | DAT |
|---|---|---|---|
| 240 | 23 | 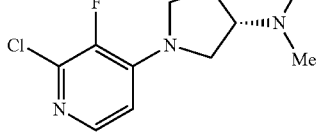 | ESI+: 330, 332 |
| 241 | 23 | 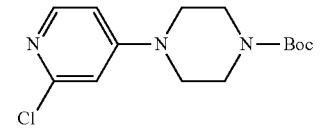 [SMILES: CC(C)(C)OC(=O)N1CCN(c2ccnc(Cl)c2)CC1] | ESI+: 298, 300 |
| 242 | 24 | 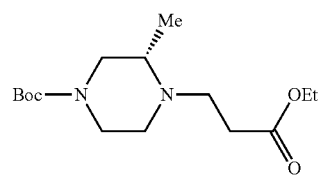 [SMILES: CCOC(=O)CCN1CCN(C(=O)OC(C)(C)C)C[C@@H]1C] | ESI+: 301 |
TABLE 66
| PEx | PSyn | Str | DAT |
|---|---|---|---|
| 243 | 24 | 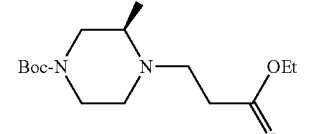 | ESI+: 301 |
| 244 | 24 | 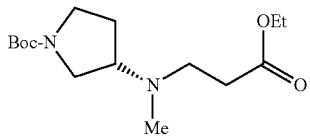 | ESI+: 301 |
| 245 | 24 | 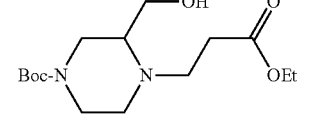 | ESI+: 317 |
| 246 | 24 | 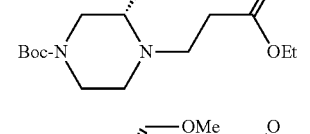 | ESI+: 317 |
| 247 | 25 | 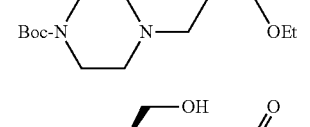 | ESI+: 331 |
| 248 | 25 | 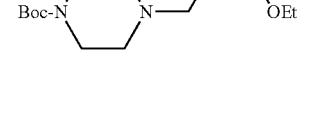 | ESI+: 317 |

TABLE 66-continued

| PEx | PSyn | Str | DAT |
|---|---|---|---|
| 249 | 28 | Boc-N-piperazine-CH2F, N-CH2CH2C(O)OEt | ESI+: 319 |
| 250 | 28 | Boc-N-piperazine-CH2F (other enantiomer), N-CH2CH2C(O)OEt | ESI+: 319 |

TABLE 67

| PEx | PSyn | Str | DAT |
|---|---|---|---|
| 251 | 29 | Boc-N-piperazine-CH2OMe, N-CH2C(O)OEt | ESI+: 317 |
| 252 | 30 | HN-piperazine-Me, N-CH2CH2C(O)OEt · 2HCl | ESI+: 201 |
| 253 | 31 | HN-pyrrolidine-N(Me)CH2CH2C(O)OEt · 2HCl | CI+: 201 |
| 254 | 31 | HN-pyrrolidine-O-CH2CH2C(O)OEt · HCl | ESI+: 188 |
| 255 | 31 | HN-piperazine-CH2F, N-CH2CH2C(O)OEt · 2HCl | ESI+: 219 |
| 256 | 31 | HN-piperazine-CH2OMe, N-CH2CH2C(O)OEt · 2HCl | ESI+: 231 |
| 257 | 31 | HN-piperazine-CH2F, N-CH2CH2C(O)OEt · 2HCl | ESI+: 219 |

TABLE 68

| PEx | PSyn | Str | DAT |
|---|---|---|---|
| 258 | 31 | HN-piperazine-CH2F, N-CH2CH2C(O)OEt · 2HCl | ESI+: 219 |
| 259 | 31 | HN-piperazine-CH2OMe, N-CH2C(O)OEt · 2HCl | ESI+: 217 |
| 260 | 31 | HN-piperazine-CH2OMe, N-CH2C(O)OEt · 2HCl | ESI+: 217 |
| 261 | 31 | HN-piperazine-CH2OH, N-CH2CH2C(O)OEt · 2HCl | ESI+: 217 |
| 262 | 34 | 3-Me-5-CF3-phenyl-Ac | EI+: 202[M+] |

TABLE 69

| Ex | Str |
|---|---|
| 1 | Me-pyrrolidine-CH2-thiazole[4-(4-Cl-3-CF3-phenyl)]-2-NH-pyrimidine(5-F)-4-piperazine(CH2OMe)-N-CH2CH2COOH · 3HCl |
| 2 | Me-pyrrolidine-CH2-thiazole[4-(4-Cl-3-CF3-phenyl)]-2-NH-pyridine(3-F)-4-piperazine-N-CH2CH2COO− Na+ |

TABLE 69-continued
| Ex | Str |
|---|---|
| 3 | 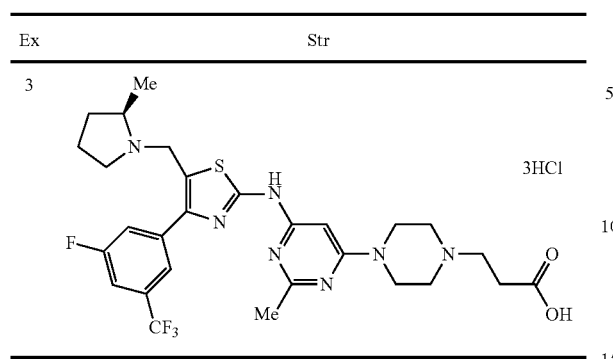 3HCl |
TABLE 70
| Ex | Str |
|---|---|
| 4 | 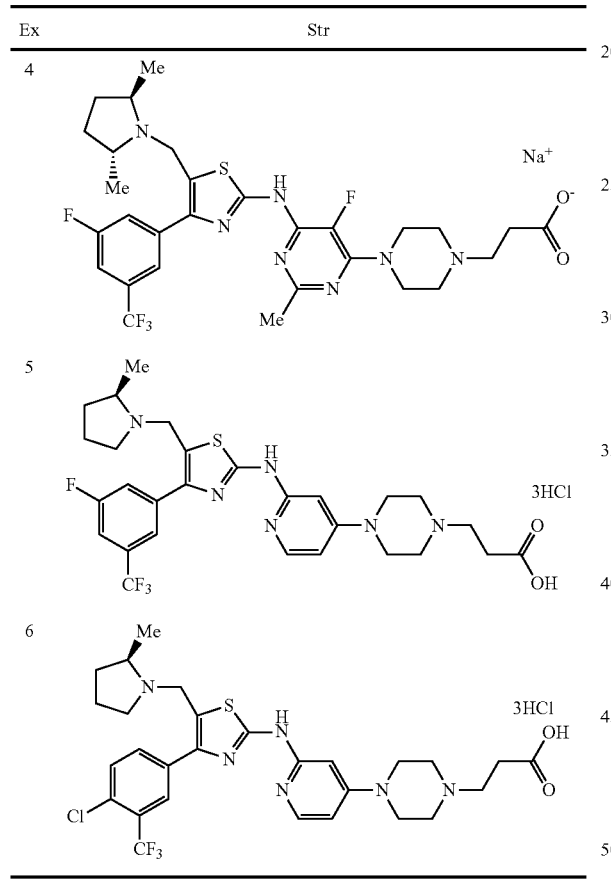 Na+ |
| 5 | 3HCl |
| 6 | 3HCl |
TABLE 71
| Ex | Str |
|---|---|
| 7 | 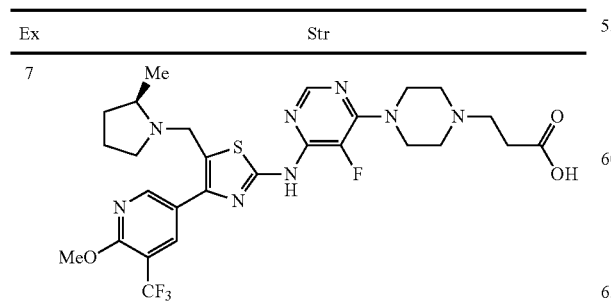 |
TABLE 71-continued
| Ex | Str |
|---|---|
| 8 | 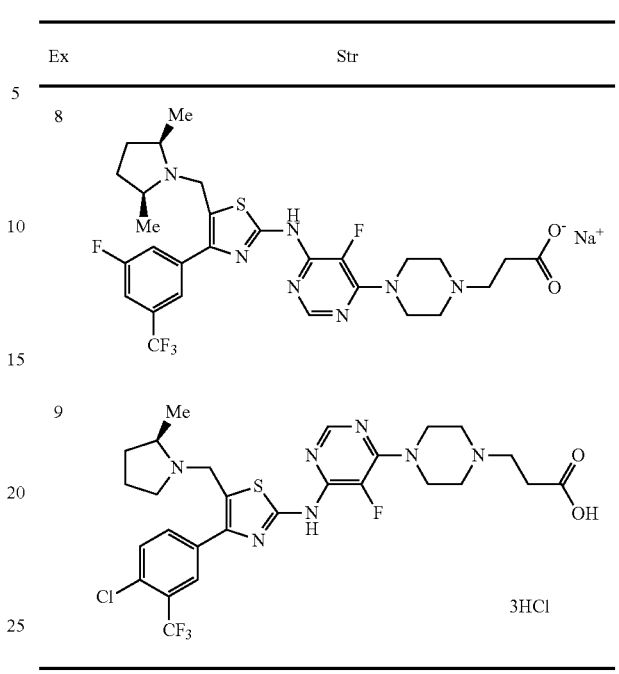 Na+ |
| 9 | 3HCl |
TABLE 72
| Ex | Str |
|---|---|
| 10 | 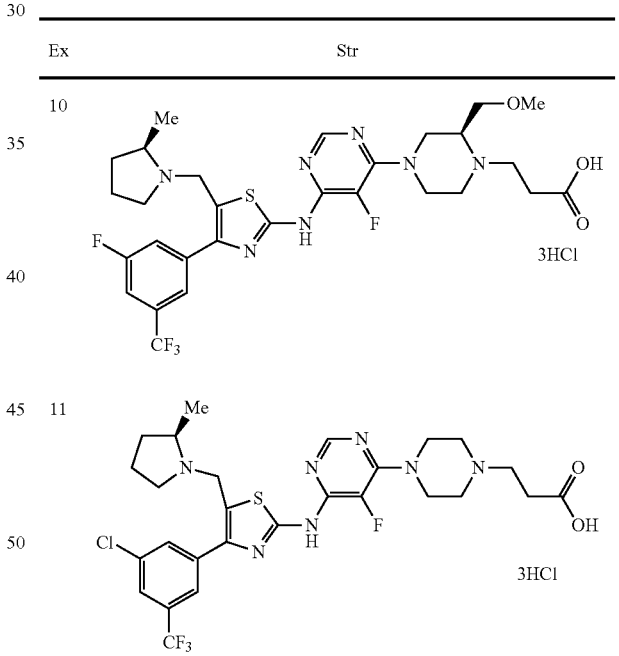 3HCl |
| 11 | 3HCl |
| 12 | 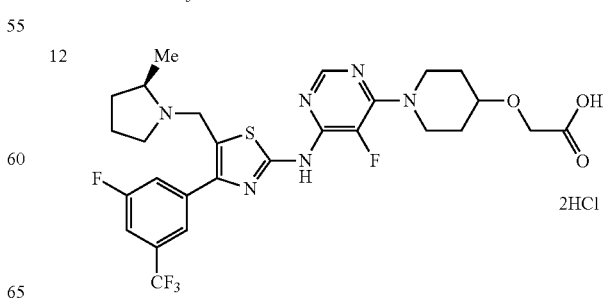 2HCl |

TABLE 73
| Ex | Str |
|---|---|
| 13 | 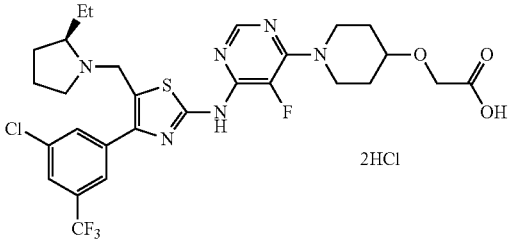 [SMILES: CC[C@@H]1CCCN1Cc1sc(Nc2ncnc(N3CCC(OCC(=O)O)CC3)c2F)nc1-c1cc(Cl)cc(C(F)(F)F)c1] 2HCl |
| 14 | 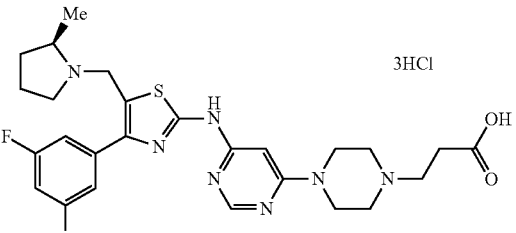 3HCl |
| 15 | 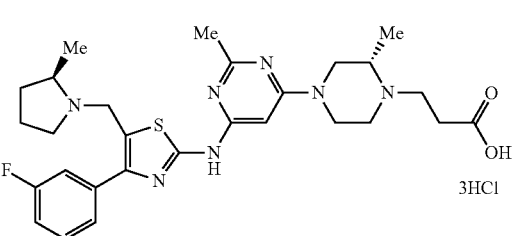 3HCl |
| 16 | 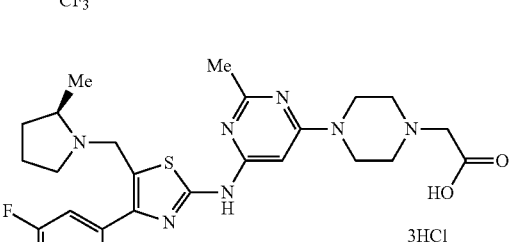 3HCl |
TABLE 74
| Ex | Str |
|---|---|
| 17 | 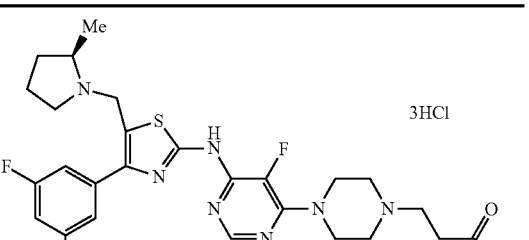 3HCl |
| 18 | 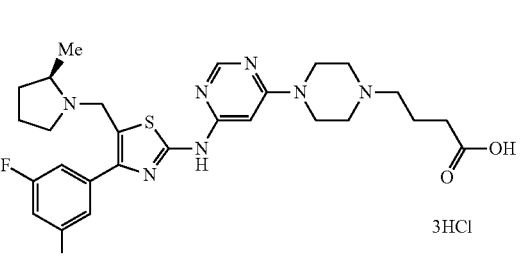 3HCl |
| 19 | 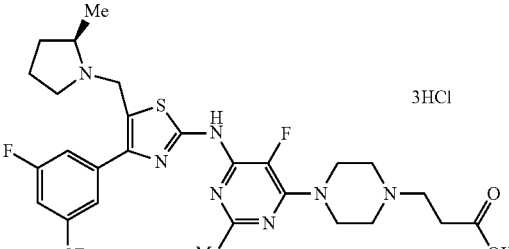 3HCl |
TABLE 75
| Ex | Str |
|---|---|
| 20 | 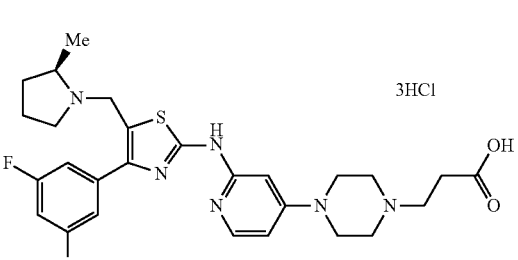 3HCl |
| 21 |  3HCl |
| 22 |  3HCl |

TABLE 75-continued
| Ex | Str |
|---|---|
| 23 | 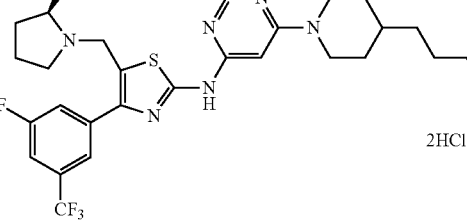 3HCl |
TABLE 76
| Ex | Str |
|---|---|
| 24 | 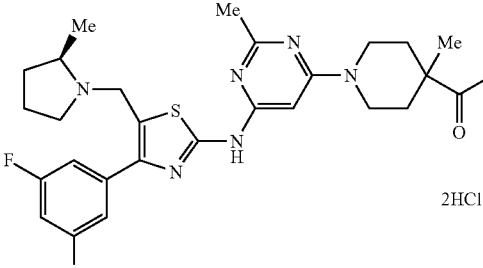 2HCl |
| 25 | 2HCl |
| 26 | 2HCl |
TABLE 77
| Ex | Str |
|---|---|
| 27 | 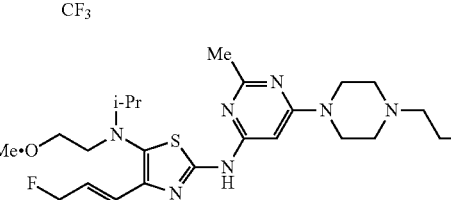 2HCl |
| 28 | 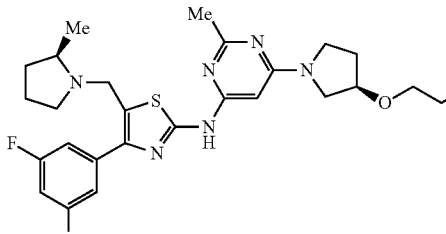 2HCl |
| 29 | 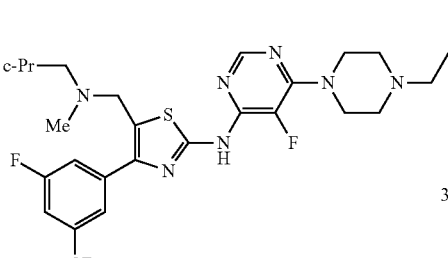 3HCl |
TABLE 78
| Ex | Str |
|---|---|
| 30 | 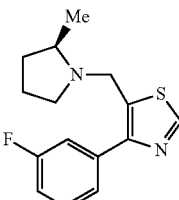 2HCl |
| 31 | 3HCl |
| 32 | 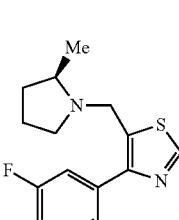 2HCl |

149
TABLE 78-continued
| Ex | Str |
|---|---|
| 33 | 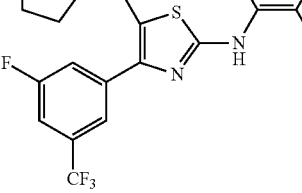 2HCl |
TABLE 79
| Ex | Str |
|---|---|
| 34 | 3HCl |
| 35 | 3HCl |
| 36 | 3HCl |
| 37 | 2HCl |
150
TABLE 80
| Ex | Str |
|---|---|
| 38 | 3HCl |
| 39 | 2HCl |
| 40 | 3HCl |
| 41 | 3HCl |
TABLE 81
| Ex | Str |
|---|---|
| 42 | 3HCl |

TABLE 81-continued
| Ex | Str |
|---|---|
| 43 | 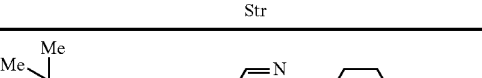 3HCl |
| 44 | 3HCl |
| 45 | 3HCl |
TABLE 82
| Ex | Str |
|---|---|
| 46 | 3HCl |
TABLE 82-continued
| Ex | Str |
|---|---|
| 47 | 3HCl |
| 48 | 3HCl |
| 49 | 3HCl |
TABLE 83
| Ex | Str |
|---|---|
| 50 |  3HCl |

TABLE 83-continued
| Ex | Str |
|---|---|
| 51 | 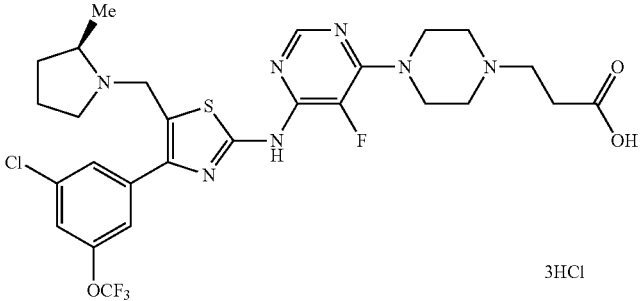 [SMILES: C[C@@H]1CCCN1Cc1sc(Nc2ncnc(N3CCN(CCC(=O)O)CC3)c2F)nc1-c1cc(Cl)cc(OC(F)(F)F)c1] 3HCl |
| 52 | 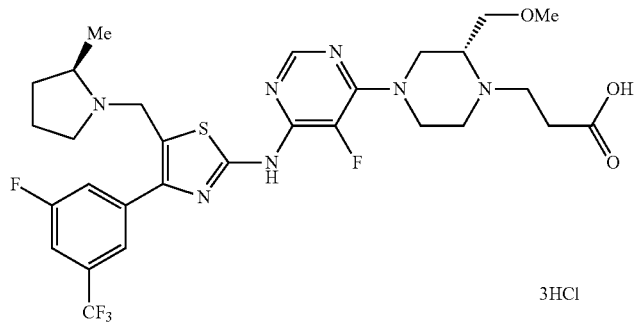 [SMILES: COC[C@H]1CN(c2ncnc(Nc3nc(-c4cc(F)cc(C(F)(F)F)c4)c(CN4CCC[C@H]4C)s3)c2F)CCN1CCC(=O)O] 3HCl |
| 53 | 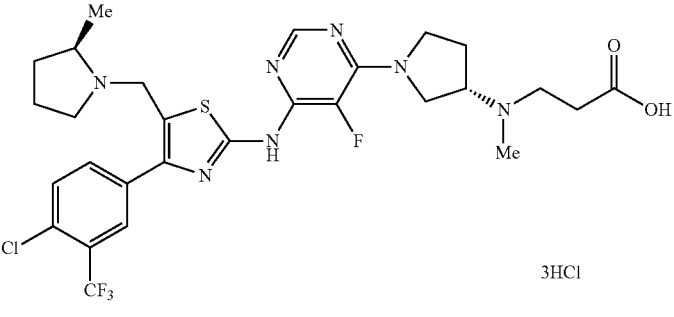 [SMILES: C[C@@H]1CCCN1Cc1sc(Nc2ncnc(N3CC[C@H](N(C)CCC(=O)O)C3)c2F)nc1-c1ccc(Cl)c(C(F)(F)F)c1] 3HCl |
TABLE 84
| Ex | Str |
|---|---|
| 54 | 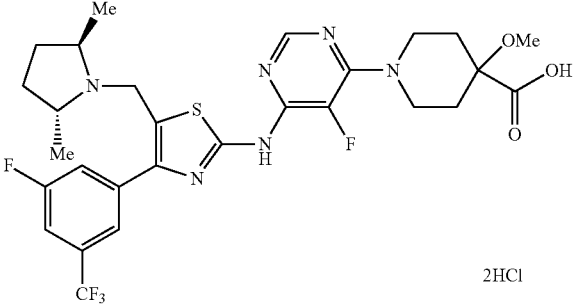 [SMILES: COC1(C(=O)O)CCN(c2ncnc(Nc3nc(-c4cc(F)cc(C(F)(F)F)c4)c(CN4[C@H](C)CC[C@H]4C)s3)c2F)CC1] 2HCl |

TABLE 84-continued
| Ex | Str |
|---|---|
| 55 | 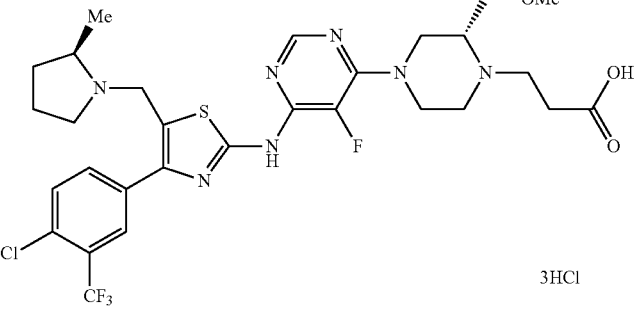 3HCl |
| 56 | 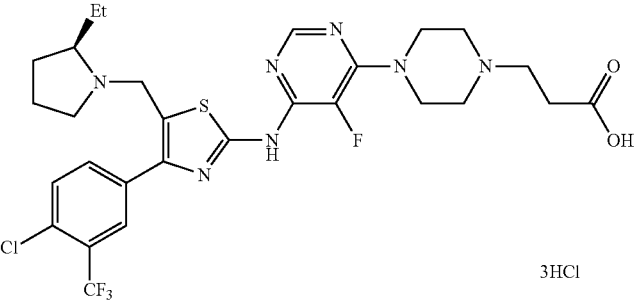 [SMILES: CC[C@@H]1CCCN1Cc1sc(Nc2ncnc(N3CCN(CCC(=O)O)CC3)c2F)nc1-c1ccc(Cl)c(C(F)(F)F)c1] 3HCl |
| 57 | 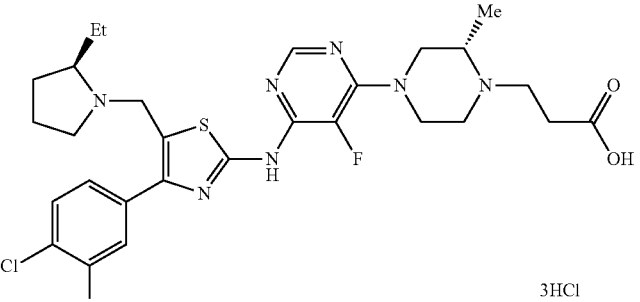 3HCl |
TABLE 85
| Ex | Str |
|---|---|
| 58 | 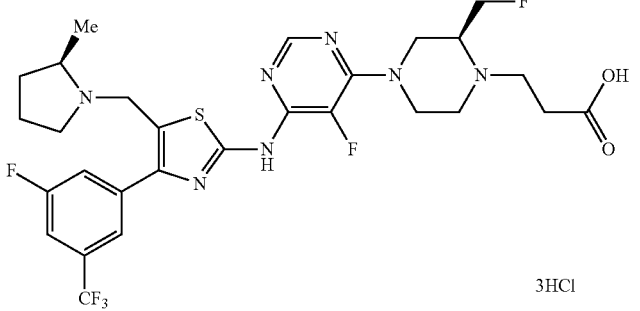 3HCl |

TABLE 85-continued
| Ex | Str |
|---|---|
| 59 | 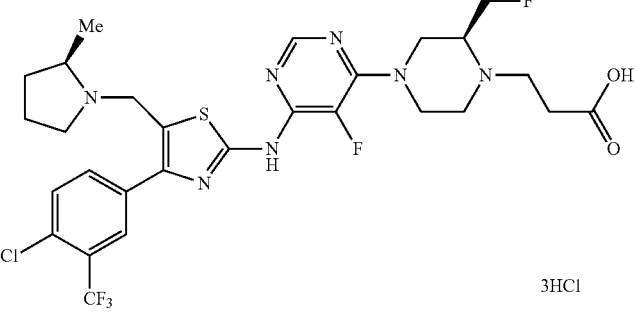 3HCl |
| 60 | 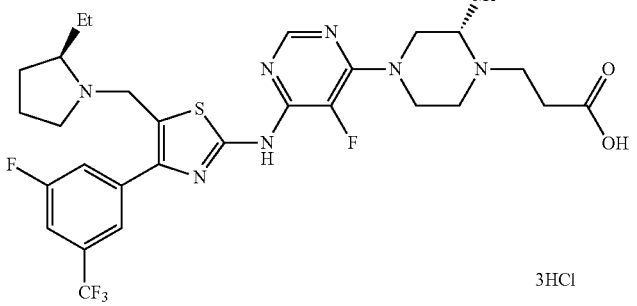 3HCl |
| 61 | 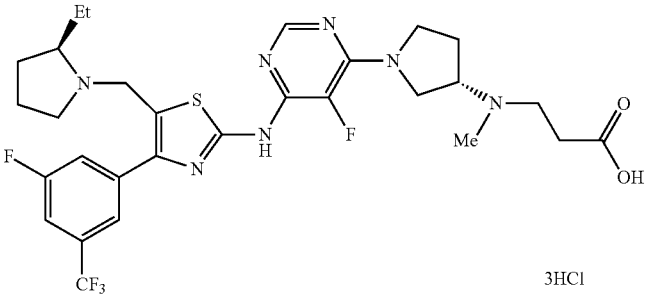 [SMILES: CC[C@@H]1CCCN1Cc1sc(Nc2ncnc(N3CC[C@H](N(C)CCC(=O)O)C3)c2F)nc1-c1cc(F)cc(C(F)(F)F)c1] 3HCl |
TABLE 86
| Ex | Str |
|---|---|
| 62 | 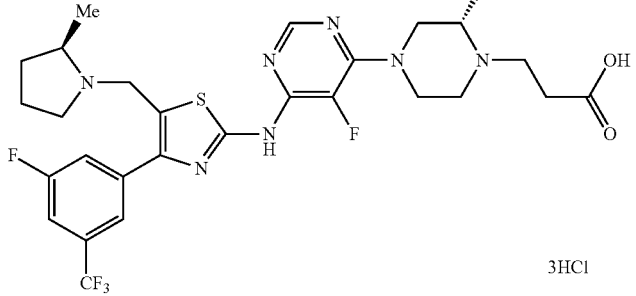 3HCl |

TABLE 86-continued
| Ex | Str |
|---|---|
| 63 | 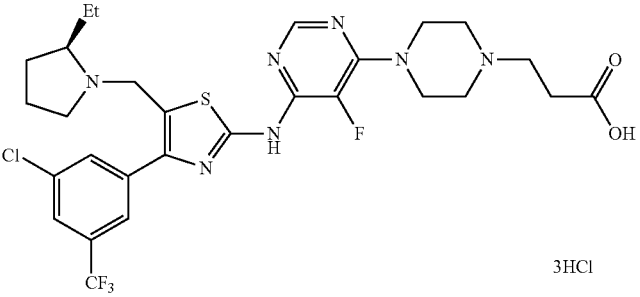 [SMILES: CC[C@@H]1CCCN1Cc1sc(Nc2ncnc(N3CCN(CCC(=O)O)CC3)c2F)nc1-c1cc(Cl)cc(C(F)(F)F)c1] 3HCl |
| 64 | 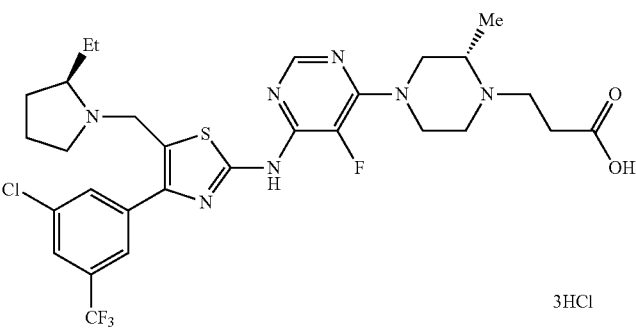 [SMILES: CC[C@@H]1CCCN1Cc1sc(Nc2ncnc(N3CCN(CCC(=O)O)[C@@H](C)C3)c2F)nc1-c1cc(Cl)cc(C(F)(F)F)c1] 3HCl |
| 65 | 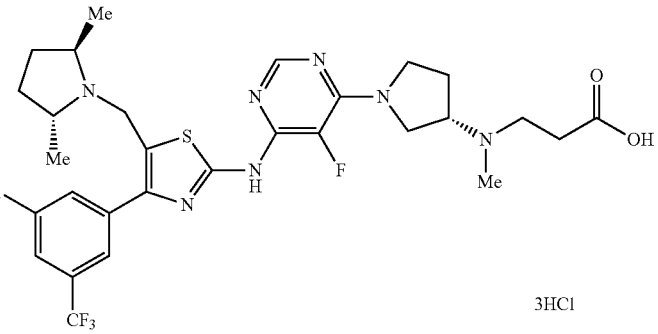 3HCl |
TABLE 87
| Ex | Str |
|---|---|
| 66 | 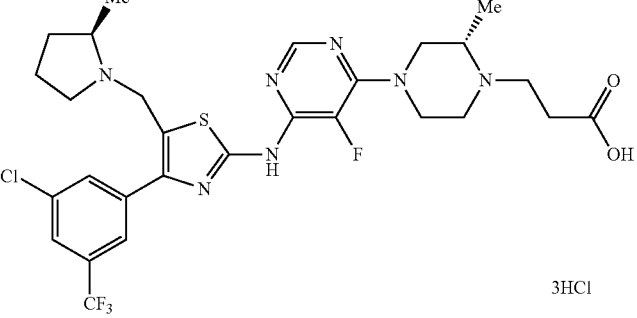 3HCl |

TABLE 87-continued
| Ex | Str |
|---|---|
| 67 | 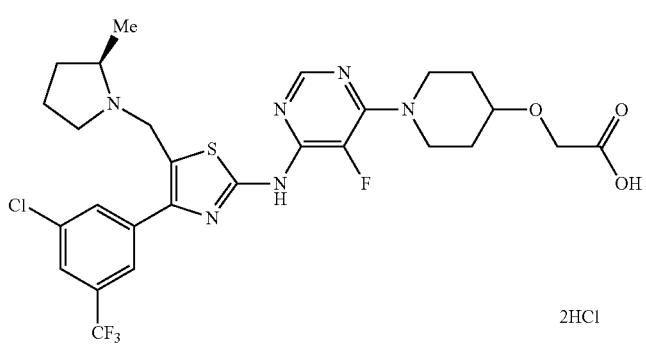 [SMILES: C[C@@H]1CCCN1Cc1sc(Nc2ncnc(N3CCC(OCC(=O)O)CC3)c2F)nc1-c1cc(Cl)cc(C(F)(F)F)c1] 2HCl |
| 68 | 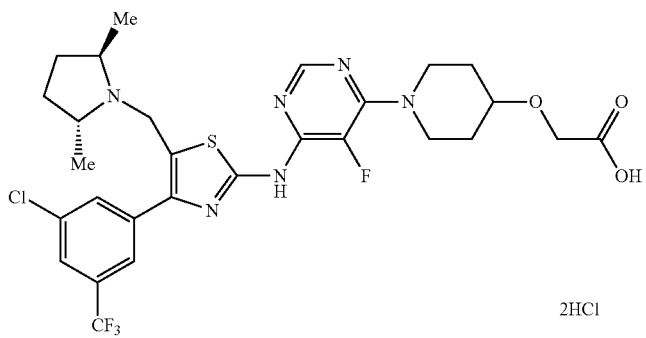 [SMILES: C[C@@H]1CC[C@@H](C)N1Cc1sc(Nc2ncnc(N3CCC(OCC(=O)O)CC3)c2F)nc1-c1cc(Cl)cc(C(F)(F)F)c1] 2HCl |
| 69 | 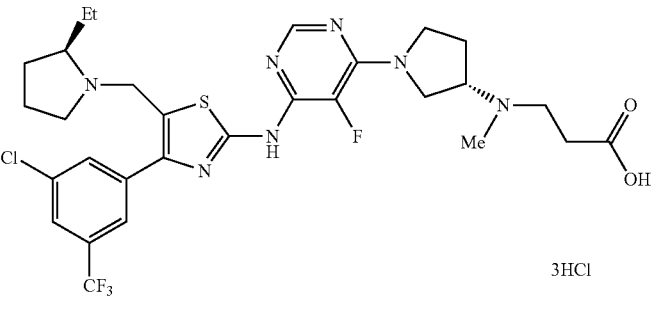 [SMILES: CC[C@@H]1CCCN1Cc1sc(Nc2ncnc(N3CC[C@H](N(C)CCC(=O)O)C3)c2F)nc1-c1cc(Cl)cc(C(F)(F)F)c1] 3HCl |
TABLE 88
| Ex | Str |
|---|---|
| 70 | 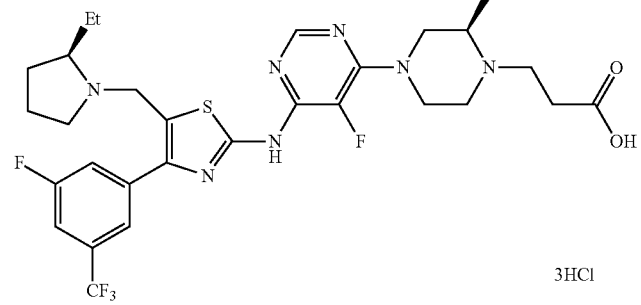 3HCl |

TABLE 88-continued
| Ex | Str |
|---|---|
| 71 | 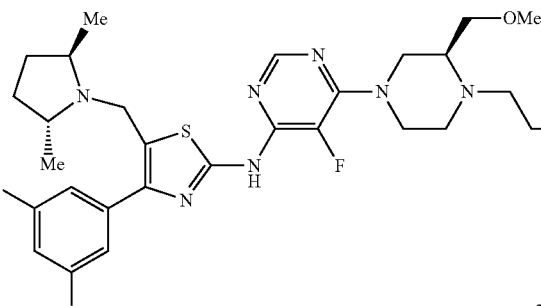 3HCl |
| 72 | 3HCl |
TABLE 89
| Ex | Str |
|---|---|
| 73 | 3HCl |
| 74 | 3HCl |

TABLE 89-continued
| Ex | Str |
|---|---|
| 75 | 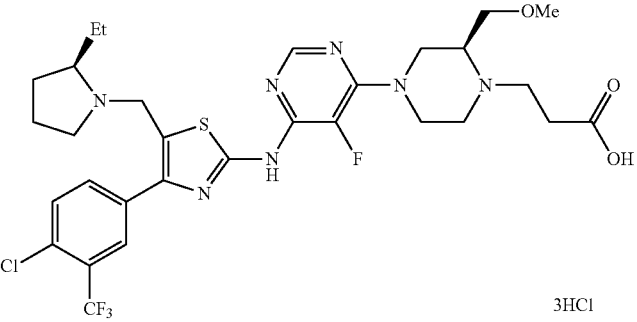 [SMILES: CC[C@@H]1CCCN1Cc1sc(Nc2ncnc(N3CCN(CCC(=O)O)[C@H](COC)C3)c2F)nc1-c1ccc(Cl)c(C(F)(F)F)c1] 3HCl |
TABLE 90
| Ex | Str |
|---|---|
| 76 | 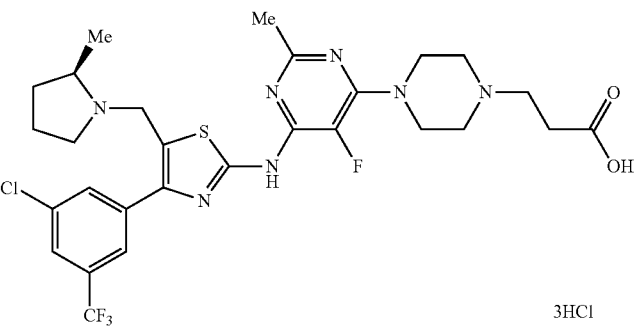 [SMILES: Cc1nc(Nc2nc(-c3cc(Cl)cc(C(F)(F)F)c3)c(CN3CCC[C@H]3C)s2)c(F)c(N2CCN(CCC(=O)O)CC2)n1] 3HCl |
| 77 | 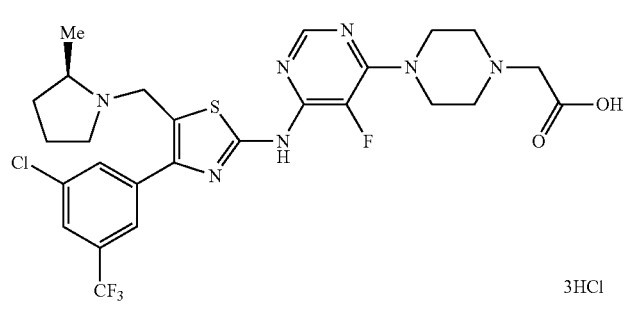 [SMILES: C[C@@H]1CCCN1Cc1sc(Nc2ncnc(N3CCN(CC(=O)O)CC3)c2F)nc1-c1cc(Cl)cc(C(F)(F)F)c1] 3HCl |
| 78 | 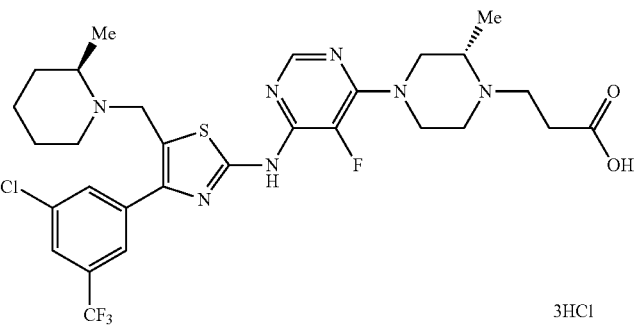 [SMILES: C[C@@H]1CCCCN1Cc1sc(Nc2ncnc(N3CCN(CCC(=O)O)[C@@H](C)C3)c2F)nc1-c1cc(Cl)cc(C(F)(F)F)c1] 3HCl |

TABLE 90-continued
| Ex | Str |
|---|---|
| 79 | 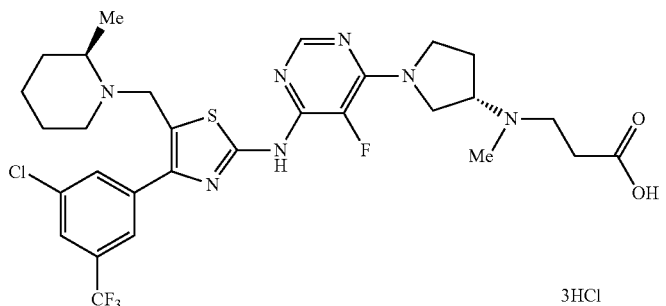 3HCl |
TABLE 91
| Ex | Str |
|---|---|
| 80 | 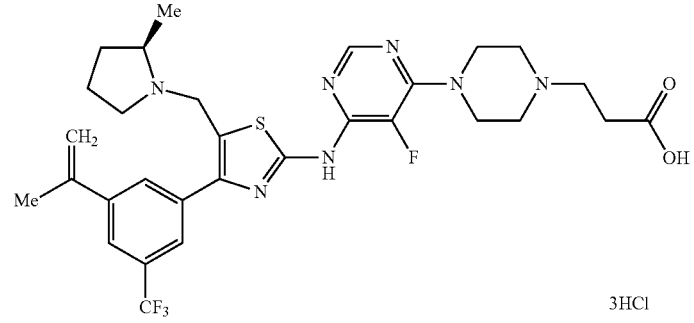 [SMILES: C=C(C)c1cc(-c2nc(Nc3ncnc(N4CCN(CCC(=O)O)CC4)c3F)sc2CN2CCC[C@H]2C)cc(C(F)(F)F)c1] 3HCl |
| 81 | 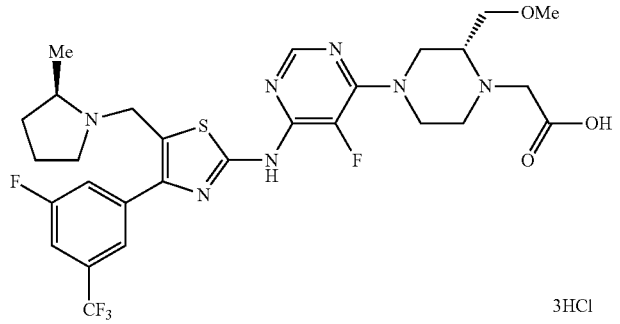 [SMILES: COC[C@H]1CN(c2ncnc(Nc3nc(-c4cc(F)cc(C(F)(F)F)c4)c(CN4CCC[C@H]4C)s3)c2F)CCN1CC(=O)O] 3HCl |
| 82 | 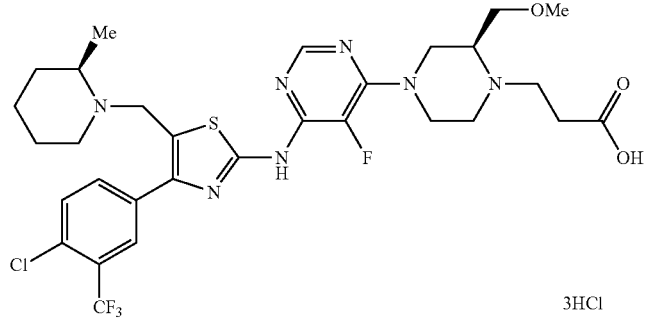 [SMILES: COC[C@@H]1CN(c2ncnc(Nc3nc(-c4ccc(Cl)c(C(F)(F)F)c4)c(CN4CCCC[C@H]4C)s3)c2F)CCN1CCC(=O)O] 3HCl |

TABLE 91-continued
| Ex | Str |
|---|---|
| 83 | 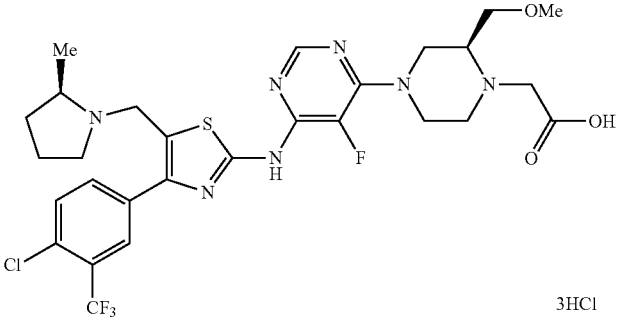 [SMILES: COC[C@@H]1CN(c2ncnc(Nc3nc(-c4ccc(Cl)c(C(F)(F)F)c4)c(CN4CCC[C@H]4C)s3)c2F)CCN1CC(=O)O] 3HCl |
TABLE 92
| Ex | Str |
|---|---|
| 84 | Na+ |
| 85 | Na+ |
| 86 | Na+ |

TABLE 93
| Ex | Str |
|---|---|
| 87 | 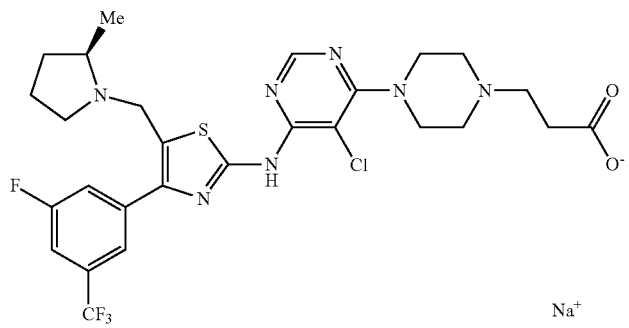 [SMILES: C[C@@H]1CCCN1Cc1sc(Nc2ncnc(N3CCN(CCC(=O)[O-])CC3)c2Cl)nc1-c1cc(F)cc(C(F)(F)F)c1 ; [Na+]] |
| 88 | 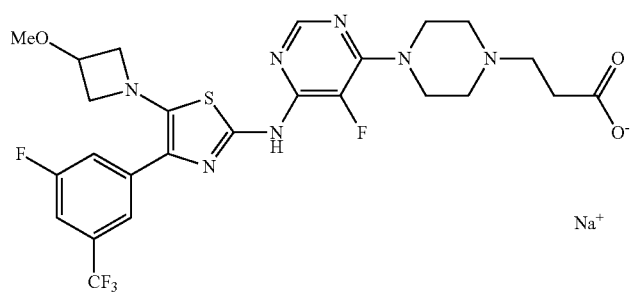 [SMILES: COC1CN(c2sc(Nc3ncnc(N4CCN(CCC(=O)[O-])CC4)c3F)nc2-c2cc(F)cc(C(F)(F)F)c2)C1 ; [Na+]] |
| 89 | 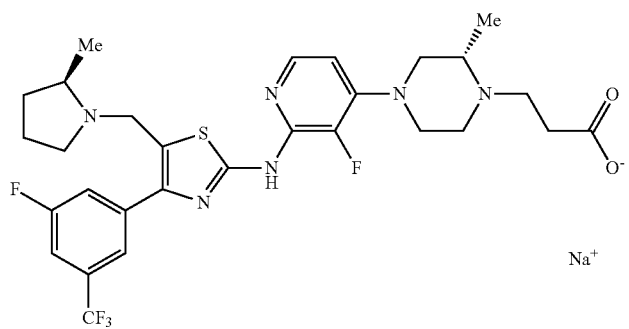 [SMILES: C[C@@H]1CCCN1Cc1sc(Nc2nccc(N3CCN(CCC(=O)[O-])[C@@H](C)C3)c2F)nc1-c1cc(F)cc(C(F)(F)F)c1 ; [Na+]] |
| 90 | 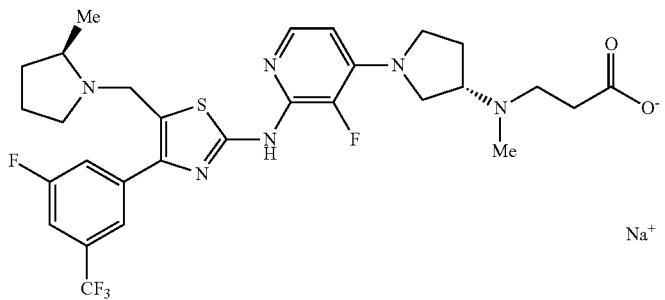 [SMILES: C[C@@H]1CCCN1Cc1sc(Nc2nccc(N3CC[C@H](N(C)CCC(=O)[O-])C3)c2F)nc1-c1cc(F)cc(C(F)(F)F)c1 ; [Na+]] |

TABLE 94
| Ex | Str | |
|---|---|---|
| 91 | 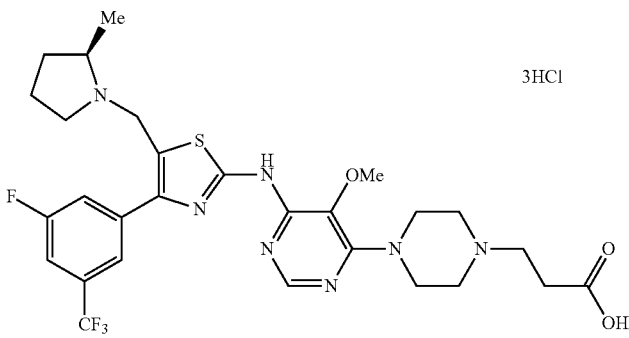 [SMILES: COc1c(Nc2nc(-c3cc(F)cc(C(F)(F)F)c3)c(CN3CCC[C@H]3C)s2)ncnc1N1CCN(CCC(=O)O)CC1] | 3HCl |
| 92 | 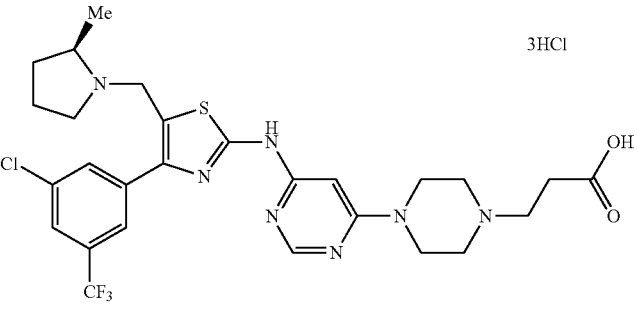 [SMILES: C[C@@H]1CCCN1Cc1sc(Nc2cc(N3CCN(CCC(=O)O)CC3)ncn2)nc1-c1cc(Cl)cc(C(F)(F)F)c1] | 3HCl |
| 93 | 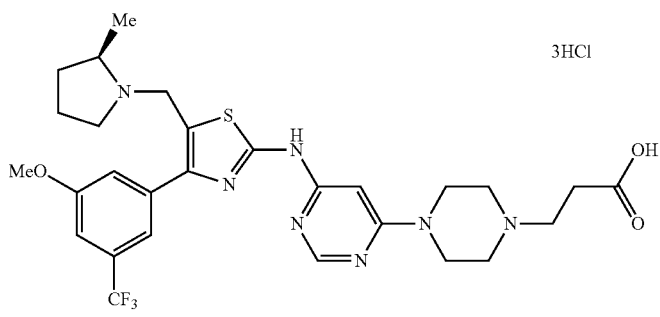 [SMILES: COc1cc(-c2nc(Nc3cc(N4CCN(CCC(=O)O)CC4)ncn3)sc2CN2CCC[C@H]2C)cc(C(F)(F)F)c1] | 3HCl |
| 94 | 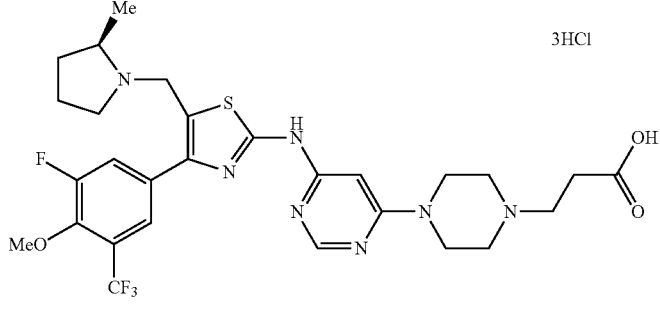 [SMILES: COc1c(F)cc(-c2nc(Nc3cc(N4CCN(CCC(=O)O)CC4)ncn3)sc2CN2CCC[C@H]2C)cc1C(F)(F)F] | 3HCl |

TABLE 95
| Ex | Str |
|---|---|
| 95 | 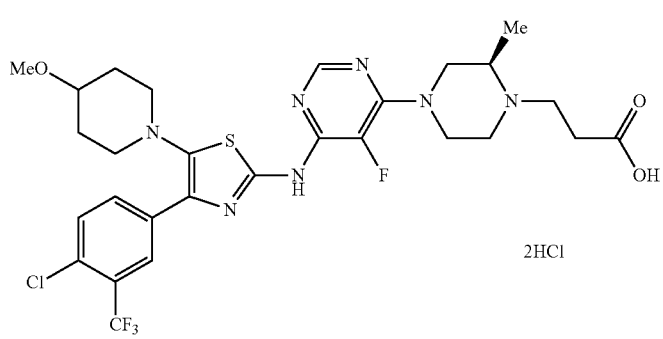 [SMILES: COC1CCN(c2sc(Nc3ncnc(N4CCN(CCC(=O)O)[C@H](C)C4)c3F)nc2-c2ccc(Cl)c(C(F)(F)F)c2)CC1] |
| 96 | 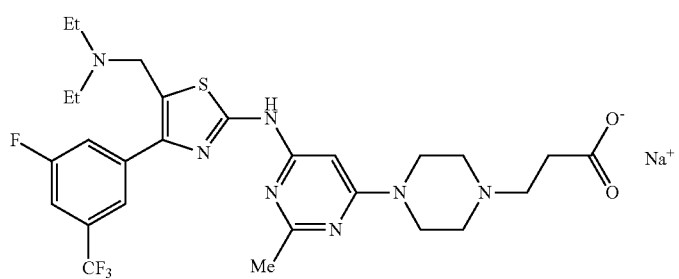 [SMILES: CCN(CC)Cc1sc(Nc2cc(N3CCN(CCC(=O)[O-])CC3)nc(C)n2)nc1-c1cc(F)cc(C(F)(F)F)c1 ; [Na+]] |
| 97 | 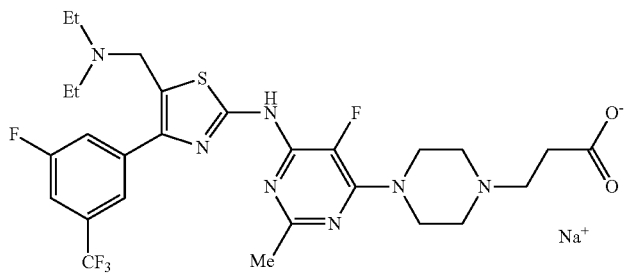 [SMILES: CCN(CC)Cc1sc(Nc2nc(C)nc(N3CCN(CCC(=O)[O-])CC3)c2F)nc1-c1cc(F)cc(C(F)(F)F)c1 ; [Na+]] |
| 98 | 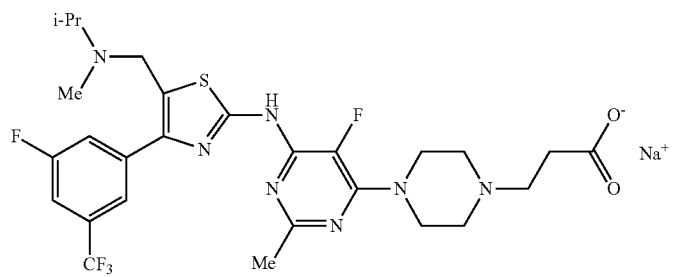 [SMILES: Cc1nc(Nc2nc(-c3cc(F)cc(C(F)(F)F)c3)c(CN(C)C(C)C)s2)c(F)c(N2CCN(CCC(=O)[O-])CC2)n1 ; [Na+]] |

TABLE 96

| Ex | Str |
|---|---|
| 99 | (structure: 2,5-dimethylpyrrolidine-CH2-thiazole with 3-fluoro-5-(trifluoromethyl)phenyl, NH-pyrimidine(2-Me)-piperazine-CH2CH2-COO⁻ Na⁺) |
| 100 | (structure: 2,5-dimethylpyrrolidine-CH2-thiazole with 3-fluoro-5-(trifluoromethyl)phenyl, NH-(3-fluoropyridine)-piperazine-CH2CH2-COOH; 3HCl) |
| 101 | (structure: 2-ethylpyrrolidine-CH2-thiazole with 2-methoxy-5-(trifluoromethyl)pyridin-5-yl, NH-(5-fluoropyrimidine)-piperazine-CH2CH2-COOH) |

TABLE 97

| Ex | Str |
|---|---|
| 102 | (structure: 2,5-dimethylpyrrolidine-CH2-thiazole with 2-methoxy-5-(trifluoromethyl)pyridin-5-yl, NH-(5-fluoropyrimidine)-piperazine-CH2CH2-COOH) |

TABLE 98

| Ex | Syn | DAT |
|---|---|---|
| 1 | 1 | ESI+: 672<br>NMR-DMSO-d6: 1.29-1.40 (3H, m), 1.52-1.71 (1H, m), 1.82-1.97 (2H, m), 2.11-2.23 (1H, m), 2.72-2.92 (2H, m), 2.99-3.18 (1H, m), 3.18-3.95 (16H, m), 4.21-4.59 (3H, m), 4.71-4.81 (1H, m), 7.87 (1H, d, J = 8.4 Hz), 8.03 (1H, dd, J = |

TABLE 98-continued

| Ex | Syn | DAT |
|---|---|---|
| | | 8.3, 1.9 Hz), 8.15 (1H, d, J = 1.9 Hz), 8.31 (1H, s), 10.36 (1H, brs), 10.74 (1H, brs), 12.02 (1H, brs) |
| 2 | 2 | ESI-: 625,627 |
| 3 | 3 | ESI+: 608<br>NMR-DMSO-d6: 1.38 (3H, d, J = 6.4 Hz), 1.60-1.74 (1H, m), 1.85-1.96 (2H, m), 2.10-2.24 (1H, m), 2.48 (3H, s), 2.88 (2H, t, J = 7.6 Hz), 3.00-3.18 (3H, m), 3.30-3.46 (5H, m), 3.49-3.62 (3H, m), 3.70-4.20 (2H, m), 4.28-4.48 (3H, m), 4.70-4.80 (1H, m), 6.14 (1H, s), 7.76-7.82 (1H, m), 7.87-7.96 (2H, m), 10.65 (1H, brs), 11.26 (1H, brs), 11.75 (1H, brs) |
| 4 | 4 | ESI-: 638<br>NMR-DMSO-d6: 0.97 (6H, d, J = 6.2 Hz), 1.28-1.39 (2H, m), 1.89-2.01 (2H, m), 2.07-2.13 (1H, m), 2.34 (3H, s), 2.38-2.58 (7H, m), 3.00-3.10 (2H, m), 3.50-3.60 (4H, m), 3.67 (1H, d, J = 14.4 Hz), 3.96 (1H, d, J = 14.4 Hz), 7.55-7.61 (1H, m), 8.06-8.15 (2H, m) |
| 5 | 5 | ESI+: 611<br>NMR-DMSO-d6: 1.38 (3H, d, J = 6.4 Hz), 1.58-1.74 (1H, m), 1.85-1.97 (2H, m), 2.10-2.23 (1H, m), 2.91 (2H, t, J = 7.7 Hz), 3.09-3.28 (3H, m), 3.30-3.64 (8H, m), 3.64-4.30 (2H, m), 4.38-4.48 (1H, m), 4.66-4.79 (1H, m), 6.80 (1H, t, J = 6.0 Hz), 7.76-7.82 (1H, m), 7.90-8.01 (3H, m), 10.70 (1H, brs), 11.20-11.90 (2H, m) |
| 6 | 6 | ESI-: 607, 609 |

TABLE 99

| Ex | Syn | DAT |
|---|---|---|
| 7 | 7 | ESI+: 625<br>NMR-DMSO-d6: 1.11 (3H, d, J = 6.2 Hz), 1.29-1.47 (1H, m), 1.56-1.70 (2H, m), 1.87-2.02 (1H, m), 2.05-2.20 (1H, m), 2.37-2.46 (3H, m), 2.55-2.62 (2H, m), 2.94-3.02 (1H, m), 3.21-3.41 (5H, m), 3.62-3.70 (4H, m), 4.04 (3H, s), 4.11-4.18 (1H, m), 8.20 (1H, d, J = 1.5 Hz), 8.51 (1H, d, J = 2.2 Hz), 8.80 (1H, d, J = 1.8 Hz), 11.42 (1H, brs), 12.23 (1H, brs) |
| 8 | 8 | ESI-: 624<br>NMR-DMSO-d6: 0.94 (6H, d, J = 6.2 Hz), 1.27-1.37 (2H, m), 1.90-2.01 (2H, m), 2.11-2.17 (2H, m), 2.41-2.55 (6H, m), 3.00-3.08 (2H, m), 3.52-3.61 (4H, m), 3.69 (1H, d, J = 14.4 Hz), 3.99 (1H, d, J = 14.4 Hz), 7.54-7.61 (1H, m), 7.99-8.14 (3H, m) |
| 9 | 9 | ESI+: 628, 630<br>NMR-DMSO-d6: 1.35-1.40 (3H, m), 1.59-1.72 (1H, m), 1.85-1.98 (2H, m), 2.12-2.22 (1H, m), 2.88 (2H, t, J = 8.0 Hz), 3.05-3.64 (12H, m), 4.38-4.48 (3H, m), 4.71-4.77 (1H, m), 7.87 (1H, d, J = 8.4 Hz), 8.06 (1H, dd, J = 8.3, 2.0 Hz), 8.17 (1H, d, J = 2.0 Hz), 8.31 (1H, d, J = 1.6 Hz), 10.67 (1H, brs), 11.47 (1H, brs), 12.03 (1H, brs) |
| 10 | 10 | ESI+: 656<br>NMR-DMSO-d6: 1.36 (3H, d, J = 6.2 Hz), 1.55-1.71 (1H, m), 1.83-1.98 (2H, m), 2.08-2.26 (1H, m), 2.76-2.91 (2H, m), 3.05-3.19 (1H, m), 3.20-4.03 (16H, m), 4.31-4.55 (3H, m), 4.70-4.85 (1H, m), 7.74-7.88 (1H, m), 7.90-7.96 (2H, m), 8.31 (1H, s), 10.45 (1H, brs), 10.73 (1H, brs), 12.01 (1H, brs) |

TABLE 100

| Ex | Syn | DAT |
|---|---|---|
| 11 | 11 | ESI-:626, 628<br>NMR-DMSO-d6: 1.41 (3H, d, J = 6.4 Hz), 1.61-1.74 (1H, m), 1.88-1.98 (2H, m), 2.14-2.24 (1H, m), 2.88 (2H, t, J = 7.7 Hz), 3.10-3.65 (13H, m), 4.38-4.49 (3H, m), 4.71-4.78 (1H, m), 7.97 (1H, s), 8.08 (1H, s), 8.19 (1H, s), 8.31 (1H, d, J = 1.6 Hz), 10.84 (1H, brs), 11.51 (1H, brs), 12.02 (1H, brs) |
| 12 | 12 | ESI+: 613<br>NMR-DMSO-d6: 1.34 (3H, d, J = 6.4 Hz), 1.47-1.70 (3H, m), 1.82-2.01 (4H, m), 2.13-2.23 (1H, m), 3.05-3.15 (1H, m), 3.34-3.73 (7H, m), 3.97-4.07 (2H, m), 4.08 (2H, s), 4.46 (1H, dd, J = 14.8, 7.9 Hz), 4.75-4.85 (1H, m), 7.79-7.84 (1H, m), 7.86-7.93 (2H, m), 8.22 (1H, d, J = 1.5 Hz), 9.97 (1H, brs), 11.83 (1H, brs) |
| 13 | 13 | ESI+: 643, 645<br>NMR-DMSO-d6: 0.84 (3H, t, J = 7.4 Hz), 1.46-1.68 (4H, m), 1.77-1.99 (5H, m), 2.11-2.23 (1H, m), 3.10-3.29 (2H, m), 3.34-3.73 (6H, m), 3.98-4.07 (2H, m), 4.08 (2H, s), 4.48 (1H, dd, J = 15.0, 7.5 Hz), 4.77 (1H, dd, J = 14.7, 1.9 Hz), 7.98 (1H, s), 8.03 (1H, s), 8.12 (1H, s), 8.22 (1H, d, J = 1.5 Hz), 10.17-10.28 (1H, m), 11.83 (1H, brs) |
| 14 | 1 | ESI+: 594<br>NMR-DMSO-d6: 1.38 (3H, d, J = 6.4 Hz), 1.60-1.72 (1H, m), 1.85-1.97 (2H, m), 2.11-2.23 (1H, m), 2.89 (2H, t, J = 7.7 Hz), 3.02-3.20 (3H, m), 3.28-3.63 (8H, m), 3.85-4.49 (5H, m.), 4.73 (1H, dd, J = 14.8, 2.0 Hz), 6.33 (1H, s), 7.76-7.82 (1H, m), 7.89-7.97 (2H, m), 8.46-8.49 (1H, m), 10.62-10.72 (1H, m), 11.42 (1H, brs), 11.85 (1H, brs) |
| 15 | 1 | ESI+: 622 |
| 16 | 1 | ESI+: 594 |

TABLE 101

| Ex | Syn | DAT |
|---|---|---|
| 17 | 1 | ESI+: 612<br>NMR-DMSO-d6: 1.38 (3H, d, J = 6.4 Hz), 1.60-1.74 (1H, m), 1.84-1.97 (2H, m), 2.12-2.22 (1H, m), 2.88 (2H, t, J = 7.7 Hz), 3.06-3.24 (3H, m), 3.27-3.36 (2H, m), 3.36-3.48 (1H, m), 3.48-3.64 (5H, m), 3.90-4.38 (2H, m), 4.38-4.50 (3H, m), 4.70-4.80 (1H, m), 7.77-7.83 (1H, m), 7.90-8.02 (2H, m), 8.31 (1H, d, J = 1.4 Hz), 10.60-10.80 (1H, m), 11.45 (1H, brs), 12.01 (1H, brs) |
| 18 | 1 | ESI+: 626<br>NMR-DMSO-d6: 1.39 (3H, d, J = 6.4 Hz), 1.62-1.74 (1H, m), 1.85-1.97 (2H, m), 2.10-2.22 (1H, m), 2.48 (3H, s), 2.88 (2H, t, J = 7.7 Hz), 3.05-3.22 (3H, m), 3.26-3.36 (2H, m), 3.36-3.62 (6H, m), 4.00-4.55 (5H, m), 4.70-4.80 (1H, m), 7.77-7.83 (H, m), 7.89-7.99 (2H, m), 10.85-10.98 (1H, m), 11.44 (1H, brs), 11.92 (1H, brs) |
| 19 | 1 | ESI+: 593<br>NMR-DMSO-d6: 1.38 (3H, d, J = 6.4 Hz), 1.60-1.74 (1H, m), 1.85-1.96 (2H, m), 2.10-2.23 (1H, m), 2.90 (2H, t, J = 7.7 Hz), 3.04-3.25 (3H, m), 3.29-3.68 (8H, m), 3.92-5.20 (2H, m), 4.41 (1H, dd, J = 14.9, 7.8 Hz), 4.66-4.76 (1H, m), 6.53-7.00 (2H, m), 7.80 (1H, d, J = 8.6 Hz), 7.94-8.02 (2H, m), 8.07 (1H, d, J = 6.8 Hz), 10.89 (1H, brs), 11.59 (1H, brs) |
| 20 | 1 | ESI+: 608 |
| 21 | 1 | ESI+: 622 |
| 22 | 1 | ESI+: 608 |
| 23 | 3 | ESI-: 588 |

TABLE 102

| Ex | Syn | DAT |
|---|---|---|
| 24 | 1 | ESI+: 607<br>NMR-DMSO-d6: 0.99-1.11 (3H, m), 1.34 (3H, d, J = 6.4 Hz), 1.43-1.69 (4H, m), 1.69-1.78 |

TABLE 102-continued

| Ex | Syn | DAT |
|---|---|---|
|  |  | (2H, m), 1.83-1.97 (2H, m), 2.11-2.22 (1H, m), 2.26 (2H, t, J = 7.5 Hz), 2.44 (3H, s), 2.85 (2H, t, J = 11.6 Hz), 3.03-3.16 (1H, m), 3.29-3.72 (3H, m), 4.15-4.32 (2H, m), 4.45 (1H, dd, J = 14.8, 7.7 Hz), 4.79 (1H, dd, J = 14.9, 2.3 Hz), 6.08 (1 H, brs), 7.75-7.82 (1H, m), 7.83-7.91 (2H, m), 9.97 (1H, brs), 11.57 (1H, brs) |
| 25 | 1 | ESI+: 593 |
| 26 | 1 | ESI+: 626 NMR-DMSO-d6: 1.05 (6H, d, J = 6.4 Hz), 2.42 (3H, s), 2.85 (2H, t, J = 7.6 Hz), 3.02-3.23 (8H, m), 3.29-3.41 (6H, m), 3.48-3.64 (2H, m), 3.94-4.50 (4H, m), 6.27 (1H, s), 7.54 (1H, d, J = 8.4 Hz), 8.40(1H, d, J = 11.3 Hz), 8.54 (1H, s), 10.82 (1H, brs), 11.30 (1H, brs) |
| 27 | 1 | ESI+: 624 |
| 28 | 1 | ESI+: 609 NMR-DMSO-d6: 1.37 (3H, d, J = 6.4 Hz), 1.58-1.70 (1H, m), 1.84-1.97 (2H, m), 1.98-2.23 (3H, m), 2.45 (2H, t, J = 6.3 Hz), 3.04-3.16 (1H, m), 3.31-3.73 (13H, m), 4.22 (1H, brs), 4.44 (1H, dd, J = 14.9, 7.8 Hz), 4.78 (1H, dd, J = 14.8, 2.4 Hz), 5.97 (1H, brs), 7.75-7.84 (1H, m), 7.86-7.94 (2H, m), 10.37 (1H, brs), 11.79 (1H, brs) |
| 29 | 1 | ESI−: 610 |
| 30 | 1 | ESI+: 609 |
| 31 | 1 | ESI+: 626 |

TABLE 103

| Ex | Syn | DAT |
|---|---|---|
| 32 | 1 | ESI+: 644, 646 NMR-DMSO-d6: 1.40-1.51 (1H, m), 1.53-1.64 (1H, m), 1.80-1.94 (2H, m), 2.65-2.80 (2H, m), 2.84-2.96 (3H, m), 3.08-3.21 (3H, m), 3.26 (3H, s), 3.27-3.35 (2H, m), 3.37-3.44 (1H, m), 3.48-3.62 (4H, m), 4.35-4.46 (2H, m), 4.70-7.19 (2H, m), 7.79 (1H, d, J = 8.6 Hz), 8.25 (1H, d, J = 1.4 Hz), 8.43 (1H, dd, J = 8.5, 2.0 Hz), 8.74 (1H, d, J = 2.0 Hz), 10.90-12.03 (2H, m) |
| 33 | 1 | ESI+: 600 |
| 34 | 1 | ESI+: 626 NMR-DMSO-d6: 1.32-1.40 (3H, m), 1.56-1.71 (1H, m), 1.83-1.97(2H, m), 2.11-2.23 (1H, m), 2.28-2.46 (3H, m), 2.75-2.81 (3H, m), 2.83-2.91 (2H, m), 3.06-3.18 (1H, m), 3.21-3.33 (1H, m), 3.36-3.55 (3H, m), 3.59-3.70 (1H, m), 3.88-4.18 (6H, m), 4.40-4.49 (1H, m), 4.73-4.81 (1H, m), 7.78-7.83 (1H, m), 7.90-7.95 (2H, m), 8.23 (1H, d, J = 1.8 Hz), 10.34 (1H, brs), 11.23 (1H, brs), 11.88 (1H, brs) |
| 35 | 1 | ESI+: 642, 644 |
| 36 | 1 | ESI−: 640, 642 |
| 37 | 1 | ESI+: 646 |
| 38 | 1 | ESI+: 640 |
| 39 | 1 | ESI+: 613 NMR-DMSO-d6: 1.35 (3H, d, J = 6.6 Hz), 1.56-1.69 (1H, m), 1.84-1.97(7H, m), 2.13-2.22 (1H, m), 3.04-3.16 (1H, m), 3.23 (3H, s), 3.34-3.55 (5H, m), 4.00-4.11 (2H, m), 4.39-4.50 (1H, m), 4.75-483 (1H, m), 7.77-7.85 (1H, m), 7.87-7.94 (2H, m), 8.24(1H, d, J = 1.6 Hz), 10.06 (1H, brs), 11.84 (1H, brs) |
| 40 | 1 | ESI−: 640 |
| 41 | 1 | ESI+: 640 |

TABLE 104

| Ex | Syn | DAT |
|---|---|---|
| 42 | 1 | ESI+: 639 NMR-DMSO-d6: 0.77-0.88 (2H, m), 1.07-1.27 (2H, m), 2.83 (2H, t, J = 7.5 Hz), 2.95-3.69 (18H, m), 4.34-4.52 (2H, m), 7.61-7.67 (1H, m), 8.24-8.33 (3H, m), 10.66 (1H, brs), 11.20 (1H, brs), 11.59 (1H, s), 12.74 (1H, brs) |
| 43 | 1 | ESI+: 642 |
| 44 | 1 | ESI+: 640 |
| 45 | 1 | ESI+: 644 NMR-DMSO-d6: 1.32-1.40 (3H, m), 1.59-1.71 (1H, m), 1.83-1.97 (2H, m), 2.12-2.23 (1H, m), 2.81-2.93 (2H, m), 3.07-3.18 (1H, m), 3.22-4.62 (14H, m), 4.72-4.80 (1H, m), 4.85-5.12 (2H, m), 7.79-7.83 (1H, m), 7.91-7.98 (2H, m), 8.32 (1H, s), 10.55 (1H, brs), 11.46 (1H, brs), 12.04 (1H, brs) |
| 46 | 1 | ESI+: 640 |
| 47 | 1 | ESI+: 641 |
| 48 | 1 | ESI+: 628 |
| 49 | 1 | ESI+: 656 |
| 50 | 1 | ESI+: 632 |
| 51 | 1 | ESI−: 642, 644 NMR-DMSO-d6: 1.38(3H, d, J = 6.4 Hz), 1.60-1.73 (1H, m), 1.86-1.96 (2H, m), 2.11-2.22 (1H, m), 2.88 (2H, t, J = 7.6 Hz), 3.07-3.23 (3H, m), 3.28-4.20 (10H, m), 4.37-4.48 (3H, m), 4.68-4.76 (1H, m), 7.67-7.72 (2H, m), 7.92 (1H, t, J = 1.7 Hz), 8.31 (1H, d, J = 1.4 Hz), 10.74 (1H, brs), 11.48 (1H, brs), 12.01 (1H, brs) |
| 52 | 1 | ESI+: 656 |
| 53 | 1 | ESI+: 642 |
| 54 | 1 | ESI+: 627 |
| 55 | 1 | ESI+: 672 |
| 56 | 1 | ESI+: 642 |
| 57 | 1 | ESI−: 654, 656 |
| 58 | 1 | ESI+: 644 |

TABLE 105

| Ex | Syn | DAT |
|---|---|---|
| 59 | 1 | ESI+: 660, 662 NMR-DMSO-d6: 1.29-1.43 (3H, m), 1.55-1.70 (1H, m), 1.83-2.01 (2H, m), 2.11-2.23 (1H, m), 2.79-2.91 (2H, m), 3.02-3.94 (13H, m), 4.18-4.68 (3H, m), 4.72-4.81 (1H, m), 4.83-5.13 (2H, m), 7.87 (1H, d, J = 8.2 Hz), 8.03 (1H, dd, J = 8.4, 2.0 Hz), 8.15 (1H, d, J = 2.0 Hz), 8.32 (1H, s), 10.32 (1H, brs), 12.04 (1H, brs) |
| 60 | 1 | ESI+: 640 |
| 61 | 1 | ESI+: 640 |
| 62 | 1 | ESI+: 644 |
| 63 | 1 | ESI−: 640, 642 |
| 64 | 1 | ESI−: 654, 656 |
| 65 | 1 | ESI−: 654, 656 |
| 66 | 1 | ESI−: 640, 642 |
| 67 | 1 | ESI−: 627, 629 |
| 68 | 1 | ESI−: 641,643 |
| 69 | 1 | ESI+: 656 |
| 70 | 1 | ESI+: 670 |
| 71 | 1 | ESI−: 684, 686 |
| 72 | 1 | ESI+: 686, 688 |
| 73 | 1 | ESI+: 686 |
| 74 | 1 | ESI+: 672, 674 |
| 75 | 1 | ESI+: 686 |
| 76 | 1 | ESI+: 642 |
| 77 | 1 | ESI−: 612,614 NMR-DMSO-d6: 1.42 (3H, d, J = 6.4 Hz), 1.62-1.76 (1H, m), 1.87-1.99 (2H, m), 2.13-2.24 (1H, m), 3.14-3.26 (1H, m), 3.26-3.90 (12H, m), 4.19 (2H, s), 4.36-4.48 (1H, m), 4.69-4.78 (1H, m), 7.95-7.99 (1H, m), 8.06-8.09 (1H, m), 8.18-8.21 (1H, m), 8.31-8.33 (1H, m), 10.51-11.27 (2H, m), 12.01 (1H, brs) |
| 78 | 1 | ESI−: 654, 656 |
| 79 | 1 | ESI+: 656 |
| 80 | 1 | ESI−: 632 |

TABLE 106

| Ex | Syn | DAT |
|---|---|---|
| 81 | 1 | ESI+: 642 |
| 82 | 1 | ESI−: 684, 686 |
| 83 | 1 | ESI+: 658 |
| 84 | 2 | ESI+: 637<br>NMR-DMSO-d6: 1.13 (3H, d, J = 6.0 Hz), 1.28-1.42 (1H, m), 1.58-1.71 (2H, m), 1.88-2.02 (1H, m), 2.09-2.23 (3H, m), 2.36-2.44 (3H, m), 2.96-3.04 (1H, m), 3.14 (6H, s), 3.21-3.92 (8H, m), 3.34 (1H, d, J = 14.0 Hz), 4.13 (1H, d, J = 14.0 Hz), 5.51 (1H, s), 7.58-7.65 (1H, m), 8.01-8.06 (1H, m), 8.07 (1H, s), 10.98 (1H, s) |
| 85 | 2 | ESI+: 613 |
| 86 | 2 | ESI+: 642 |
| 87 | 2 | ESI+: 628 |
| 88 | 2 | ESI+: 600 |
| 89 | 2 | ESI+: 625 |
| 90 | 2 | ESI+: 625 |
| 91 | 3 | ESI+: 624<br>NMR-DMSO-d6: 1.38 (3H, d, J = 6.4 Hz), 1.60-1.73 (1H, m), 1.86-1.97 (2H, m), 2.10-2.23 (1H, m), 2.89 (2H, t, J = 7.7 Hz), 3.07-3.23 (3H, m), 3.27-3.36 (2H, m), 3.37-3.60 (6H, m), 3.66 (3H, s), 3.88-4.58 (5H, m), 4.70-4.80 (1H, m), 7.77-7.83 (1H, m), 7.92-8.00 (2H, m), 8.31 (1H, s), 10.60-10.75 (1H, m), 11.32-11.56 (2H, m) |
| 92 | 3 | ESI−: 608,610 |
| 93 | 3 | ESI−: 604 |
| 94 | 3 | ESI−: 622 |
| 95 | 3 | ESI+: 658, 660 |
| 96 | 4 | ESI+: 596 |
| 97 | 4 | ESI+: 614 |
| 98 | 4 | ESI+: 614 |
| 99 | 4 | ESI−: 620 |
| 100 | 5 | ESI+: 625 |
| 101 | 7 | ESI+: 639 |

TABLE 107

| Ex | Syn | DAT |
|---|---|---|
| 102 | 7 | ESI+: 639 |

INDUSTRIAL APPLICABILITY

The compound of the formula (I) or a salt thereof is a muscarinic $M_3$ receptor-positive allosteric modulator, and can thus be used as an agent for preventing or treating bladder/urinary tract diseases associated with bladder contractions via a muscarinic $M_3$ receptor.

The invention claimed is:

1. A compound of the formula (I) or a salt thereof:

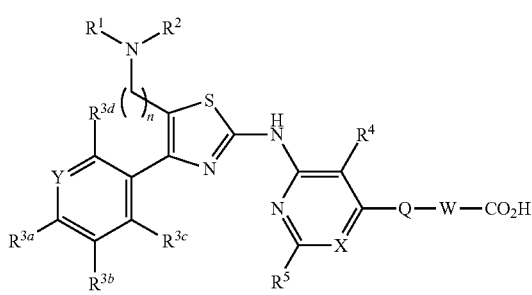

(I)

wherein:
X is C—H or N,
Y is C—$R^{3e}$ or N,
$R^1$ and $R^2$ are the same as each other or are different from each other, and are $C_{1-6}$ alkyl which may be substituted, or $R^1$ and $R^2$ may be combined with the adjacent nitrogen atom to form cyclic amino which may be substituted,
$R^{3a}$, $R^{3b}$, $R^{3c}$, and $R^{3d}$ are the same as each other or are different from each other, and are H, halogen, $C_{1-6}$ alkyl, halogeno $C_{1-6}$ alkyl, —O—$C_{1-6}$ alkyl, $C_{2-6}$ alkenyl, $C_{3-8}$ cycloalkyl, or —O-halogeno $C_{1-6}$ alkyl,
in a case where Y is C—$R^{3e}$, $R^{3e}$ is H, halogen, $C_{1-6}$ alkyl, halogeno $C_{1-6}$ alkyl, —(O—$C_{1-6}$ alkyl, $C_{2-6}$ alkenyl, $C_{3-8}$ cycloalkyl, or —O-halogeno $C_{1-6}$ alkyl,
$R^4$ is H, halogen, or —O—$C_{1-6}$ alkyl,
$R^5$ is H, $C_{1-6}$ alkyl, or —$NR^{51}R^{52}$,
Q is heterocyclylene which may be substituted,
W is a bond, $C_{1-6}$ alkylene, —O—$C_{1-6}$ alkylene, or —N($R^N$)—$C_{1-6}$ alkylene,
$R^{51}$ and $R^{52}$ are the same as each other or are different from each other, and are H or $C_{1-6}$ alkyl,
$R^N$ is H or $C_{1-6}$ alkyl, and
n is 0 or 1.

2. The compound or a salt thereof according to claim 1, wherein
$R^1$ and $R^2$
(i) are the same as each other or are different from each other, and are $C_{1-6}$ alkyl which may be substituted with —O—$C_{1-6}$ alkyl or $C_{3-8}$ cycloalkyl, or
(ii) $R^1$ and $R^2$ are combined with the adjacent nitrogen atom to form cyclic amino which may be substituted, and the cyclic amino is azetidinyl, pyrrolidinyl, piperidinyl, or piperazinyl,
Q is heterocyclylene which may be substituted, and the heterocyclylene is pyrrolidine-1,3-diyl, piperidine-1,4-diyl, or piperazine-1,4-diyl, and the 3-position of pyrrolidine or the 4-position of piperidine is bonded to W, and
W is a bond, $C_{1-6}$ alkylene, —O—$C_{1-6}$ alkylene or —N($R^N$)—$C_{1-6}$ alkylene, and $R^N$ is $C_{1-6}$ alkyl.

3. The compound or a salt thereof according to claim 2, wherein
X is N,
Y is C—$R^{3e}$,
$R^1$ and $R^2$ are combined with the adjacent nitrogen atom to form cyclic amino which may be substituted with $C_{1-6}$ alkyl, —O—$C_{1-6}$ alkyl, or $C_{3-8}$ cycloalkyl, and the cyclic amino is azetidinyl, pyrrolidinyl, piperidinyl, or piperazinyl,
$R^{3a}$, $R^{3c}$, $R^{3d}$, and $R^{3e}$ are the same as each other or are different from each other, and are H or halogen, and $R^{3b}$ is halogeno $C_{1-6}$ alkyl,
$R^4$ is H or halogen,
$R^5$ is H or $C_{1-6}$ alkyl,
Q is heterocyclylene which may be substituted with —$C_{1-6}$ alkylene-O—$C_{1-6}$ alkyl, and the heterocyclylene is piperidine-1,4-diyl or piperazine-1,4-diyl,
W is $C_{1-6}$ alkylene, or —O—$C_{1-6}$ alkylene, and
n is 1.

4. The compound or a salt thereof according to claim 3, wherein
$R^1$ and $R^2$ are combined with the adjacent nitrogen atom to form pyrrolidine which is substituted with one or two $C_{1-6}$ alkyl, R$^{3a}$, R$^{3c}$, R$^{3d}$, and R$^{3e}$ are the same as each other or are different from each other, and are H or halogen, and R$^{3b}$ is trifluoromethyl, and W is —CH$_2$—CH$_2$— or —O—CH$_2$—.

5. The compound or a salt thereof according to claim 1, wherein the compound is a compound selected from the group consisting of:

3-(4-{6-[(5-{[(2R,5R)-2,5-dimethylpyrrolidin-1-yl]methyl}-4-[3-fluoro-5-(trifluoromethyl)phenyl]-1,3-thiazol-2-yl)amino]-5-fluoropyrimidin-4-yl}piperazin-1-yl)propanoic acid, 3-(4-{6-[(5-{[(2R,5R)-2,5-dimethylpyrrolidin-1-yl]methyl}-4-[3-fluoro-5-(trifluoromethyl)phenyl]-1,3-thiazol-2-yl)amino]-5-fluoro-2-methylpyrimidin-4-yl}piperazin-1-yl)propanoic acid, 3-(4-{6-[(4-[4-chloro-3-(trifluoromethyl)phenyl]-5-[(2R)-2-methylpyrrolidin-1-yl]methyl}-1,3-thiazol-2-yl)amino]-5-fluoropyrimidin-4-yl}piperazin-1-yl)propanoic acid, 3-[(2S)-4-{5-fluoro-6-[(4-[3-fluoro-5-(trifluoromethyl)phenyl]-5-{[(2R)-2-methylpyrrolidin-1-yl]methyl}-1,3-thiazol-2-yl)amino]pyrimidin-4-yl}-2-(methoxymethyl)piperazin-1-yl]propanoic acid,

[(1-{5-fluoro-6-[(4-[3-fluoro-5-(trifluoromethyl)phenyl]-5-{[(2R)-2-methylpyrrolidin-1-yl]methyl}-1,3-thiazol-2-yl)amino]pyrimidin-4-yl}piperidin-4-yl)oxy]acetic acid, and 3-[(2S)-4-{6-[(4-[4-chloro-3-(trifluoromethyl)phenyl]-5-{[(2R)-2-methylpyrrolidin-1-yl]methyl}-1,3-thiazol-2-yl)amino]-5-fluoropyrimidin-4-yl}-2-(methoxymethyl)piperazin-1-yl]propanoic acid.

6. A pharmaceutical composition comprising the compound or a salt thereof according to claim 5, and a pharmaceutically acceptable excipient.

7. A method for treating bladder/urinary tract diseases associated with bladder contractions via a muscarinic M$_3$ receptor, comprising administering to a subject in need thereof an effective amount of the compound or a salt thereof according to claim 5.

8. The compound or a salt thereof according to claim 5, wherein the compound is 3-(4-{6-[(5-{[(2R,5R)-2,5-dimethylpyrrolidin-1-yl]methyl}-4-[3-fluoro-5-(trifluoromethyl)phenyl]-1,3-thiazol-2-yl)amino]-5-fluoropyrimidin-4-yl}piperazin-1-yl)propanoic acid.

9. The compound or a salt thereof according to claim 5, wherein the compound is 3-(4-{6-[(5-{[(2R,5R)-2,5-dimethylpyrrolidin-1-yl]methyl}-4-[3-fluoro-5-(trifluoromethyl)phenyl]-1,3-thiazol-2-yl)amino]-5-fluoro-2-methylpyrimidin-4-yl}piperazin-1-yl)propanoic acid.

10. The compound or a salt thereof according to claim 5, wherein the compound is 3-(4-{6-[(4-[4-chloro-3-(trifluoromethyl)phenyl]-5-{[(2R)-2-methylpyrrolidin-1-yl]methyl}-1,3-thiazol-2-yl)amino]-5-fluoropyrimidin-4-yl}piperazin-1-yl)propanoic acid.

11. The compound or a salt thereof according to claim 5, wherein the compound is 3-[(2S)-4-{5-fluoro-6-[(4-[3-fluoro-5-(trifluoromethyl)phenyl]-5-{[(2R)-2-methylpyrrolidin-1-yl]methyl}-1,3-thiazol-2-yl)amino]pyrimidin-4-yl}-2-(methoxymethyl)piperazin-1-yl]propanoic acid.

12. The compound or a salt thereof according to claim 5, wherein the compound is

[(1-{5-fluoro-6-[(4-[3-fluoro-5-(trifluoromethyl)phenyl]-5-{[(2R)-2-methylpyrrolidin-1-yl]methyl}-1,3-thiazol-2-yl)amino]pyrimidin-4-yl}piperidin-4-yl)oxy]acetic acid.

13. The compound or a salt thereof according to claim 5, wherein the compound is 3-[(2S)-4-{6-[(4-[4-chloro-3-(trifluoromethyl)phenyl]-5-{[(2R)-2-methylpyrrolidin-1-yl]methyl}-1,3-thiazol-2-yl)amino]-5-fluoropyrimidin-4-yl}-2-(methoxymethyl)piperazin-1-yl]propanoic acid.

\* \* \* \* \*